US008067586B2

(12) United States Patent
Hayakawa et al.

(10) Patent No.: US 8,067,586 B2
(45) Date of Patent: *Nov. 29, 2011

(54) FUSED HETEROARYL DERIVATIVES

(75) Inventors: Masahiko Hayakawa, Tsukuba (JP); Hiroyuki Kaizawa, Tsukuba (JP); Hiroyuki Moritomo, Tsukuba (JP); Ken-Ichi Kawaguchi, Tsukuba (JP); Tomonobu Koizumi, Tsukuba (JP); Mayumi Yamano, Tsukuba (JP); Koyo Matsuda, Tsukuba (JP); Minoru Okada, Tsukuba (JP); Mitsuaki Ohta, Tsukuba (JP)

(73) Assignees: Astellas Pharma Inc., Tokyo (JP); Ludwig Institute for Cancer Research, New York, NY (US); Imperial Cancer Research Technology Ltd., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/688,272

(22) Filed: Jan. 15, 2010

(65) Prior Publication Data
US 2010/0137584 A1 Jun. 3, 2010

Related U.S. Application Data

(60) Division of application No. 11/544,144, filed on Oct. 6, 2006, now abandoned, which is a continuation of application No. 11/250,782, filed on Oct. 14, 2005, now Pat. No. 7,173,029, which is a continuation of application No. 10/918,094, filed on Aug. 13, 2004, now Pat. No. 7,037,915, which is a continuation of application No. 10/459,002, filed on Jun. 10, 2003, now Pat. No. 6,838,457, which is a division of application No. 10/243,416, filed on Sep. 13, 2002, now Pat. No. 6,608,056, which is a division of application No. 09/843,615, filed on Apr. 26, 2001, now Pat. No. 6,608,053.

(60) Provisional application No. 60/200,537, filed on Apr. 27, 2000, provisional application No. 60/200,481, filed on Apr. 28, 2000.

(51) Int. Cl.
*C07D 413/00* (2006.01)
(52) U.S. Cl. .................................................. 544/117
(58) Field of Classification Search .................. 544/117
See application file for complete search history.

(56) References Cited

U.S. PATENT DOCUMENTS

| | | | |
|---|---|---|---|
| 3,661,908 A | 5/1972 | Woitun et al. | |
| 3,763,156 A | 10/1973 | Woitun et al. | |
| 3,808,211 A | 4/1974 | Benjamin | |
| 3,830,813 A | 8/1974 | Woitun et al. | |
| 3,907,799 A | 9/1975 | O'Brien et al. | |
| 4,007,187 A | 2/1977 | Fauran et al. | |
| 4,146,716 A | 3/1979 | Cox et al. | |
| 4,196,207 A | 4/1980 | Webber | |
| 4,306,065 A | 12/1981 | Chen | |
| 5,304,554 A | 4/1994 | Strekowski et al. | |
| 5,444,062 A | 8/1995 | Coe et al. | |
| 5,990,117 A | 11/1999 | Pamukcu et al. | |
| 6,271,225 B1 | 8/2001 | Seio et al. | |
| 6,420,391 B1 | 7/2002 | Konishi et al. | |
| 6,518,277 B1 | 2/2003 | Sadhu et al. | |
| 6,608,056 B1 * | 8/2003 | Hayakawa et al. | ........ 514/232.5 |
| 6,610,698 B2 | 8/2003 | Spohr et al. | |
| 6,838,457 B2 | 1/2005 | Hayakawa et al. | |
| 2005/0014771 A1 | 1/2005 | Hayakawa et al. | |

FOREIGN PATENT DOCUMENTS

| | | |
|---|---|---|
| DE | 2 039 663 | 2/1972 |
| EP | 0 276 057 A2 | 7/1988 |
| EP | 0 655 456 A1 | 5/1995 |
| EP | 0 882 717 | 12/1998 |
| EP | 1 067 123 A1 | 1/2001 |
| GB | 2 295 387 | 5/1996 |
| JP | 58-172379 | 10/1983 |
| JP | 10-87492 | 4/1988 |
| JP | 10-175977 | 6/1998 |
| JP | 11-209287 | 8/1999 |
| WO | WO 98/23613 | 6/1998 |
| WO | WO 99/43682 | 9/1999 |
| WO | WO 01/81346 | 11/2001 |

OTHER PUBLICATIONS

Abdel-Hamide, CAPLUS Abstract 132:151765, 1999.
Berrie, PubMed Abstract (Expert Opin. Investig. Drugs 10(6): 1085-98), 2001.
Bi, et al., "Proliferative defect and embryonic lethality [..]", J. Biol. Chem., 274, 10963-8 (1999).
Burguignon, et al., CAPLUS Abstract 83: 114329, 1975.
Di Cristofano, et al., "Pten is essential for embryonic development and tumor suppression", Nature Genetics, col. 19, pp. 348-355 (1998).
Maehama, et al., "The Tumor Suppressor[. . .]", J. Biol. Chem., 273, 13375-78, (1998).
Merino, et al., "Synthesis and Anti-HIV-1 activities of new pyrimido[5,4,-b]indoles", vol. 54, No. 4., pp. 255-264 (1999).
Misawa, et al., PubMed Abstract (Biochem. Biophys. Res. Commun. 244(2):531-9), 1998.
Mokrosz, et al., CAPLUS Abstract 126 :126498, 1997.
Nishigaki, et al., "Synthetic Antibacterials. Nitrofurylvinylpyrido[2,3-d]pyrimidine derivatives", J. Med. Chem., vol. 15, No. 7, pp. 731-734, 1972.
Osselaere, et al., Chemical Abstract 83 :9970n, 1975.

(Continued)

Primary Examiner — Nizal Chandrakumar
(74) Attorney, Agent, or Firm — Fulbright & Jaworski L.L.P.

(57) ABSTRACT

The present invention provides a pharmaceutical composition which is useful as a phosphatidylinositol 3 kinase (PI3K) inhibitor and an antitumor agent, and it provides a novel bicyclic or tricyclic fused heteroaryl derivative or a salt thereof which possesses an excellent PI3K inhibiting activity and cancer cell growth inhibiting activity.

6 Claims, No Drawings

OTHER PUBLICATIONS

Peinador, et al., A convenient synthesis for some new pyrido [3'2' :4,5]thieno-[3,2-d]pyrimidine derivativ es with potential biological activity, *J. Heterocycl. Chem*., 29(7) (1992), pp. 1693-1702 , Abstract.

Sangapure, et al., Chemical Abstract 134 :207777 (Indian Journal of Heterocyclic Chemistry, 10(1), pp. 21-26), 2000.

Simone, Oncology : Introduction, Cecil Textbook of Medicine, 20th Edition, vol. 1 , pp. 1004-1010, 1996.

Shioi, et al., "The conserved phosphoinositide 3-kinase pathway determines heart size in mice", EMBO J., 19, 2537-48 (2000).

Tsizin, et al., "Synthesis and Antimicrobial Action of N-substituted—Hydroxyquinazolines", vol. 7, No. 7, pp. 16-19 (1972).

Vaidya, et al. "Studies in Benzofurans: Part XII—Synthesis & Reactions . . . pyrimidine", In. J. Chem., vol. 20B, No. 9, pp. 780-783 (1981).

* cited by examiner

FUSED HETEROARYL DERIVATIVES

This application is a divisional application of U.S. Ser. No; 11/544,144 filed Oct. 6, 2006 now abandoned, which is a continuation application of U.S. Ser. No. 11/250,782 filed Oct. 14, 2005, now U.S. Pat. No. 7,173,029, which is a continuation application of U.S. Ser. No. 10/918,094 filed Aug. 13, 2004 now U.S. Pat. No. 7,037,915, which is a continuation application of U.S. Ser. No. 10/459,002 filed Jun. 10, 2003, now U.S. Pat. No. 6,838,457, which is a divisional application of U.S. Ser. No. 10/243,416 filed Sep. 13, 2002, now U.S. Pat. No. 6,608,056, which is a divisional application of U.S. Ser. No. 09/843,615 filed Apr. 26, 2001, now U.S. Pat. No. 6,608,053, and claims the benefit of U.S. provisional patent application Ser. No. 60/200,537 filed Apr. 27, 2000 and of U.S. provisional patent application Ser. No. 60/200,481 filed Apr. 28, 2000, each of which is incorporated herein by reference in its entirety.

FIELD OF THE INVENTION

The present invention relates to fused heteroaryl derivatives which are useful as medicaments, more particularly as phosphatidylinositol 3-kinase (PI3K) inhibitors and carcinostatic agents.

BACKGROUND OF THE INVENTION

Phosphatidylinositol (hereinafter abbreviated as "PI") is one of phospholipids in cell membranes. In recent years it has become clear that PI plays an important role also in intracellular signal transduction. It is well recognized in the art that especially PI (4,5) bisphosphate (PI(4,5)P2) is degraded into diacylglycerol and inositol (1,4,5) triphosphate by phospholipase C to induce activation of protein kinase C and intracellular calcium mobilization, respectively [M. J. Berridge et al., Nature, 312, 315 (1984); Y Nishizuka, Science, 225, 1365 (1984)].

Turning back to the late 1980s, PI3K was found to be an enzyme phosphorylate the 3-position of the inositol ring of phosphatidylinositol [D. Whitman et al., Nature, 332, 664 (1988)].

PI3K was originally considered to be a single enzyme at the time when PI3K was discovered. Recently it was clarified that a plurality of subtypes are present in the PI3K. Three classes of PI3Ks have now been identified on the basis of their in vitro substrate specificity [B. Vanhaesebroeck, Trend in Biol. Sci., 22, 267 (1997)].

Substrates for class I PI3Ks are PI, PI(4)P and PI (4,5)P2, in these substrates, PI(4,5)P2 is the most advantageous substrate in cells. Class I PI3Ks are further divided into two groups, class Ia and class Ib, in terms of their activation mechanism. Class Ia PI3Ks, which include PI3K p110α, p110β and p110δ subtypes, are activated in the tyrosine kinase system. Class Ib PI3K is a p110γ subtype activated by a G protein-coupled receptor.

PI and PI(4)P are known as substrates for class II PI3Ks but PI(4,5)P2 is not a substrate for the enzymes of this class. Class II PI3Ks include PI3K C2α, C2β and C2γ subtypes, which are characterized by containing C2 domains at the C terminus, implying that their activity will be regulated by calcium ions. The substrate for class III PI3Ks is PI only. A mechanism for activation of the class III PI3Ks is not clarified yet. Since each subtype has its own mechanism for the regulating activity, it is considered that the respective subtypes will be activated depending on their respective stimuli specific to each of them.

In the PI3K subtypes, the class Ia subtype has been most extensively investigated to date. The three subtypes of class Ia are hetero dimers of a catalytic 110 kDa subunit and regulatory subunits of 85 kDa and 55 kDa. The regulatory subunits contain SH2 domains and bind to tyrosine residues phosphorylated by growth factor receptors with a tyrosine kinase activity or oncogene products thereby inducing the PI3K activity of the p110 catalytic subunit. Thus, the class Ia subtypes are considered to be associated with cell proliferation and carcinogenesis. Furthermore, the class Ia PI3K subtypes bind to activated ras oncogene to express their enzyme activity. It has been confirmed that the activated ras oncogene is found to be present in many cancers, suggesting a role of class Ia PI3Ks in carcinogenesis.

As explained above, PI3K inhibitors are expected to be a novel type of medicaments useful against cell proliferation disorders, especially as carcinostatic agents. As for the PI3K inhibitor, wortmannin [H. Yano et al., J. Biol. Chem., 263, 16178 (1993)] and LY294002 [J. Vlahos et al., J. Biol. Chem., 269, 5241 (1994)] which is represented by the formula below are known. However, development of PI3K inhibitors having a more potent cancer cell growth inhibiting activity is desired.

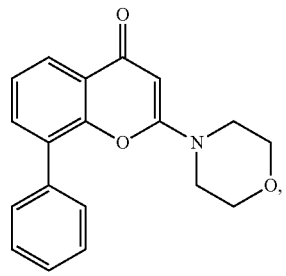

LY294002

Japanese Patent KOKAI (Laid-Open) No. 6-220059 discloses fused heteroaryl derivatives shown by formula (a) below which possess an activity of reducing the blood glucose level. Furthermore, compounds shown by formula (b) and formula (c) below are described in Indian J. Chem., Sect. B (1993), 32B (9), 965-8 and J. Heterocycl. Chem. (1992), 29 (7), 1693-702, respectively. In addition, Al-AzharBull. Sci. (1992), 3(2), 767-75 discloses a compound shown by formula (d) below. However, none of these prior art publications disclose or suggest the PI3K inhibiting activity.

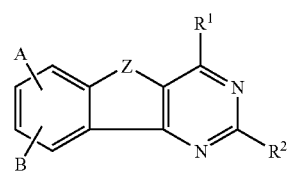

(a)

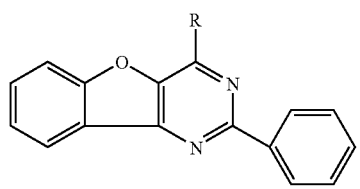

(b)

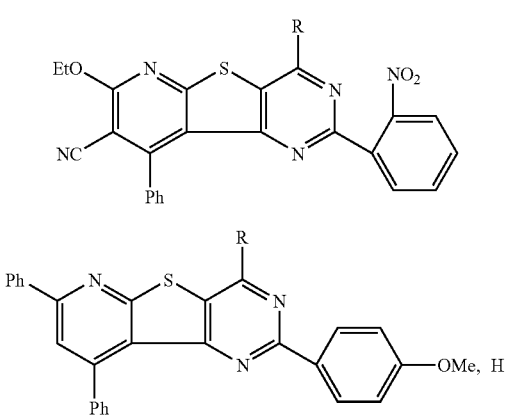

In formula (a) above, Z is O, S or =N—R0, R1 is an amino which may be substituted, a heterocyclic group which may be substituted, etc.; R2 is cyano, an amino which may be substituted, or a heterocyclic group which may be substituted; and with respect to the remaining substituents, see the specification of the patent. In formula (b) and (c) above, R is a (substituted) amino or a (substituted) nitrogen-containing saturated heterocyclic group.

Publication No. WO98/23613 discloses fused pyrimidine derivatives, such as 7H-pyrrolo[2,3-d]pyrimidine derivatives, which having a tyrosine kinase receptor inhibiting activity and which are useful as carcinostatic agents, wherein the fused pyrimidine derivatives have at its fourth position a particular-heteroaryl-substituted amino, phenyl-substituted amino, or indole-1-yl, and have no substituent at its second position.

Following compounds are known among the compounds shown by general formula (I), whereas "A" ring is a ring shown by (b);

(1) Ann. Pharm. Fr. (1974), 32(11), 575-9 discloses 4-(4-morpholinyl)-2-phenylpyrido[2,3-d]pyrimidine as a compound having antiinflammatory and spasmolytic activities, (2) Chem. Pharm. Bull. (1976), 24(9), 2057-77 discloses 4-(4-morpholinyl)-2-phenylpyrido[2,3-d]pyrimidine-7(1H)-one as a compound having a diuretic activity, (3) Khim.-Farm. Zh. (1993), 7(7), 16-19 and Khim. Geterotsiki. Soedin. (1971), 7(3), 418-20 disclose 4-(4-morpholinyl)-2-phenyl-6-quinazolinol and 6-methoxy-4-(4-morpholinyl)-2-phenylquinazoline as compounds having an antibiotic activity, (4) Publication No. WO2000/41697 discloses 2,4-diamino-6-phenyl-8-piperidinopyrimido[5,4-d]pyrimidine as a compound having cerebral ischemia prevention and treatment effects, (5) Publication No. WO99/32460 discloses, as cardiovascular drugs, compounds of general formula (Ib) described hereinafter wherein B is a benzene ring, W is N, n is 2 or 3, existing R1's are all —OMe, and R4b is an unsubstituted phenyl or a phenyl substituted by 1 to 3 substituents which are selected from -a halogen, NO2, -a lower alkyl, —O-a lower alkyl, -a halogenated lower alkyl and —CONRaRc, (6) Publication No. BE841669 discloses, as antiparasitics, compounds of general formula (Ib) described hereinafter wherein B is a benzene ring, W is N, n is 1, R1 is -a halogen or -a lower alkyl, and R4b is -(an imidazolyl which may have one or more substituents), (7) Publication No. WO99/43682 discloses, as antianxiety agents, compounds of general formula (Ib) described hereinafter wherein B is a thiophene ring, and W is CH, (8) Japanese Patents KOKAI (Laid-Open) Nos. 62-10085 and 61-158983 disclose compounds of general formula (Ib) described hereinafter wherein B is an imidazole ring, and W is N, whereas the compounds have an antiinflammatory activity, a platelet aggregation inhibiting activity, etc., (9) U.S. Pat. No. 3,873,545 and Act Pol. Pharm. (1994), 51(4-5), 359-63 disclose compounds of general formula (Ib) described hereinafter wherein B is a pyridine ring, and R4b is an unsubstituted phenyl, an unsubstituted pyridyl, or -a lower alkylene-(a nitrogen-containing saturated heterocyclic group which may have one or more substituents), whereas the compounds have a spasmolytic, diuretic or hypotensive activity,

(10) U.S. Pat. No. 2,940,972 discloses compounds of general formula (Ib) described hereinafter wherein B is a pyrazine ring, and R4b is an unsubstituted phenyl, or a benzyl, whereas the compounds have a coronary dilating or sedative activity,

(11) U.S. Pat. No. 3,753,981 and German Patent Publication No. 2,140,280 disclose compounds of general formula (Ib) described hereinafter wherein B is a benzene ring, and R4b is a styryl or 2-(5-nitro-2-furyl)vinyl, whereas the compounds have an antiinflammatory or antibiotic activity, and

(12) Eur. J. Med. Chem. (1996), 31(5), 417-425, discloses compounds of general formula (Ib) described hereinafter wherein B is a benzene ring, W is CH, and R2 and R3 are bonded together with an adjacent N atom to form -(piperidinyl which may have one or more substituents) or -(piperazinyl which may have one or more substituents), as compounds working as a benzodiazepine receptor ligand, U.S. Pat. No. 4,560,692 discloses them as those having a spasmolytic and ataractic activity, and Japanese Patents KOKAI (Laid-Open) No. 2-129169 discloses them as those having a lipoperoxidation inhibiting activity.

Furthermore, compounds of general formula (Ib) described hereinafter wherein B is a pyridine ring and n is 0 are disclosed in Japanese Patent KOKAI (Laid-Open) No. 51-138689 (antiparasitics), Japanese Patent KOKAI (Laid-Open) No. 56-120768 (a dye component for thermosensitive recording materials), Antimicrob. Agents Chemother., (1975), 8 (2), 216-19 (an antibacterial activity), Cancer Res. (1975), 35 (12), 3611-17 (a mutagenic activity), CA 64: 19608c, Collect. Czech. Chem. Commun., (1994), 59 (6), 1463-6, U.S. Pat. No. 5,304,554 (an anti-HIV activity), Chem. Pharm. Bull., (1982), 30(6), 1974-9, and J. Heterocycl. Chem. (1980), 17(5), 1029-34. However, none of the prior publications teach or even suggest the PI3K inhibiting activity and carcinostatic activity.

SUMMARY OF THE INVENTION

The present inventors have performed extensive investigations on compounds with a PI3K inhibiting activity. As a result, it has been found that novel fused heteroaryl derivatives have an excellent PI3K inhibiting activity as well as a cancer cell growth inhibiting activity. Based on the finding, it has been discovered that the fused heteroaryl derivatives could be excellent PI3K inhibitors and antitumor agents. The present invention has thus been achieved.

Therefore, the present invention relates to pharmaceutical compositions, which are PI3K inhibitors or antitumor agents, comprising a fused heteroaryl derivative represented by general formula (I) below or a salt thereof and a pharmaceutically acceptable carrier.

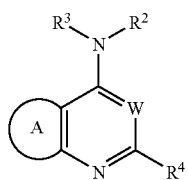

[wherein:

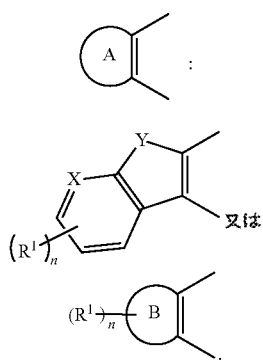

B represents a benzene ring, or a 5- or 6-membered monocyclic heteroaryl containing 1 to 2 hetero atoms selected from O, S and N;

R1 represents -a lower alkyl, -a lower alkenyl, -a lower alkynyl, -a cycloalkyl, -an aryl which may have one or more substituents, -a heteroaryl which may have one or more substituents, -a halogen, —NO2, —CN, -a halogenated lower alkyl, —ORb, —SRb, —SO2-Rb, —SO—Rb, —COORb, —CO—Rb, —CONRaRb, —SO2NRaRb, —NRaRb, —NRa—CORb, —NRa—SO2Rb, —O—CO—NRaRb or —NRaCO—COORb, —CO-a nitrogen-containing saturated heterocyclic group, —CONRa-a lower alkylene-ORb, —CONRa-a lower alkylene-NRb, —O-a lower alkylene-ORb, —O-a lower alkylene-O-a lower alkylene-ORb, —O-a lower alkylene-NRaRb, —O-a lower alkylene-O-a lower alkylene-NRaRb, —O-a lower alkylene-NRc-a lower alkylene-NRaRb, —NRc-a lower alkylene-NRaRb, —N(a lower alkylene-NRaRb)2, —CONRa—ORb, —NRa—CO—NRbRc, or —OCORb;

each of R2 and R3, which may be the same or different, represents —H, -a lower alkyl, -a lower alkylene-ORa or -a lower alkylene-NRaRc, or R2 and R3 are combined together with the N atom adjacent thereto to form a nitrogen-containing saturated heterocyclic group as —NR2R3 which may have one or more substituents;

each of Ra and Rc, which may be the same or different, represents —H or -a lower alkyl;

Rb represents —H, -a lower alkyl, a cycloalkyl, an aryl which may have one or more substituents or a heteroaryl which may have one or more substituents;

n represents 0, 1, 2 or 3;

each of W and X, which may be same or different, represents N or CH;

Y represents O, S or NH;

and,

R4 represents —H, -a lower alkyl, -a lower alkenyl, -a lower alkynyl, -(an aryl which may have one or more substituents), -a lower alkylene-(an aryl which may have one or more substituents), -a lower alkenylene-(an aryl which may have one or more substituents), -a lower alkynylene-(an aryl which may have one or more substituents), -(a cycloalkyl which may have one or more substituents), -(a cycloalkenyl which may have one or more substituents), -a lower alkylene-(a cycloalkyl which may have one or more substituents), -a lower alkenylene-(a cycloalkyl which may have one or more substituents), -a lower alkylene-(a nitrogen-containing saturated heterocyclic group which may have one or more substituents), -a lower alkenylene-(a nitrogen-containing saturated heterocyclic group which may have one or more substituents), -(a heteroaryl which may have one or more substituents), -a lower alkylene-(a heteroaryl which may have one or more substituents), or -a lower alkenylene-(a heteroaryl which may have one or more substituents). The same applies hereinbelow.

The compounds (I) of the present invention encompass the known compounds as well as commercially available compounds later described in Compound Z, which are all included within the definition of formula (I).

The present invention further relates to a novel fused heteroaryl derivative represented by general formula (Ia) or (Ib) or salts thereof, as well as a novel pharmaceutical composition comprising the same and a pharmaceutically acceptable carrier:

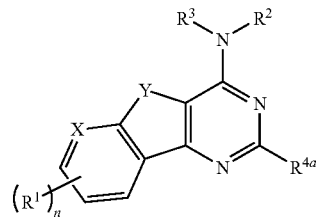

(Ia)
[wherein:

R1 represents -a lower alkyl, -a lower alkenyl, -a lower alkynyl, -a cycloalkyl, -an aryl which may have one or more substituents, -a heteroaryl which may have one or more substituents, -a halogen, —NO2, —CN, -a halogenated lower alkyl, —ORb, —SRb, —SO2-Rb, —SO—Rb, —COORb, —CO—Rb, —CONRaRb, —SO2NRaRb, —NRaRb, —NRa—CORb, —NRa—SO2Rb, —O—CO—NRaRb or —NRaCO—COORb, —CO-a nitrogen-containing saturated heterocyclic group, —CONRa-a lower alkyl-ORb, —CONRa-a lower alkylene-ORb, —O-a lower alkylene-NRb, —O-a lower alkylene-O-a lower alkylene-ORb, —O-a lower alkylene-NRaRb, —O-a lower alkylene-O-a lower alkylene-NRaRb, —O-a lower alkylene-NRc-a lower alkylene-NRaRb, —NRc-a lower alkylene-NRaRb, —N(a lower alkylene-NRaRb)2, —CONRa—ORb, —NRa—CO—NRbRc, or —OCORb;

each of R2 and R3, which may be the same or different, represents —H or -a lower alkyl, or R2 and R3 are combined together with the N atom adjacent thereto to form a nitrogen-containing saturated heterocyclic group as —NR2R3 which may have one or more substituents;

Ra and Rc, which may be the same or different, represent —H or -a lower alkyl;

Rb represents —H, -a lower alkyl, a cycloalkyl, an aryl which may have one or more substituents or a heteroaryl which may have one or more substituents;

n represents 0, 1, 2 or 3;

X represents N or CH;

Y represents O, S or NH;
and,
R4a represents -(an aryl which may have one or more substituents), -a lower alkylene-(an aryl which may have one or more substituents), -a lower alkenylene-(an aryl which may have one or more substituents), -a lower alkynylene-(an aryl which may have one or more substituents), -(a cycloalkyl which may have one or more substituents), -(a cycloalkenyl which may have one or more substituents), -a lower alkylene-(a cycloalkyl which may have one or more substituents), -a lower alkenylene-(a cycloalkyl which may have one or more substituents), -a lower alkylene-(a nitrogen-containing saturated heterocyclic group which may have one or more substituents), -a lower alkenylene-(a nitrogen-containing saturated heterocyclic group which may have one or more substituents), -(a heteroaryl which may have one or more substituents), lower alkylene-(a heteroaryl which may have one or more substituents), or -a lower alkenylene-(a heteroaryl which may have one or more substituents);
with the proviso that the following compounds are excluded:
(1) compounds in which X represents N, Y represents S, n is 3 and R1 represents a combination of —CN, —OEt and phenyl, and R4a represents 2-nitrophenyl;
(2) compounds in which X represents CH, and R4a represents -(a heteroaryl which may have one or more substituents);
(3) compounds in which X represents CH, Y represents O, n is 0 and R4a represents an unsubstituted phenyl; and
(4) compounds in which X represents N, Y represents S, n is 2, R1 represents an unsubstituted phenyl and R4a represents 4-methoxyphenyl or an unsubstituted phenyl. The same applies hereinbelow.

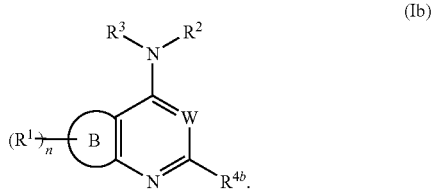

(Ib)

[wherein:
B represents a benzene ring, or a 5- or 6-membered monocyclic heteroaryl containing 1 to 2 hetero atoms selected from O, S and N;
R1 represents -a lower alkyl, -a lower alkenyl, -a lower alkynyl, -a cycloalkyl, -an aryl which may have one or more substituents, -a heteroaryl which may have one or more substituents, -a halogen, —NO2, —CN, -a halogenated lower alkyl, —ORb, —SRb, —SO2-Rb, —SO—Rb, —COORb, —CO—Rb, —CONRaRb, —SO2NRaRb, —NRaRb, —NRa—CORb, —NRa—SO2Rb, —O—CO—NRaRb, —NRaCO—COORb, —NRaCOORb, —NRaCO-a lower alkylene-an aryl, —NRa—SO2-a lower alkylene-an aryl, —NRa-a lower alkylene-an aryl, -a lower alkylene-ORb, -a lower alkylene-NRaRb, —CO-a nitrogen-containing saturated heterocyclic group, —CONRa-a lower alkylene-ORb, —CONRa-a lower alkylene-NRcRb, —CONRa-a lower alkylene-a nitrogen-containing saturated heterocyclic group, —O-a lower alkylene-ORb, —O-a lower alkylene-NRaRb, —O-a lower alkylene-a nitrogen-containing saturated heterocyclic group, —O-a lower alkylene-O-a lower alkylene-ORb, —O-a lower alkylene-O-a lower alkylene-NRaRb, —O-a lower alkylene-NRc-a lower alkylene-NRaRb, —NRc-a lower alkylene-NRaRb, —N(a lower alkylene-NRaRb)2, —CONRa—ORb, —NRa—CO—NRbRc, or —OCORb;
R2 and R3 are combined together with the N atom adjacent thereto to form —NR2R3 which is a nitrogen-containing saturated heterocyclic group which may have one or more substituents;
Ra and Rc, which may be the same or different, represent —H or -a lower alkyl;
Rb represents —H, -a lower alkyl, -a cycloalkyl, -(an aryl which may have one or more substituents) or -(a heteroaryl which may have one or more substituents);
n represents 0, 1, 2 or 3, whereas n represents 1, 2 or 3 when B represents a benzene ring;
W represents N or CH;
and,
R4b represents -(an aryl which may have one or more substituents), -a lower alkylene-(an aryl which may have one or more substituents), -a lower alkenylene-(an aryl which may have one or more substituents), -a lower alkynylene-(an aryl which may have one or more substituents), -(a cycloalkyl which may have one or more substituents), -(a cycloalkenyl which may have one or more substituents), -a lower alkylene-(a cycloalkyl which may have one or more substituents), -a lower alkenylene-(a cycloalkyl which may have one or more substituents), -a lower alkylene-(a nitrogen-containing saturated heterocyclic group which may have one or more substituents), -a lower alkenylene-(a nitrogen-containing saturated heterocyclic group which may have one or more substituents), -(a heteroaryl which may have one or more substituents), -a lower alkylene-(a heteroaryl which may have one or more substituents), or -a lower alkenylene-(a heteroaryl which may have one or more substituents);
with the proviso that the following compounds are excluded:
(1) 4-(4-morpholinyl)-2-phenylpyrido[2,3-d]pyrimidine,
(2) 4-(4-morpholinyl)-2-phenylpyrido[2,3-d]pyrimidin-7(1H)-one,
(3) 4-(4-morpholinyl)-2-phenyl-6-quinazolinol and 6-methoxy-4-(4-morpholinyl)-2-phenyquinazoline,
(4) 2,4-diamino-6-phenyl-8-piperidinopyrimido[5,4-d]pyrimidine,
(5) compounds in which B represents a benzene ring, W represents N, n is 2 or 3, existing R1's all represent —OMe, and R4b is an unsubstituted phenyl or a phenyl which is substituted by 1 to 3 substituents selected from -halogen, —NO2, -a lower alkyl, —O-a lower alkyl, -a halogenated lower alkyl and —CONRaRc,
(6) compounds in which B represents a benzene ring, W represents N, n is 1, R1 represents -halogen or -a lower alkyl, and R4b represents -(imidazolyl which may have one or more substituents),
(7) compounds in which B represents a thiophene ring, and W represents CH,
(8) compounds in which B represents an imidazole ring, and W represents N,
(9) compounds in which B represents a pyridine ring, and R4b represents an unsubstituted phenyl, an unsubstituted pyridyl, or -a lower alkylene-(a nitrogen-containing saturated heterocyclic group which may have one or more substituents),
(10) compounds in which B represents a pyrazine ring, and R4b represents an unsubstituted phenyl, or a benzyl,
(11) compounds in which B represents a benzene ring, and R4b represents a styryl or 2-(5-nitro-2-furyl)vinyl, and
(12) compounds in which B represents a benzene ring, W represents CH, and R2 and R3 are combined together with the N atom adjacent thereto to form -(piperidinyl which may have one or more substituents) or -(piperazinyl which may have one or more substituents). The same applies hereinbelow.

Further teaching of the present invention provides a method to treat disorders (especially cancers) which are associated with PI3K, wherein the method comprises of administering to a patient an effective amount of a fused heteroaryl derivative of formula (I), (Ia) or (Ib) above or a salt thereof as well as a use of said fused heteroaryl derivative or a salt thereof for producing a medicament (especially a carcinostatic agent) which inhibit PI3K.

EMBODIMENTS

The compounds of general formula (I), (Ia) or (Ib) are described below in more detail.

The term "lower" throughout the specification is used to mean a straight or branched hydrocarbon chain having 1 to 10, preferably 1 to 6, and more preferably 1 to 3 carbon atoms.

Preferred examples of the "lower alkyl" are an alkyl having 1 to 3 carbon atoms, more preferably methyl and ethyl. Preferred examples of the "lower alkenyl" include vinyl, allyl, 1-propenyl, isopropenyl, 1-butenyl, 2-butenyl and 3-butenyl. Preferred examples of the "lower alkynyl" include ethynyl, 1-propynyl, 2-propynyl, 1-butyryl, 2-butynyl, 3-butynyl and 1-methyl-2-propynyl. The terms "lower alkylene", "lower alkenylene" and "lower alkynylene" are used to mean bivalent groups of the lower alkyl, lower alkenyl and lower alkynyl described above. Preferred examples of these groups are methylene, ethylene, vinylene, propenylene, ethynylene and propynylene. The terms "cycloalkyl" and "cycloalkenyl" refer to cycloalkyl and cycloalkenyl groups preferably having 3 to 8 carbon atoms. Preferred examples of these groups include cyclopropyl, cyclopentyl, cyclohexyl and cyclopentenyl.

Examples of the "halogen" are F, Cl, Br and I. Examples of the "halogenated lower alkyl" are the aforementioned lower alkyl groups which are further substituted with one or more halogen atoms described above, preferably —CF3.

The term "nitrogen-containing saturated heterocyclic group" throughout the specification refers to a 5- to 7-membered heterocyclic group containing one or two nitrogen atoms on the ring, which may further contain one O or S atom and may form a bridge structure or may be fused with one benzene ring. Preferred examples of such heterocyclic group are pyrrolidinyl, piperazinyl, piperidyl and morpholinyl. Preferred examples of the nitrogen-containing saturated heterocyclic group as —NR2R3 are 1-pyrrolidinyl, 1-piperazinyl, piperidino and morpholino, with particular preference to morpholino.

The term "aryl" is used throughout the specification to mean an aromatic cyclic hydrocarbon group. An aryl having 6 to 14 carbon atoms is preferable. Preferred examples of such aryl are phenyl and naphthyl.

The term "heteroaryl" refers to a 5- or 6-membered monocyclic heteroaryl containing 1 to 4 hetero atoms selected from N, S and O as well as a bicyclic heteroaryl fused to a benzene ring. The heteroaryl may be partially saturated. Preferred examples of the monocyclic heteroaryl are furyl, thienyl, pyrrolyl, imidazolyl, pyrazolyl, thiazolyl, isothiazolyl, oxazolyl, triazolyl, tetrazolyl, pyridyl, pyrimidinyl, pyridazinyl and pyrazinyl. Examples of the bicyclic heteroaryl are preferably benzofuranyl, benzothienyl, benzothiadiazolyl, benzothiazolyl, benzimidazolyl, indolyl, isoindolyl, indazolyl, quinolyl, isoquinolyl, cinnolinyl, quinazolinyl, quinoxalinyl and benzodioxolyl. Specific examples of the partially saturated heteroaryl are 1,2,3,4-tetrahydroquinolyl, etc. Particularly preferred are 5- to 6-membered monocyclic groups, more preferably imidazolyl, thiazolyl, triazolyl, pyridyl and pyrazinyl.

Examples of a "5- or 6-membered monocyclic heteroaryl containing 1 or 2 hetero atoms selected from O, S and N" in B include a furan, thiophene, pyrrole, imidazole, pyrazole, thiazole, isothiazole, oxazole, pyridine, pyrimidine, pyridazine and pyrazine ring. Preferably, it is a pyridine, pyrazine or thiophene ring. More preferable, it is a pyridine ring.

The substituents for the "aryl which may have one or more substituents", "heteroaryl which may have one or more substituents", "cycloalkyl which may have one or more substituents", "cycloalkenyl which may have one or more substituents" or "nitrogen-containing saturated heterocyclic group which may have one or more substituents" are 1~5 substituents, which may be the same or different. Preferably, these substituents are selected from Group A described below. Each of R, R' and R", which may be the same or different, represents H or a lower alkyl (the same shall apply hereinafter).

Group A: -a lower alkyl, -a lower alkenyl, -a lower alkynyl, -a halogen, -a halogenated lower alkyl, -a lower alkylene-OR, —NO2, —CN, =O, —OR, —O— a halogenated lower alkyl, —O-a lower alkylene-NRR', —O-a lower alkylene-OR, —O-a lower alkylene-an aryl, —SR, —SO2-a lower alkyl, —SO-a lower alkyl, —COOR, —COO-a lower alkylene-an aryl, —COP, —CO-an aryl, -an aryl, —CONRR', —SO2NRR', —NRR', —NR"-a lower alkylene-NRR', —NR'-a lower alkylene-OR, —NR-a lower alkylene-an aryl, —NRCO-a lower alkyl, —NRSO2-a lower alkyl, -a cycloalkyl and -a cycloalkenyl.

When R4, R4a and R4b represent "an aryl which may have one or more substituents" or "a heteroaryl which may have one or more substituents", the substituents are 1 to 5 groups selected from a) through c) below, which may be the same or different.

a): -a lower alkyl, -a lower alkenyl, -a lower alkynyl, -a halogen, -a halogenated lower alkyl, -a lower alkylene-OR, —NO2, —CN, =O, —O-halogenated lower alkyl, —SO2-a lower alkyl, —SO-a lower alkyl, —COOR, —COO-a lower alkylene-an aryl, —COR, —CO-an aryl, —SO2NRR', -Cyc or -Alp-Cyc (wherein Alp represents a lower alkylene, a lower alkenylene or a lower alkynylene, and Cyc represents an aryl which may have 1 to 5 substituents selected from Group A, a heteroaryl which may have 1 to 5 substituents selected from Group A, a nitrogen-containing saturated heterocyclic group which may have 1 to 5 substituents selected from Group A, a cycloalkyl which may have 1 to 5 substituents selected from Group A, or a cycloalkenyl which may have 1 to 5 substituents selected from Group A; the same shall apply hereinafter).

b): —NR-E-F (wherein E represents —CO—, —COO—, —CONR'—, —SO2NR'— or —SO2-; F represents -Cyc or -(a lower alkyl, a lower alkenyl or a lower alkynyl which may be substituted by one or more substituents selected from the group comprising of -a halogen, —NO2, —CN, —OR, —O-a lower alkylene-NRR', —O-a lower alkylene-OR, —SR, —SO2-a lower alkyl, —SO-a lower alkyl, —COOR, —COR, —CO-an aryl, —CONRR', —SO2NRR', —NRCO-a lower alkyl, —NRR', —NR'-a lower alkylene-OR, —NR"-a lower alkylene-NRR' and -Cyc); and the same shall apply hereinafter).

c): —Z—R', —Z-Cyc, —Z-Alp-Cyc, —Z-Alp-Z'—R' or —Z-Alp-Z'-Cyc (wherein each of Z and V, which may be the same or different, independently represents O, S or NR; and the same shall apply hereinafter).

The particularly preferred ones are -a lower alkylene-OR, —CONRR', —NR—CO-Cyc1 (wherein Cyc1 is -an aryl which may have 1~5 substituents selected from Group A, -a heteroaryl which may have 1~5 substituents selected from Group A, or -a nitrogen-containing saturated heterocyclic group which may have 1~5 substituents selected from Group A, and the same applies hereinbelow), —NR—SO2-Cyc1, —OR, —NRR', —O-a lower alkylene-NRR' and —O-a lower alkylene-(a nitrogen-containing saturated ring which may have 1~5 substituents selected from Group A).

When n is 2 to 4, each R1 group may be the same or different, independently.

In the compounds which are shown by formulas (I), (Ia) and (Ib) of the present invention, the following compounds are preferred:

(1) Compounds in which R2 and R3 forms —NR2R3 which is a nitrogen-containing saturated heterocyclic group which may have 1~2 substituents selected from the group comprising of —OH, and -a lower alkyl;

(2) Compounds in which R2 and R3 forms —NR2R3 which is -morpholino;

(3) Compounds in which W is N;

(4) Compounds in which R4, R4a or R4b represents -(an aryl which may have one or more substituents) or -(a heteroaryl which may have one or more substituents);

(5) Compounds in which B represents a benzene ring; R1 represents -a lower alkyl, -a lower alkenyl, -a lower alkynyl, -a cycloalkyl, -an aryl which may have one or more substituents, -a heteroaryl which may have one or more substituents, -a halogen, —NO2, —CN, -a halogenated lower alkyl, —ORb, —SRb, —SO2-Rb, —SO—Rb, —COORb, —CO—Rb, —CONRaRb, —SO2NRaRb, —NRaRb, —NRa—CORb, —NRa—SO2Rb, —O—CO—NRaRb or —NRaCO—COORb;

(6) Compounds in which B is a pyridine, pyrazine or thiophene ring and n is 0;

(7) Compounds in which X represents N, Y represents O and n is 0; and (8) Compounds in which R4, R4a or R4b represents an aryl which has one or more substituents selected from the group comprising of -a lower alkylene-OR, —CONRR', —NR—CO-Cyc1, —NR—SO2-Cyc1, —OR, —NRR', —O-a lower alkylene-NRR' and —O-a lower alkylene-(a nitrogen-containing saturated heterocyclic group which may have 1~5 substituents selected from Group A).

The particularly preferred compounds shown by general formula (Ia) are those having R4a which is a phenyl having at least one substituent which is selected from of the group comprising of —OH, —NH2, —NH-a lower alkyl, —N(a lower alkyl)2, —O-a lower alkylene-NH2 and —O-a lower alkylene-(a nitrogen-containing saturated heterocyclic group which may be substituted by a lower alkyl).

Moreover, the following compounds shown by general formula (Ib) are particularly preferred:

(1) Compounds in which W represents N, R4b represents -(an aryl which may have one or more substituents), and R2 and R3 form —NR2R3 which is -morpholino;

(2) Compounds in which B represents a benzene ring, n is 1 or 2, and R1 represents -a halogen, —NO2, —CN, -a halogenated lower alkyl, —ORb, —SRb, —NRaRb, —NRa—CORb or —NRa—SO2Rb, and (3) Compounds in which B represents a pyridine, pyrazine or thiophene ring, n is 0, and R4b represents a phenyl which has at least one substituent which is selected from —OH, —CH2OH and —CONH2.

Among the compounds of the present invention, the preferred ones which are shown by general formula (La) are (Co 17) 6-amino-3'-(4-morpholinopyrido[3',2':4,5]furo[3,2-d]pyrimidin-2-yl)nicotinanilide, (Co 33) 4-(4-morpholinopyrido[3',2':4,5]furo[3,2-d]pyrimidin-2-yl)aniline, (Co 50) 3-(4-morpholinopyrido[3',2':4,5]furo[3,2-d]pyrimidin-2-yl)phenol, (Co 69) 4-morpholino-2-[3-(2-piperazin-1-ylethoxy)phenyl]pyrido[3',2':4,5]furo[3,2-d]pyrimidine, (Co 73) 3'-(4-morpholinopyrido[3',2':4,5]furo[3,2-d]pyrimidin-2-yl)acrylanilide, and salts thereof. The preferred ones which are shown by general formula (Ib) are (Co 144) N-[2-(3-benzenesulfonylaminophenyl)-4-morphoniloquinazolin-6-yl]acetamide, (Co 164) 3-(4-morpholinopyrido[4,3-d]pyrimidin-2-yl)phenol, (Co 172) 3-(4-morpholinopyrido[3,2-d]pyrimidin-2-yl)phenol, (Co 174) 3-(4-morpholinopyrido[3,4-d]pyrimidin-2-yl)phenol, (Co 186) 3-(6-methoxy-4-morpholinoquinazolin-2-yl)phenol, (Co 190) 3-(4-morpholinothieno[3,2-d]pyrimidin-2-yl)phenol, (Co 191) 3-(4-morpholinopteridin-2-yl)phenol, and salts thereof.

The compound of this invention may exist in the form of geometrical isomers or tautomers depending on the kinds of substituent groups, and these isomers in separated forms or mixtures thereof are included in the present invention. Also, the compound of the present invention may have asymmetric carbon atoms, so that optical isomer forms may exist based on such carbon atoms. All of the mixtures and the isolated forms of these optical isomers are included in the present invention.

Some of the compounds of the invention may form salts. There is no particular limitation so long as the formed salts are pharmacologically acceptable. Specific examples of acid salts are salts with inorganic acids such as hydrochloric acid, hydrobromic acid, hydroiodic acid, sulfuric acid, nitric acid, phosphoric acid, etc., organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid, etc. Specific examples of basic salts include salts with inorganic bases containing metals such as sodium, potassium, magnesium, calcium, aluminum, etc., or salts with organic bases such as methylamine, ethylamine, ethanolamine, lysine, ornithine, etc. In addition, various hydrates and solvates and polymorphism of the compound (I), (Ia) or (Ib) and salts thereof are also included in this invention.

(Processes for Producing Compounds)

Hereinafter representative processes for producing the compounds of the present, invention are described below. In these processes, functional groups present in the starting materials or intermediates may be suitably protected with protective groups, depending upon the kinds of functional groups. In view of the preparation technique, it may be advantageous to protect the functional groups with groups that can be readily reverted to the original functional groups. When required, the protective groups are removed to give the desired products. Examples of such functional groups are amino, hydroxy, carboxyl, etc. Examples of the protective groups which may be used to protect these functional groups are shown in, e.g., Greene and Wuts, "Protective Groups in Organic Synthesis", second edition. These protective groups may be appropriately employed depending upon reaction conditions.

Production Method 1

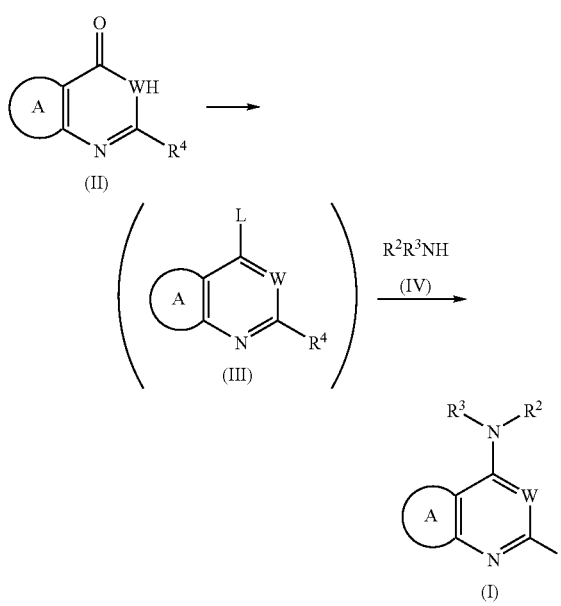

(Here and hereinafter, L represents a leaving group.)

This process for producing the compounds (I) of the present invention comprises converting the compounds shown by general formula (II) to reactive derivatives thereof (III) in a conventional manner and then reacting an amine (IV) with the reactive derivatives. When another reactive site containing the leaving group L also exists on the ring A or the substituent R4 in the reactive derivatives (III), the same or different amine (IV) may be reacted again, if necessary. In a similar manner, when the A ring or R4 of the compounds of the present invention has a leaving group L such as a chloro or fluoro, transformations of functional groups may be conducted such as a hydrolysis reaction according to a method described in J. Am. Chem. Soc., 68, 1288 (1946) or an ipso-substitution reaction using alkoxide as a reacting agent according to a method described in Tetrahedron Lett., 40, 675 (1999).

The leaving group shown by L is preferably a halogen, or an organic sulfonyloxy group, e.g., methanesulfonyloxy, p-toluenesulfonyloxy, etc.

The reaction for preparing the reactive derivatives (III) can be carried out by the usual procedures. Where the leaving group is chlorine, phosphorus oxychloride, oxalyl chloride or thionyl chloride can be reacted under cooling or heating or at room temperature in an inert organic solvent or without. As such an inert organic solvent, there is an aromatic hydrocarbon solvent such as benzene or toluene; an ethereal solvent such as tetrahydrofuran (THF-), 1,4'-dioxane, etc.; a halogenated hydrocarbon solvent such as dichloromethane, chloroform, etc.; and a basic solvent such as pyridine or collidine. These solvents may be used alone or as a mixture of two or more. The solvent is optionally selected depending on the kinds of starting compounds. The addition of a base (preferably a dialkylaniline, triethylamine, ammonia, lutidine, collidine, etc.), phosphorus chloride (e.g., phosphorus pentachloride), a quaternary ammonium salt (e.g., tetraethylammonium chloride), or an N,N-dialkylamide compound (e.g., dimethylformamide (DMF)) may be advantageous in some cases from the viewpoint of accelerating the reaction. Where the leaving group is sulfonyloxy, the active intermediates (III) can be synthesized from the corresponding sulfonyl chloride by the usual procedures, e.g., using a method described in Tetrahedron Lett. 23 (22), 2253 (1982) or Tetrahedron Lett. 27 (34), 4047 (1986).

The reaction for producing the compounds (I) from the reactive derivatives (111) and the amine (IV) can be carried out by reacting the amine (IV) in an inert organic solvent or in the absence of any solvents under cooling or heating or at room temperature. The solvent described above is available and it may be used singly or as a mixture of two or more. The addition of an inorganic base such as sodium hydride, or an organic base such as triethylamine (TEA), pyridine or 2,6-lutidine, may be advantageous in some cases from the viewpoint of accelerating the reaction

Production Method 2

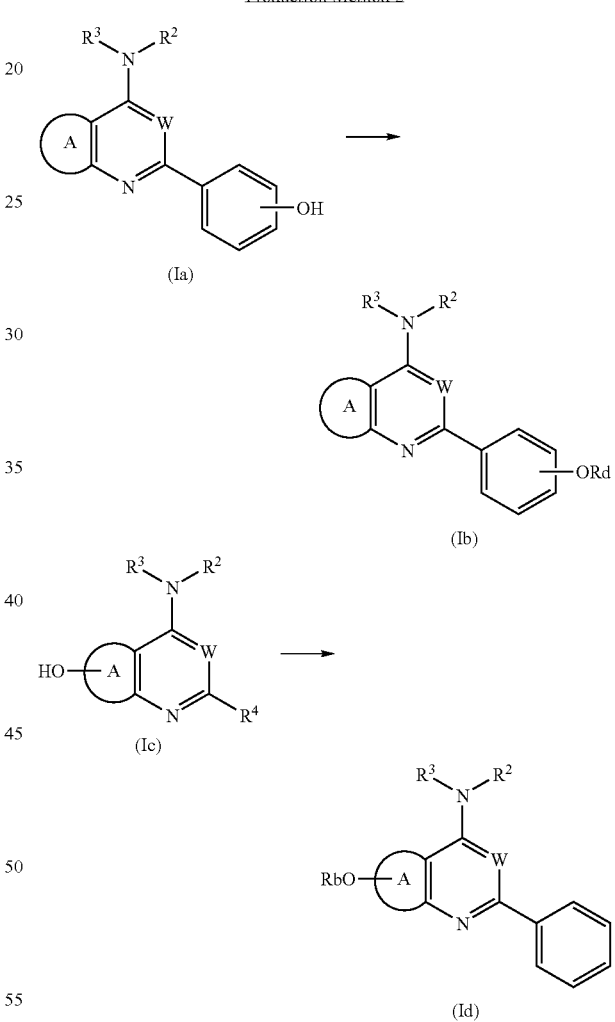

(Wherein Rd is a lower alkyl which may have one or more substituents and Rb has the same definition as defined above; and the same shall apply hereinafter.)

This process comprises O-alkylation of the hydroxy-substituted compounds shown by general formula (Ia) or (Ic) in a conventional manner to obtain the compounds (Ib) or (Id). The reaction may be carried out, e.g., by reacting the compounds (Ia) or (Ic) with an alkylating agent such as an alkyl halide or a sulfonic acid ester in the presence of a base such as triethylamine, potassium carbonate, sodium carbonate, cesium carbonate, sodium hydroxide, sodium hydride or potassium t-butoxide. The reaction temperature can be under cooling or heating or at room temperature and can be appropriately chosen depending on the kinds of starting compounds. When water is used or contained as a solvent in an O-alkylation reaction, the reaction may be accelerated by the addition of a phase transfer catalyst such as tetra n-butylammonium hydrogensulfate.

Another method for the O-alkylation reaction is Mitsunobu reaction. For example, methods described in Synthesis, 1 (1981) or modified methods may be used. For the hydroxyethylation of a hydroxyl group, methods using carbonate ester such as [1,3]dioxolane-2-one are also effective. As an example, methods described in J. Am. Chem. Soc., 68, 781 (1946) can be used.

Moreover, when functional groups exist on Rb and Rd of the compounds (Ib) and (Id) of the present invention, known reactions may be employed to convert the functional group. For example, when a hydroxyl group is present on Rb and Rd, the aforementioned O-alkylation reaction can be conducted, and when a leaving group is present such as a halogen, an appropriate alcohol or amine can be reacted with utilizing the conditions of said O-alkylation or N-alkylation described hereinafter in Production Method 4. When an ester group is present, the functional group can be converted to a carboxylic acid, hydroxymethyl group, and amido, using a method described hereinafter in Production Method 3.

The starting compounds (Ia) and (Ic) used in this process can be prepared by the method described for Production Method 1, using starting compounds whose OH group has been protected by an acyl type protective group (e.g., acetyl or tosyl). Further, when phosphorus oxychloride is used as a reacting agent for synthesizing reactive derivatives (III) and then a desired amino is reacted to synthesize (I), protective groups for OH group may be removed and O-phosphoramides may be produced, depending on the kind of starting compounds, a protective group, reaction conditions and conditions for work-up. In that case, for example, using a method described in Chem. Pharm. Bull., 37, 2564 (1989), phosphoramides groups can be removed. Other general protective groups can be introduced and removed by the methods described in "Protective Groups in Organic Synthesis" supra.

Production Method 3

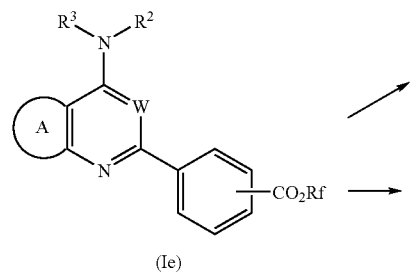

(Ie)

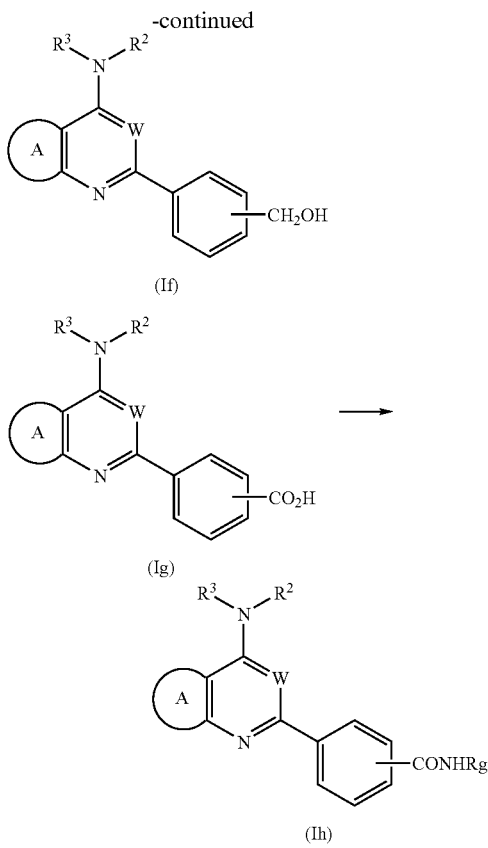

(Wherein Rf is a lower alkyl and Rg is a lower alkyl which may have one or more substituents; and the same shall apply hereinafter.)

Production Method 3 comprises transformations of the functional groups of the ester compounds of the present invention shown by general formula (Ie) to produce the hydroxymethyl compounds (If), carboxylic acid derivatives (Ig) and amide derivatives (Ih) of the present invention, respectively. Each of the reactions can be carried out in a conventional manner, e.g., as described in Jikken Kagaku Kouza (Encyclopedia for Experimental Chemistry) edited by Nihon Kagaku Kai (Japanese Association of Chemistry) and published by Maruzen Co., Ltd., and "Protective Groups in Organic Synthesis" supra.

Preferably, the reduction to give the hydroxymethyl compounds (If) can be conducted in an inert organic solvent to the reactions, e.g., an ethereal solvent or an aromatic hydrocarbon solvent, using a reducing agent such as lithium aluminum hydride, lithium borohydride, zinc borohydride, boran, Vitride, etc. The hydrolysis to give the carboxylic acid derivatives (Ik) can be conducted by reacting with lithium hydroxide, sodium hydroxide or potassium hydroxide in a single solvent selected from methanol, ethanol, THF and water, or a mixture of two or more. The amidation to give the amide compounds (Ih) may be performed by converting carboxylic acids to reactive derivatives such as acyl halides (acyl chlorides, etc.) or acid anhydrides, and then reacting the reactive derivatives with amines. In the reaction with amines, it is preferred to conduct the reaction in an inert organic solvent in the presence of a base (an inorganic base such as sodium hydroxide, or an organic base such as TEA, diisopropylethylamine or pyridine). Furthermore, the amidation using the carboxylic acid as a starting compound can also be carried out in an inert organic solvent in the presence of a condensation agent such as (1-ethyl-3-(3-dimethylaminopropyl) carbodiimide (EDCI), 1,1'-carbonylbis-1H-imidazole (CDI), etc.). In this case, an additive such as 1-hydroxybenzotriazol (HOBt) or the like may also be added to the reaction. The reaction temperature and solvent can be appropriately chosen depending on the kinds or the like of starting compounds.

corresponding urea, conversion to the corresponding carbamic acid, imidation or conversion to the corresponding thiazoles, to give the compounds (Ik), (Im), (In), (Io), (Ip), (Iq) and (Ir), respectively. These products can be appropriately subjected to further known modification reactions such as N-alkylation, if necessary.

Production Method 4

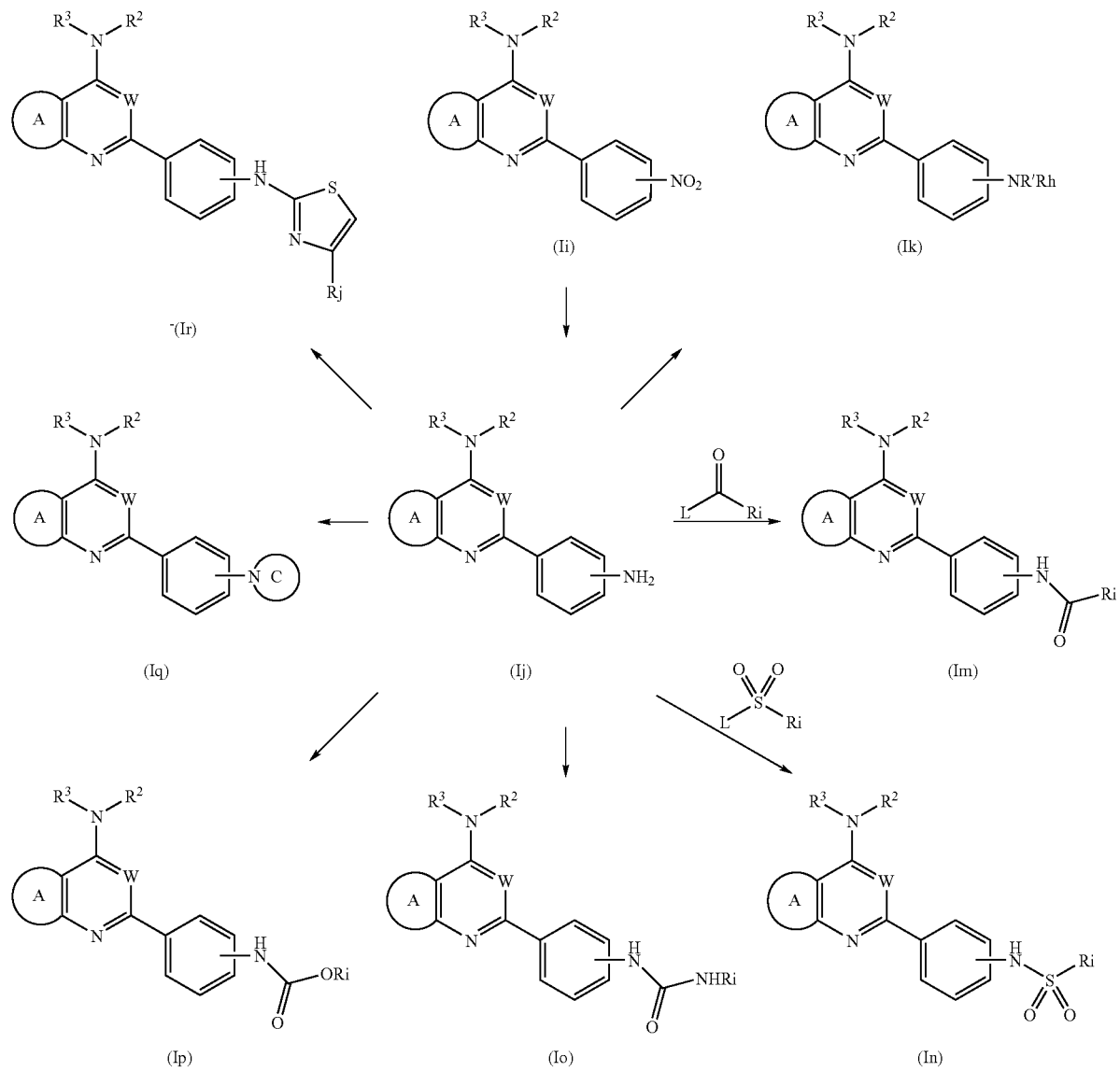

(Wherein R' has the same definition as defined above, Rh is -a lower alkyl which may have one or more substituents, Ri is -Cyc or -Alp which may have one or more substituents, a C ring is a nitrogen-containing saturated heterocyclic group which may have one or more substituents, and Rj is —H, -a lower alkyl, -an aryl, etc.; and the same shall apply hereinafter.)

Production Method 4 comprises the reduction of the nitro compounds shown by general formula (II) to the corresponding amino compounds (Ij) and then subjecting the amino compounds (Ij) to various modification reactions including N-alkylation, amidation, sulfonamidation, conversion to the These reactions can all be carried out in a conventional manner, e.g., using the methods described in "Jikken Kagaku Kouza" supra, or "Protective Groups in Organic Synthesis" supra. Preferred procedures in these methods are described below.

The reduction of the nitro compounds can be carried out in an alcoholic solvent such as methanol in a gaseous hydrogen atmosphere using palladium on carbon (Pd—C).

When various aldehydes are employed as the starting compounds, the N-alkylation can be conducted by reductive amination using aldehydes and reducing agents such as sodium borohydride, sodium triacetoxyborohydride or sodium cyanoborohydride. Reducing amination using Dean-Stark apparatus could be useful, too. When an alkyl halide such as methyl iodide or benzyl bromide, or dimethyl sulfate is employed as an alkylating agent, the reaction can be carried out in an inert organic solvent, e.g., DMF, acetonitrile or toluene, in the presence of base such as potassium carbonate, sodium hydroxide or sodium hydride, under cooling or heating or at room temperature. For monoalkylation, an example of useful procedure is as follows: protection of amino group by acyl group such as trifluoroacetyl, alkylation of acylamide by conventional methods using halogenated alkyl, and removal of protection. The dialkylation can be conducted by reacting 2 equivalents or more of a halogenated alkyl. For dimethylation, the reaction with formalin in formic acid at room temperature or under heating is also useful.

The conversion to the corresponding aminothiazole compounds can be conducted by converting the amino compounds to the corresponding thiourea derivatives and then reacting the derivatives with an α-halogenated ketone. Compounds (Ij) can be converted into the thiourea derivatives by methods described in, e.g., Synth. Commun. 1998, 28 (8), 1451; 1. Org. Chem., 1984, 49 (6), 997, Org. Synth., 1963, IV, 180; J. Am. Chem. Soc., 1934, 56, 1408, etc. The conversion of the thiourea derivatives into the thiazole derivatives can be conducted by reacting the thiourea derivatives with the α-halogenated ketone in an alcoholic solvent such as ethanol or a carbonyl solvent such as methyl ethyl ketone, under cooling or heating or at room temperature. The addition of a base (potassium carbonate, sodium carbonate, etc.) may be effective in some cases from the viewpoint of accelerating the reaction.

Production Method 5

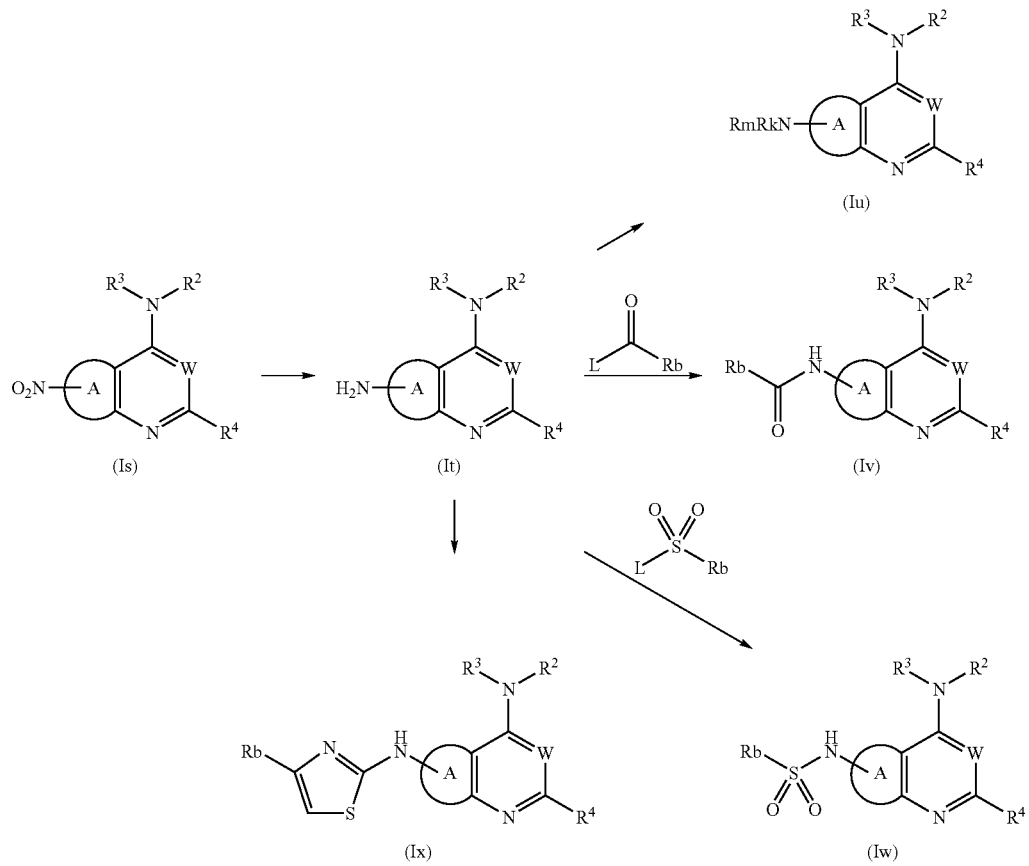

The amidation reaction may be performed in a similar manner to that described above for Production Method 3. The sulfonamidation can be carried out in an inert organic solvent using a reactive derivative such as an acid halide (acid chloride, etc.) or an acid anhydride. The conversion to the corresponding urea can be conducted by reacting with isocyanates in an inert organic solvent, e.g., an aromatic hydrocarbon solvent, under cooling or heating or at room temperature. The conversion to the corresponding carbamic acids can be conducted by reacting chloroformate derivatives in an inert organic solvent under cooling or heating or at room temperature. The imidation can be carried out using agents such as succinic anhydride or maleic anhydride.

(Wherein Rk and Rm each represents -a lower alkyl which may have one or more substituents.)

Production Method 5 comprises converting the nitro compounds of the invention shown by general formula (Is) to the corresponding amino compounds (It) and then subjecting them to various modification reactions to obtain the other compounds of the present invention. Each reaction can be carried out as described for Production Method 4.

Other Production Method

Other compounds included in the present invention can be obtained in the same manner as described above or by using methods well known to those skilled in the art. For instance, the reactions are carried out appropriately using methods described in "Jikken Kagaku Kouza" supra, or "Protective Groups in Organic Synthesis" supra.

For example, the demethylation reaction of compounds with an aryl group into the corresponding phenol derivatives can be carried out by the methods described in "Protective Groups in Organic Synthesis" supra, i.e., the method of reacting with a demethylating agent such as sodium cyanide or potassium cyanide in a solvent such as dimethylsulfoxide (DMSO), etc., at room temperature or under heating.

Processes for Preparing Starting Compounds

The starting compounds (II) for the synthesis of the present invention can be performed in conventional manners, e.g., by the reactions shown in the following synthetic routes.

(Wherein Rn is a lower alkyl; and the same shall apply hereinafter.)

The starting compounds (IIc) can be synthesized by a cyclization reaction of amide intermediates (5) or cyclization conducted by reacting anthranylic acid derivatives (1) as the starting compounds with imidates (6). Conventional cyclization reactions for preparing pyrimidine ring are available for the cyclization reaction for this purpose. For instance, the method described in Chem. Pharm. Bull., 39 (2), 352 (1991) can be used for the cyclization of the intermediates (5) and the intermediates (1) and (6) as the starting materials can be cyclized by the method described in J. Med. Chem., 9, 408 (1966). The amide intermediates (5) can be synthesized by amidation of the aniline derivatives (4) in a conventional manner, or by sequential conversions of esterification of a carboxylic acid in (1), acylation of an amino, and amidation of the ester group according to conventional methods. For example, the amide intermediates (5) can be obtained in accordance with the methods described in J. Med. Chem., 33, 1722 (1990), Eur. J. Med. Chem.-Chim. Ther., 9(3), 305 (1974), etc. When (3) is obtained by acylation using (2) as the starting materials, diacylation may take place depending on the starting compounds and reaction conditions. In such a case, treatment with basic conditions will give desired monoacyl compounds (3).

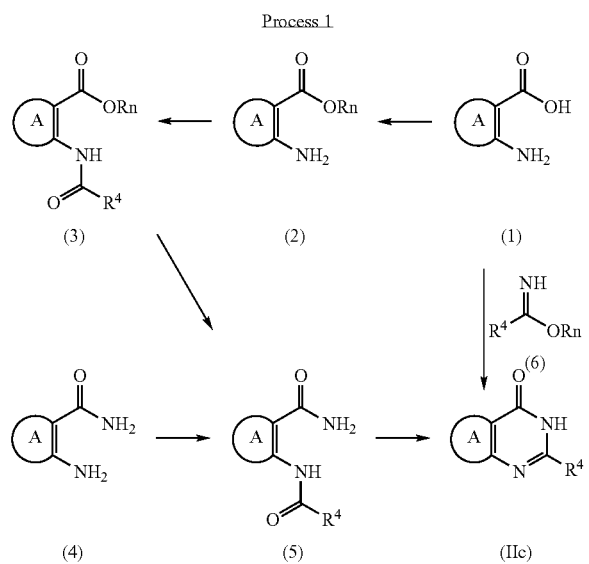

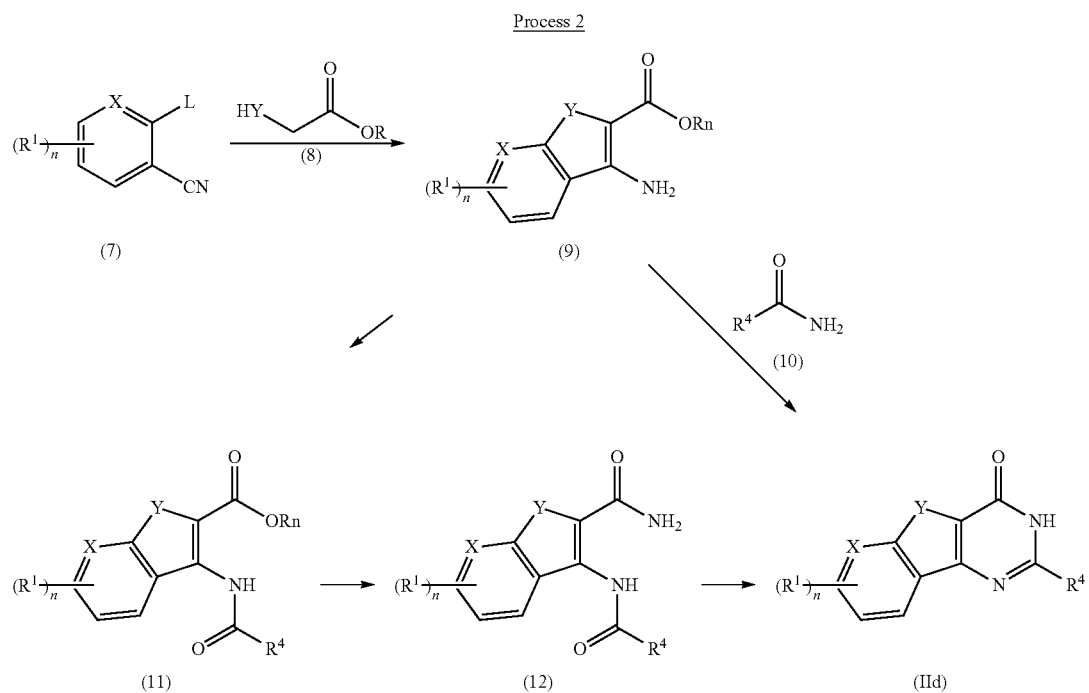

The starting compounds (IId) can be synthesized by cyclization of the amide intermediates (12) or by cyclization of the ester intermediates (7) and the amide compounds (10). The intermediates (12) can be cyclized in the same manner as described above; where the intermediates (7) and (10) are used as the starting compounds, the cyclization can be carried out by the method described in, e.g., J. Med. Chem., 37, 2106 (1994). The amide intermediates (12) can be prepared by conversion of the functional group in ester compounds (7) in a conventional manner. The bicyclic ester intermediates (9) can be synthesized by formation of a 5-membered ring by reacting nitrile compounds (7) with ester compounds (8) in the presence of a base, for example, in accordance with the method described in J. Org. Chem., 37, 3224 (1972) or J. Heterocycl. Chem., 11 (6), 975 (1974), etc.

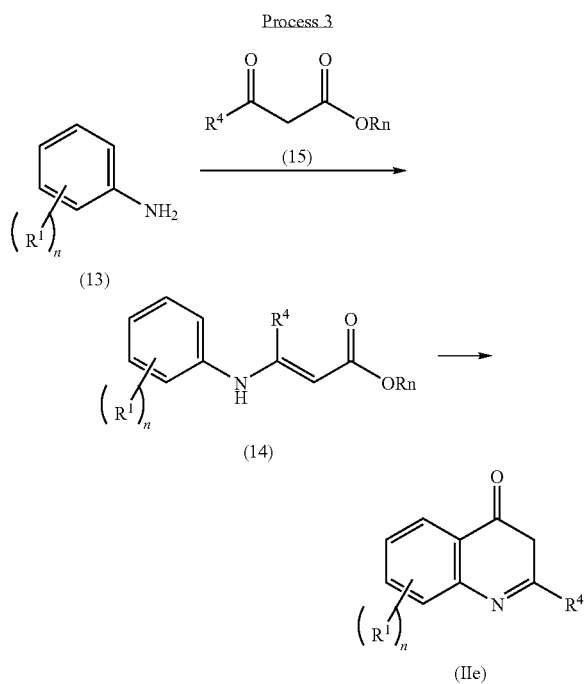

The starting compounds (IIe) can be synthesized, e.g., by cyclization of the starting compounds (14). Preferably, the compounds (14) are heated in a solvent with a high boiling point such as diphenyl ether or in the absence of any solvents. The starting compounds (14) can be synthesized in a conventional manner, e.g., by condensation of the corresponding anilines (13) with the compounds (15).

Each of the reaction products obtained by the aforementioned production methods is isolated and purified as a free base or a salt thereof. The salt can be produced by a usual salt forming method. The isolation and purification are carried out by employing usually used chemical techniques such as extraction, concentration, evaporation, crystallization, filtration, recrystallization, various types of chromatography and the like.

Various forms of isomers can be isolated by the usual procedures making use of physicochemical differences among isomers. For instance, racemic compounds can be separated by means of a conventional optical resolution method (e.g., by forming diastereomer salts with a conventional optically active acid such as tartaric acid, etc. and then optically resolving the salts) to give optically pure isomers. A mixture of diastereomers can be separated by conventional means, e.g., fractional crystallization or chromatography. In addition, an optical isomer can also be synthesized from an appropriate optically active starting compound.

INDUSTRIAL APPLICABILITY

The compounds of the present invention exhibit a PI3K inhibitory activity and therefore, can be utilized in order to inhibit abnormal cell growths in which PI3K plays a role. Thus, the compounds are effective in the treatment of disorders with which abnormal cell growth actions of PI3K are associated, such as restenosis, atherosclerosis, bone disorders, arthritis, diabetic retinopathy, psoriasis, benign prostatic hypertrophy, atherosclerosis, inflammation, angiogenesis immunological disorders, pancreatitis, kidney disease, cancer, etc. In particular, the compounds of the present invention possess excellent cancer cell growth inhibiting effects and are effective in treating cancers, preferably all types of solid cancers and malignant lymphomas, and especially, leukemia, skin cancer, bladder cancer, breast cancer, uterus cancer, ovary cancer, prostate cancer, lung cancer, colon cancer, pancreas cancer, renal cancer, gastric cancer, brain tumor, etc.

The pharmacological effect of the compounds according to the invention have been verified by the following pharmacological tests.

Test Example 1

Inhibition of PI3K (p110α Subtype)

Inhibition was determined using enzyme (bovine p110α) prepared in the baculovirus expression system. Bovine p110 was prepared according to a modification from the method by I. Hiles et al., Cell, 70, 419 (1992). Each compound to be assayed was dissolved in DMSO and the obtained 10 mM DMSO solution was serially diluted with DMSO.

The compound (0:5 µl) to be assayed and enzyme were mixed in 25 µl of buffer solution (40 mM Tris-HCl (pH 7.4), 200 mM NaCl, 2 mM dithiothreitol, 5 mM MgCl2). Then, 25 µl of 5 mM Tris-HCl (pH 7.4) buffered solution supplemented with 10 µg PI (Sigma), 2µ Ci [γ-32P] ATP (Amersham Pharmacia) and 80 µM non-radiolabeled ATP (Sigma) was added to the mixture to initiate the reaction. After reacting at 37° C. for 15 minutes, 200 µl of 1M HCl and 400 µl of CHCl3/MeOH (1:1) were added to the reaction mixture. The resulting mixture was stirred and then centrifuged. After the organic layer was again extracted twice with 150 µl of MeOH/1M HCl (1:1). The radioactivity was measured using Cerenkov light.

The IC50 inhibition activity was defined by a 50% inhibition concentration of each compound assayed, which was converted from the radioactivity determined as 100% when DMSO alone was added and as 0% when no enzyme was added.

The compounds of the prevent invention exhibited an excellent p110α subtype inhibition activity. For example, 1050 of Compound (hereinafter, abbreviated as Co) 10, Co 17, and Co 24 were less than 1 µM.

Moreover, compounds of the prevent invention were confirmed to have inhibiting activities against other subtypes (such as a C2 β subtype).

Test Example 2

Colon Cancer Cell Growth Inhibition

HCT116 cells from a colon cancer cell line were cultured in McCoy's 5A medium (GIBCO) supplemented with 10% fetal bovine serum. HCT116 cells were inoculated on a 96 well plate (5000 cells/well) followed by overnight incubation. The test compound diluted with the medium was added to the medium in a final concentration of 0.1 to 30M (final DMSO concentration, 1%). After incubation over 72 hours, Alamar Blue reagent was added to the medium. Two hours after the addition, a ratio of fluorescent intensity at an excitation wavelength of 530 nm to that at an emission wavelength of 590 nm was measured to determine the IC50. Co 14, Co 24, Co 25, Co 31, Co 46 and Co 47 of the present invention exerted an excellent cancer cell growth inhibition activity.

Test Example 3

Melanoma Cell Growth Inhibition

A375 cells from a melanoma cell line were cultured in DMEM medium (GIBCO) supplemented with 10% fetal bovine serum. A375 cells at 10,000 cells/100 µl were added to a 96 well plate which contained 1 µl/well of the test compounds (final concentration of 0.001~30 µM). After incubation for over 46 hours, Alamar Blue reagent was added to the medium (10 µl/well). Two hours after the addition, a ratio of fluorescent intensity at an excitation wavelength of 530 nm to that at an emission wavelength of 590 nm was measured to determine the IC50 of the test compounds in the same manner as in the above examples.

The compounds of the prevent invention exhibited an excellent cancer cell growth inhibition activity. For example, Co17, Co 33, Co 50, Co 69, Co 164, Co 172, Co 174, Co 186, Co 190 and Co 191 exerted a good melanoma cell growth inhibition activity. Their IC50 values were 0.33~4.26 µM. Contrarily, the known PI3K inhibitor LY294002 showed a value of 8.39 µM.

In addition to the above cancer cell lines, the compounds of the present invention exhibited excellent cancer cell growth inhibiting activities against Hela cells from a cervix cancer cell line, A549, H460 cells from a lung cancer cell line, COLO205, WiDr, Lovo cells from a colon cancer cell line, PC3, LNCap cells from a prostate cancer cell line, SKOV-3, OVCAR-3, CHI cells from an ovary cancer cell line, 087 MG cells from a glioma cell line and BxPC-3 cells from a pancreas cancer cell line.

Test Example 4

In Vivo Cancer Cell Growth Inhibition

A single-cell suspension of HelaS3 ($5\times10^6$ cells), a human cervix cancer cell line, was inoculated into the flank of female Balb/c nude mice by subcutaneously injection. When the tumor reached 100~200 mm3 in volume, test compounds were intraperitoneally administered once a day for two weeks. 20% Hydroxypropyl-β-cyclodextrin/saline was intraperitoneally administered with the same schedule as a control group. The diameter of the tumors was measured with a vernier caliper at certain time intervals until one day after the final doze administration. The tumor volume was calculated by the following formula: ½×(a shorter diameter)2×(a longer diameter).

In the present test, test compounds exhibited superior antitumor activities as compared with the control group.

The pharmaceutical composition of the present invention can be prepared in a conventional manner by mixing one or more compounds of the invention shown by general formula (I) with a carrier for medical use, a filler and other additives usually used in pharmaceutical preparation. The pharmaceutical composition of the invention may be administered either orally in the form of tablets, pills, capsules, granules, powders, liquid, etc., or parenterally such as by intravenous or intramuscular injection, in the form of suppositories, or through pernasal, permucosal or subcutaneous route.

For oral administration of the composition in the present invention, a solid composition in the form of, e.g., tablets, powders or granules is available. In such a solid composition, one or more active or effective ingredients are blended with at least one inert diluent such as lactose, mannitol, glucose, hydroxypropyl cellulose, microcrystalline cellulose, starch, polyvinyl pyrrolidone or magnesium aluminate metasilicate. The composition may further contain additives other than the inert diluent by the usual procedures. Examples of such additives include a lubricant such as magnesium stearate, a disintegrating agent such as calcium cellulose glycolate, a solubilization assisting agent such as glutamic acid or aspartic acid. Tablets or pills may be coated, if necessary, with films of sugar or a gastric or enteric substance such as sucrose, gelatin, hydroxypropyl cellulose, hydroxypropylmethyl cellulose phthalate, etc.

A liquid composition for oral administration includes pharmaceutically acceptable emulsions, solutions, suspensions, syrups, elixirs, etc. and contains an inert diluent conventionally employed, e.g., purified water or ethanol. In addition to the inert diluent above, the liquid composition may further contain an auxiliary agent such as a moistening agent or a suspending agent, a sweetener, a flavor and/or a preservative.

A composition for parenteral administration contains a sterile aqueous or non-aqueous solution, a suspension and an emulsion. Examples of the aqueous solution and suspension include distilled water for injection use and physiological saline. Typical examples of the non-aqueous solution and suspension are propylene glycol, polyethylene glycol, vegetable oil such as olive oil, an alcohol such as ethanol, polysorbate 80, and the like. These compositions may further contain a preservative, a moistening agent, an emulsifier, a dispersing agent, a stabilizer and a solubilization assisting agent. These compositions are sterilized, e.g., by filtering them through a bacteria retention filter, incorporating a bactericide or through irradiation. Alternatively, they may be prepared into a sterile solid composition, which is dissolved in sterile water or a sterile solvent for injection prior to use.

In the case of oral administration, suitable daily does is usually about 0.0001 to 50 mg/kg body weight, preferably about 0.001 to 10 mg/kg, more preferably about 0.01 to 1 mg/kg, and the daily does is administered once a day or divided into 2 to 4 doses per day. In the case of intravenous injection, suitable daily dose is usually about 0.0001 to 1 mg/kg body weight, preferably about 0.0001 to 0.1 mg/kg. And the daily does is administered once a day or divided into a plurality of doses per day. The dose may be appropriately determined for each case, depending on conditions, age, sex, etc.

The compounds of the present invention can be utilized alone, or in conjunction with other treatments (e.g., radiotherapy and surgery). Moreover, they can be utilized in conjunction with other antitumor agents, such as alkylation agents (cisplatin, carboplatin, etc.), antimetabolites (methotrexate, 5-FU, etc.), antitumor antibiotics (adriamycin, bleomycin, etc.), antitumor vegetable alkaloids (taxol, etoposide, etc.), antitumor hormones (dexamethasone, tamoxifen, etc.), antitumor immunological agents (interferon α, β, γ, etc.), and so forth.

EXAMPLES

The present invention will be described in more detail by referring to the following EXAMPLES but is not deemed to be limited thereto.

The following Tables 1~3 and 13~16 show starting compounds which were used in EXAMPLES, and Tables 4~11 and 17~24 show structural formulas as well as physicochemical properties of the compounds of the present invention. Moreover, the compounds of the present invention with structural formulas shown in Tables 12 and 25~26 can be easily produced in the same manner as in the EXAMPLES mentioned hereinafter or in accordance with the Production Methods mentioned hereinabove, or by applying thereto some modifications which are obvious to those skilled in the art.

In the tables, abbreviations are used to mean the following.
Rco: starting compounds number
Rex: Production method of Reference Example compounds (a following number represents a Reference Example number described hereinafter, indicating that the compound was prepared using the method described in the Reference Example or the one similar thereto.)
Co: compounds number of the present invention
Str: structural formula
Sal: salt
Syn: production method (a following number represents a number of an EXAMPLE described hereinbelow, indicating that the associated compound is produced using the method described in the EXAMPLE or a similar method.)
Dat: physicochemical properties wherein:
F: FAB-MS (M+H)+
FN: FAB-MS (M−H)−
E: EI-MS
M: melting point [° C.]
(dec.): Decomposition
N1: characteristic peaks δ ppm of NMR (DMSO-d6, TMS internal standard)
Ac: acetyl
Bn: benzyl
Ph: phenyl
Ts: 4-toluenesulfonyl
Ms: methanesulfonyl
Me: methyl
Et: ethyl Where two or more positions to permit substitution are present, the position substituted is indicated as a prefix (e.g., 6-MeO-7-HO represents 6-methoxy-7-hydroxy.).

TABLE 1

| Rco | Rex | Str | DAT |
|---|---|---|---|
| 1 | 1 | 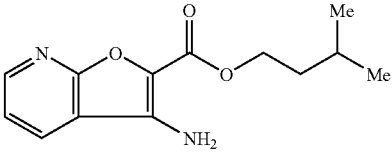 | F: 249 |
| 2 | 1 | 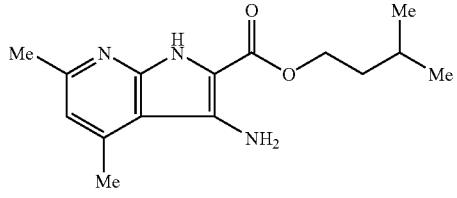 | F: 277 |
| 3 | 2 | 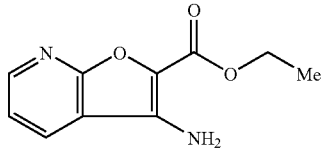 | F: 206 |
| 4 | 3 | 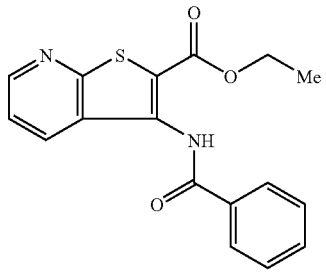 | F: 327 |

TABLE 1-continued
| Rco | Rex | Str | DAT |
|---|---|---|---|
| 5 | 3 | 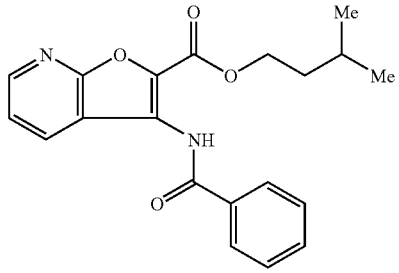 | F: 353 |
| 6 | 3 | 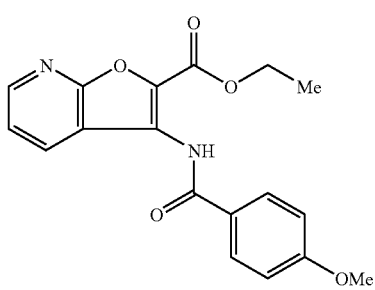 | F: 341 |
| 7 | 3 | 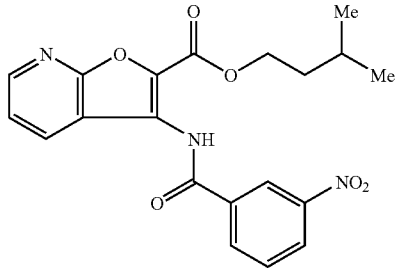 | F: 398 |
| 8 | 3 | 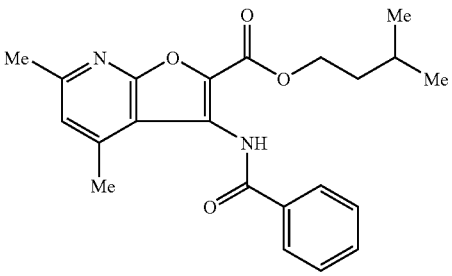 | F: 381 |
| 9 | 3 | 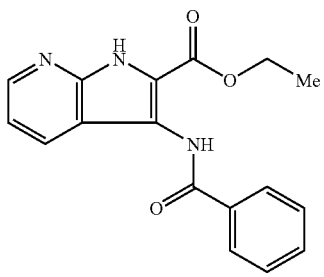 | F: 310 |

TABLE 1-continued
| Rco | Rex | Str | DAT |
|---|---|---|---|
| 10 | 3 | 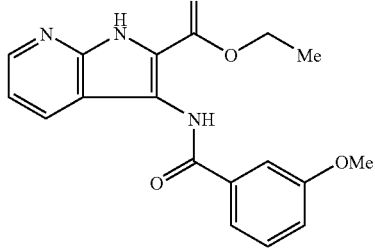 | F: 341 |
| 11 | 4 | 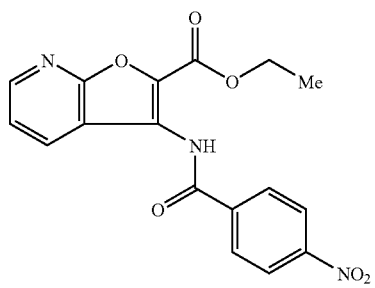 | F: 356 |
| 12 | 4 | 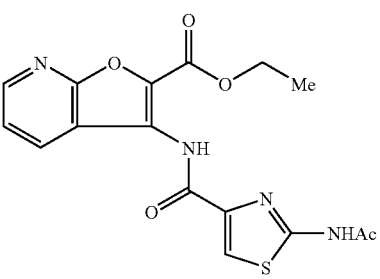 | F: 375 |
| 13 | 5 | 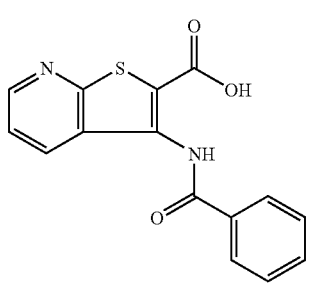 | F: 299 |
| 14 | 5 | 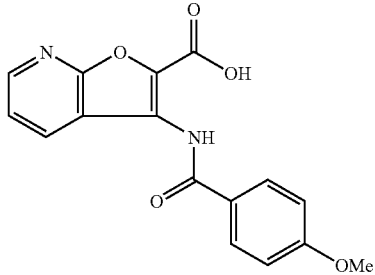 | FN: 311 |

TABLE 1-continued
| Rco | Rex | Str | DAT |
|---|---|---|---|
| 15 | 5 | 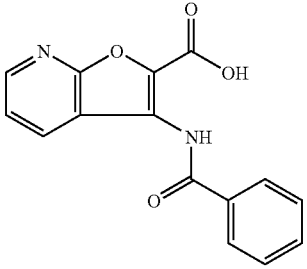 | FN: 281 |
| 16 | 5 | 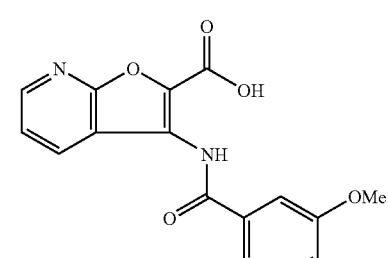 | FN: 311 |
TABLE 2
| Rco | Rex | Str | DAT |
|---|---|---|---|
| 17 | 5 | 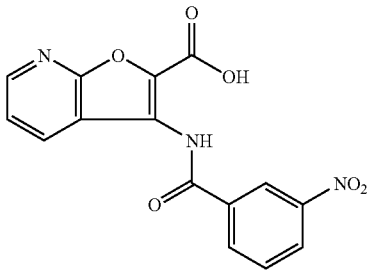 | FN: 326 |
| 18 | 5 | 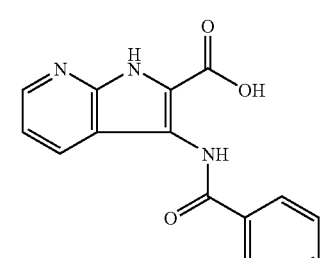 | F: 282 |
| 19 | 5 | 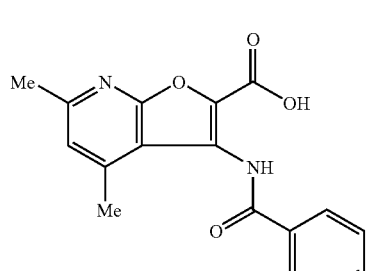 | F: 311 |
TABLE 2-continued
| Rco | Rex | Str | DAT |
|---|---|---|---|
| 20 | 5 | 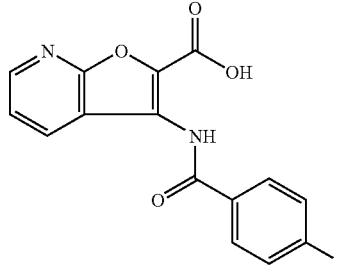 | FN: 326 |
| 21 | 6 | 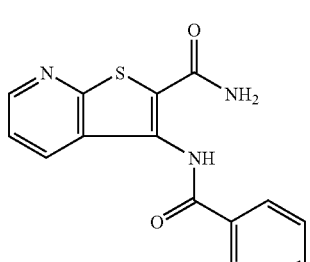 | F: 298 |
| 22 | 6 | 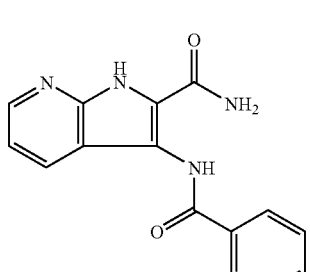 | FN: 279 |

TABLE 2-continued
| Rco | Rex | Str | DAT |
|---|---|---|---|
| 23 | 6 | 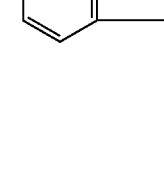 | FN: 325 |
| 24 | 6 | 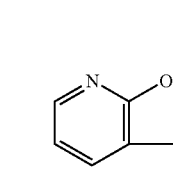 | F: 282 |
| 25 | 6 |  | F: 310 |
| 26 | 6 | 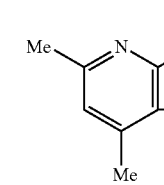 | F: 312 |
| 27 | 6 |  | F: 312 |
TABLE 2-continued
| Rco | Rex | Str | DAT |
|---|---|---|---|
| 28 | 6 | 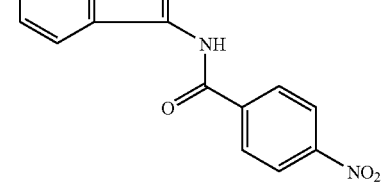 | FN: 325 |
| 29 | 7 | 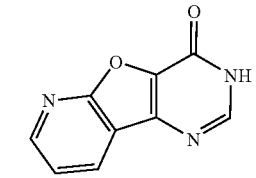 | F: 188 |
| 30 | 8 | 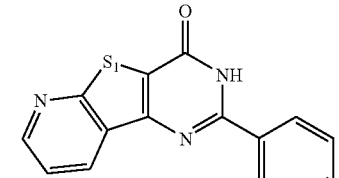 | E: 279 |
| 31 | 8 | 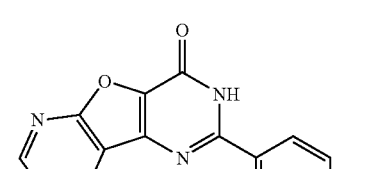 | E: 308 |
| 32 | 8 | 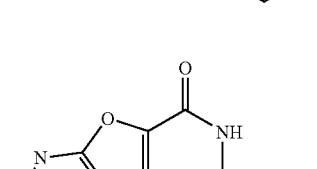 | F: 264 |
TABLE 3
| Rco | Rex | Str | DAT |
|---|---|---|---|
| 33 | 8 | 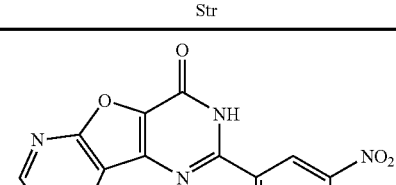 | F: 309 |

TABLE 3-continued

| Rco | Rex | Str | DAT |
|---|---|---|---|
| 34 | 8 | | F: 292 |
| 35 | 8 | | F: 263 |
| 36 | 8 | | F: 294 |
| 37 | 8 | | E: 293 |
| 38 | 9 | | F: 322 |
| 39 | 9 | | E: 321 |
| 40 | 3 | | F: 341 |
| 41 | 4 | | FN: 344 |
| 42 | 5 | | FN: 311 |
| 43 | 5 | | FN: 316 |
| 44 | 6 | | F: 312 |
| 45 | 6 | | F: 317 |

TABLE 3-continued
| Rco | Rex | Str | DAT |
|---|---|---|---|
| 46 | 8 | 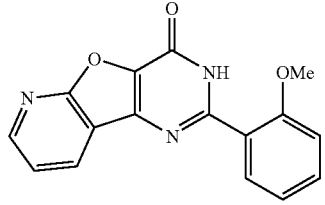 | F: 293 |
| 47 | 8 | 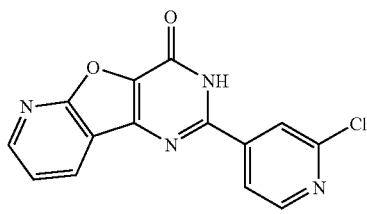 | FN: 297 |
| 48 | 9 | 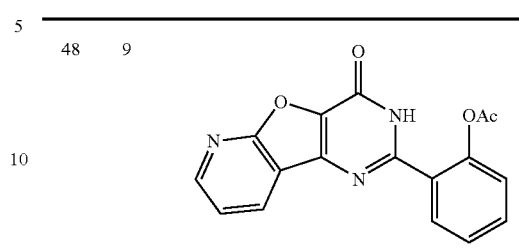 | F: 322 |
| 49 | 19 | 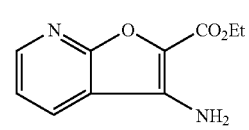 | F: 207 |
TABLE 4
| Co | Syn | Str | DAT |
|---|---|---|---|
| 1 | 1 | 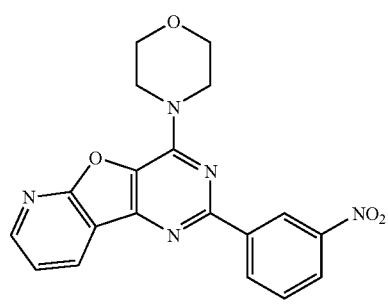 | F: 378 |
| 2 | 1 | 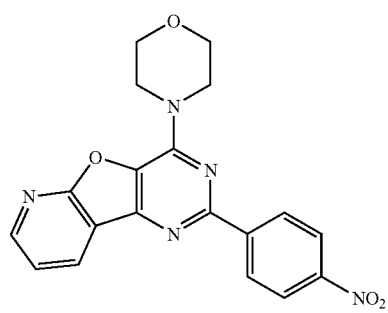 | E: 377 |
| 3 | 2 | 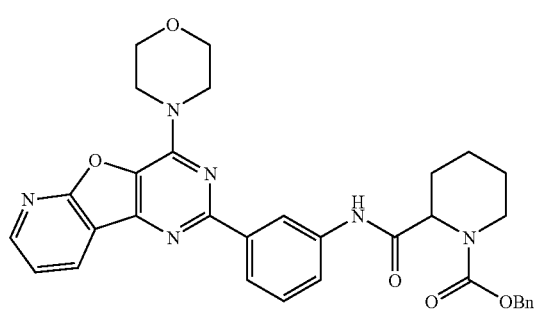 | F: 593 |

TABLE 4-continued
| Co | Syn | Str | DAT |
|---|---|---|---|
| 4 | 2 | 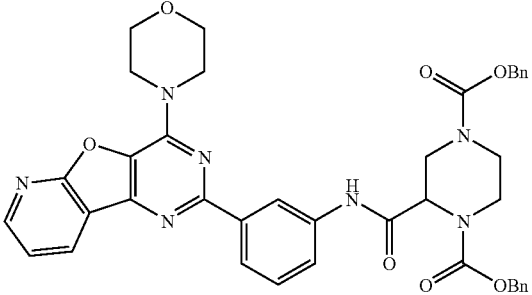 | N1: 4.15 (4H, t, J = 4.4 Hz), 8.52 (1H, s), 10.41 (1H, s). |
| 5 | 2 | 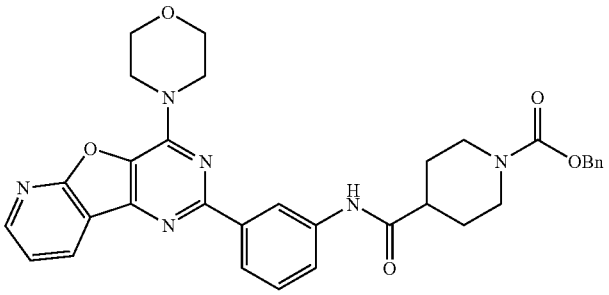 | F: 593 |
| 6 | 2 | 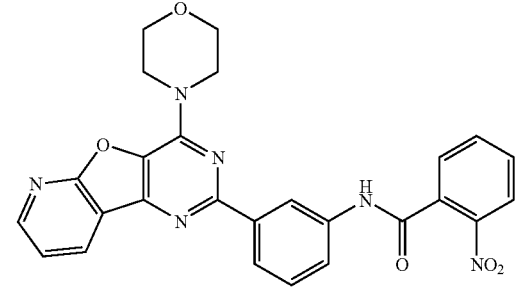 | F: 497 |
| 7 | 12 | 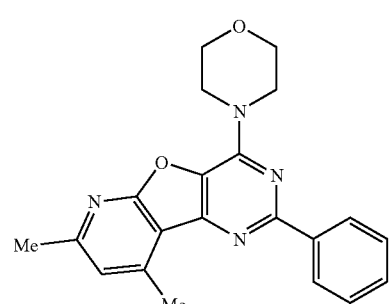 | M: 206-208 |
| Z | — | 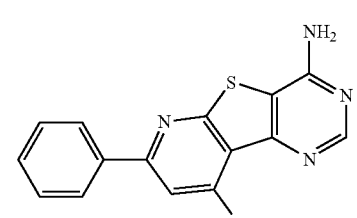 | 市販品: SPECS and BioSPECS B.V 社製 ( カタログ番号: AE-848/3855062) |

TABLE 5

(Ia)

| Co | Syn | X | Y | NR²R³ | R⁴ | Sal | DAT |
|----|-----|---|---|-------|-----|-----|-----|
| 8  | 3 | N | O | 4-methylmorpholine | 3-(PhSO₂NH)phenyl | — | M: 229-230; N1: 3.85 (4H, t, J = 4.8 Hz), 7.22-7.25 (1H, m), 10.47 (1H, s) |
| 9  | 3 | N | O | 4-methylmorpholine | 3-[(2-methyl-5-nitrophenyl)sulfonylamino]phenyl | — | M: 291-293; N1: 2.74 (3H, s), 7.39 (1H, t, J = 7.8 Hz), 8.23 (1H, s) |
| 10 | 4 | N | O | 4-methylmorpholine | 3-(pyridine-2-carboxamido)phenyl | — | M: 266-268; N1: 3.87 (4H, t, J = 4.8 Hz), 7.51 (1H, t, J = 7.8 Hz), 10.78 1H, s) |
| 11 | 4 | N | O | 4-methylmorpholine | 3-(6-chloropyridine-3-carboxamido)phenyl | — | F: 487 |
| 12 | 5 | N | O | 4-methylmorpholine | 3-(3-hydroxypyridine-2-carboxamido)phenyl | HCl | N1: 3.87 (4H, t, J = 4.8 Hz), 8.87 (1H, s), 11.06 (1H, s) |
| 13 | 5 | N | O | 4-methylmorpholine | 3-(pyrazine-2-carboxamido)phenyl | HCl | N1: 3.88 (4H, t, J = 4.8 Hz), 9.34 (1H, s), 10.88 (1H, s) |
| 14 | 5 | N | O | 4-methylmorpholine | 3-(2-aminothiazole-4-carboxamido)phenyl | 2HCl | N1: 3.86 (4H, t, J = 4.8 Hz), 8.14 (1H, s), 10.85 (1H, s) |

TABLE 5-continued (Ia)

| Co | Syn | X | Y | NR²R³ | R⁴ | Sal | DAT |
|----|-----|---|---|-------|-----|-----|-----|
| 15 | 5 | N | O | 4-methylmorpholine | N-(3-methylphenyl)-1H-imidazole-4-carboxamide | 2HCl | N1: 3.87 (4H, t, J = 4.4 Hz), 7.56 (1H, t, J = 7.8 Hz), 11.26 (1H, s) |
| 16 | 5 | N | O | 4-methylmorpholine | 5-amino-N-(3-methylphenyl)-1H-1,2,4-triazole-3-carboxamide | HCl | N1: 3.87 (4H, t, J = 4.4 Hz), 8.84 (1H, s), 10.72 (1H, s) |
| 17 | 5 | N | O | 4-methylmorpholine | 6-amino-N-(3-methylphenyl)pyridine-3-carboxamide | 2HCl | M: 203-207; N1: 3.86 (4H, t, J = 4.9 Hz), 7.52 (1H, t, J = 7.8 Hz), 10.71 (1H, s) |
| 18 | 5 | N | O | 4-methylmorpholine | 1-benzyloxycarbonyl-N-(3-methylphenyl)piperidine-3-carboxamide | — | N1: 1.35-1.48 (1H, m), 3.85 (4H, t, J = 4.4 Hz), 10.19 (1H, s) |

TABLE 6

| Co | Syn | X | Y | NR²R³ | R⁴ | Sal | DAT |
|----|-----|---|---|-------|-----|-----|-----|
| 19 | 5 | N | O | 4-methylmorpholine | 3-(diethylamino)-N-(3-methylphenyl)propanamide | 2HCl | M: 203-206 |
| 20 | 5 | N | O | 4-methylmorpholine | 2-chloro-N-(3-methylphenyl)pyridine-4-carboxamide | — | F: 487 |

TABLE 6-continued

| Co | Syn | X | Y | NR²R³ | R⁴ | Sal | DAT |
|---|---|---|---|---|---|---|---|
| 21 | 5 | N | O | 4-methylmorpholine | N-(3-methylphenyl)-2-aminopyridine-3-carboxamide | 2HCl | M: 173-175; N1; 7.53 (1H, t, J = 7.8 Hz), 8.24-8.29 (2H, m), 11.01 (1H, s) |
| 22 | 5 | N | O | 4-methylmorpholine | N-(3-methylphenyl)-1H-pyrazole-4-carboxamide | HCl | N1: 3.87 (4H, m), 8.30 (2H, s), 10.06 (1H, s) |
| 23 | 5 | N | O | 4-methylmorpholine | N-(3-methylphenyl)-2-(pyridin-2-yl)acetamide | 2HCl | N1: 4.39 (2H, s), 7.47 (1H, t, J =7.7 Hz), 10.87 (1H, s) |
| 24 | 6 | N | O | 4-methylmorpholine | N-(3-methylphenyl)acetamide | — | N1: 2.09 (3M, s), 3.87 (4H, t, J = 4.9 Hz), 10.11 (1H, s) |
| 25 | 7 | N | O | 4-methylmorpholine | N-(3-methylphenyl)piperidine-3-carboxamide | 2HCl | M: 213-217 |
| 26 | 7 | N | O | 4-methylmorpholine | N-(3-methylphenyl)piperazine-2-carboxamide | 3HCl | M: 203-205 |
| 27 | 7 | N | O | 4-methylmorpholine | N-(3-methylphenyl)piperidine-2-carboxamide | 2HCl | N1: 1.50-1.90 (5H, m), 3.86 (4H, t, J = 4.9 Hz), 11.00 (1H, s) |
| 28 | 7 | N | O | 4-methylmorpholine | N-(3-methylphenyl)piperidine-4-carboxamide | 2HCl | N1: 1.83-2.06 (4H, m), 3.86 (4H, t, J = 4.4 Hz), 10,37 (1H, s) |
| 29 | 8 | N | O | 4-methylmorpholine | 1-(3-methylphenyl)pyrrolidine-2,5-dione | — | N1: 2.84 (4H, s), 3.85 (4H, t, J = 4.9 Hz), 7.38-7.40 (1H, m) |

TABLE 6-continued
| Co | Syn | X | Y | NR²R³ | R⁴ | Sal | DAT |
|---|---|---|---|---|---|---|---|
| 30 | 9 | N | O |  | 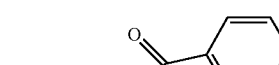 | HCl | M: 293-295 |
| 31 | 10 | N | O |  |  | 2HCl | M: 237-240 |
TABLE 7
| Co | Syn | X | Y | NR²R³ | R⁴ | Sal | DAT |
|---|---|---|---|---|---|---|---|
| 32 | 10 | N | O | morpholine-N-Me | 3-Me-C₆H₄-NH-C(O)-(2-NH₂-C₆H₄) | 2HCl | N1: 3.87 (4H, t, J = 4.4 Hz), 7.51-7.55 (2H, m), 10.68 (1H, s) |
| 33 | 10 | N | O | morpholine-N-Me | 4-Me-C₆H₄-NH₂ | HCl | M: 262-266; N1: 3.86 (4H, t, J = 4.4 Hz), 8.37 (2H, d, J = 8.8 Hz), 8.70 (1H, dd, J = 4.5, 4.9 Hz) |
| 34 | 11 | N | O | NH₂ | H | — | N1: 7.59 (1H, dd, J = 4.8, 7.8 Hz), 7.72 (2H, brs), 8.45 (1H, s) |
| 35 | 12 | N | O | morpholine-N-Me | 3-Me-C₆H₄- | — | M: 237-239 |
| 36 | 12 | N | NH | morpholine-N-Me | 3-Me-C₆H₄- | — | M: 248-250 |
| 37 | 12 | N | S | morpholine-N-Me | 3-Me-C₆H₄- | — | M: 201-202 |
| 38 | 12 | N | O | morpholine-N-Me | H | — | M: 182-183 |

TABLE 7-continued

| Co | Syn | X | Y | NR²R³ | R⁴ | Sal | DAT |
|---|---|---|---|---|---|---|---|
| 39 | 12 | CH | S | N-methylmorpholine | H | HCl | M: 202-205 |
| 40 | 13 | N | O | N-methylmorpholine | 3-methylphenyl amide of 6-(2-aminoethylamino)nicotinamide | 2HCl | M: 237-240; N1: 3.09-3.14 (2H, m), 7.50 (1H, t, J = 7.8 Hz), 10.59 (1H, s) |
| 41 | 13 | N | O | N-methylmorpholine | 3-methylphenyl amide of 2-(2-aminoethylamino)isonicotinamide | 3HCl | M: 178(dec.); N1: 3.13-3.16 (2H, m), 7.54 (1H, t, J = 7.8 Hz), 11.04 (1H, s) |
| 42 | 13 | N | O | N-methylmorpholine | 3-methylphenyl amide of 6-(methylamino)nicotinamide | 2HCl | M: 282-285; N1: 3.09 (3H, s), 7.51 (1H, t, J = 7.8 Hz), 10.79 (1H, s) |
| 43 | 13 | N | O | N-methylmorpholine | 3-methylphenyl amide of 6-(benzylamino)nicotinamide | 2HCl | M: 257-261; N1: 4.81 (2H, s), 7.33-7.53 (6H, m), 10.76 (1H, s) |
| 44 | 14 | N | O | N-methylmorpholine | 3-methylphenyl amide of 6-(dimethylamino)nicotinamide | 2HCl | M: 234-237; N1: 3.32 (6H, s), 7.53 (1H, t, J = 7.8 Hz), 10.75 (1H, s) |
| 45 | 15 | N | O | N-methylmorpholine | N-(3-methylphenyl)benzamide | HCl | M: 244-245; N1: 3.87 (4H, t, J = 4.9 Hz), 7.49-7.67 (5H, m), 10.47 (1H, s) |

TABLE 8

| Co | Syn | X | Y | NR²R³ | R⁴ | Sal | DAT |
|---|---|---|---|---|---|---|---|
| 46 | 15 | N | O | N-methylmorpholine | 3-methylphenyl amide of nicotinamide | 2HCl | N1: 3.87 (4H, t, J = 4.9 Hz), 7.53 (1H, t, J = 7.8 Hz), 10.73 (1H, s) |

TABLE 8-continued
| Co | Syn | X | Y | NR²R³ | R⁴ | Sal | DAT |
|---|---|---|---|---|---|---|---|
| 47 | 15 | N | O | 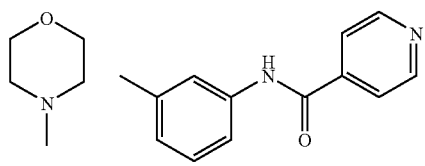 | 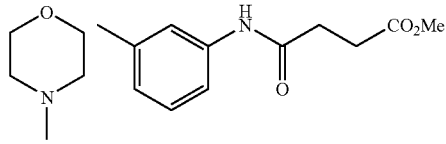 | 2HCl | N1: 3.87 (4H, t, J = 4,9 Hz), 7.55 (1H, t, J = 7.8 Hz), 10.86 (1H, s) |
| 48 | 15 | N | O | 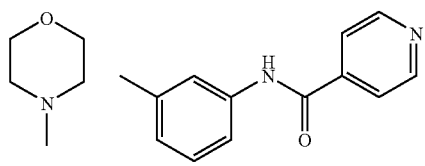 | 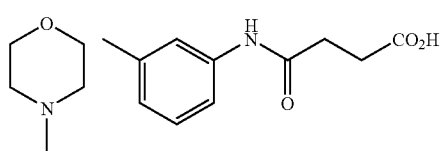 | HCl | M: 195-197; N1: 3.62 (3H, s), 7.44 (1H, t, J = 7.8 Hz), 10.25 (1H, s) |
| 49 | 16 | N | O | 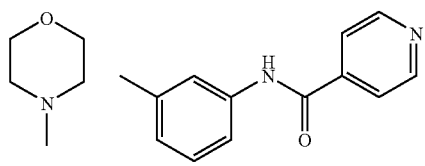 | 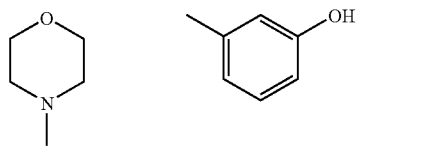 | HCl | M: 164-167; N1: 2.55-2.64 (4H, m), 7.43 (1H, t, J = 7.8 Hz), 10.17 (1H, s) |
| 50 | 17 | N | O | 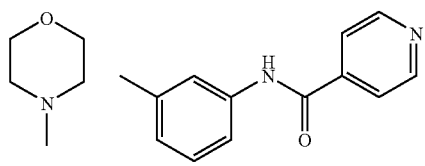 | 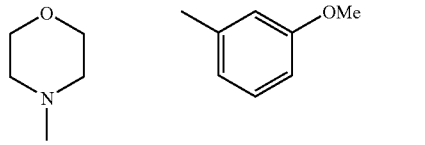 | HCl | M: 270-272; N1: 4.15 (4H, t, J = 4.8 Hz), 7.32 (1H, t, J = 7.8 Hz), 8.70 (1H, dd, J = 1.9, 4.9 Hz) |
| 51 | 17 | N | O | 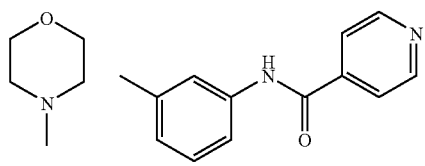 | 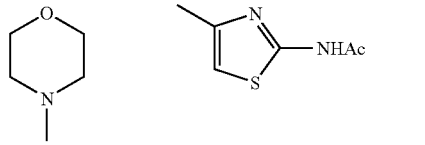 | HCl | M: 182-184; N1: 3.87 (3H, s), 7.45 (1H, t, J = 7.8 Hz), 8.69 (1H, dd, J = 1.5, 4.9 Hz) |
| 52 | 17 | N | O | 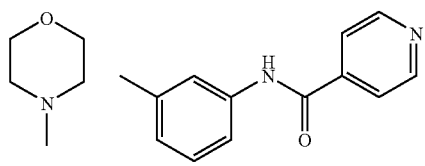 | 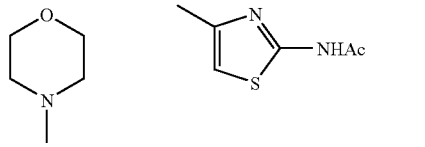 | HCl | M: 306 (dec.); N1: 3.85 (4H, t, J = 4.9 Hz), 6.91 (2H, d, J = 8.8 Hz), 8.32 (2H, d, J = 8.8 Hz) |
| 53 | 17 | N | O | 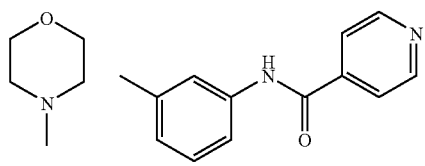 | 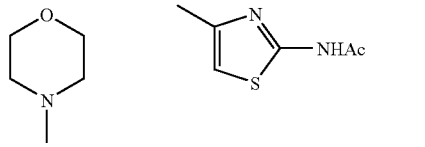 | HCl | N1: 2.18 (3H, s), 8.11 (1H, s), 12.50 (1H, s) |
| 54 | 18 | N | O | 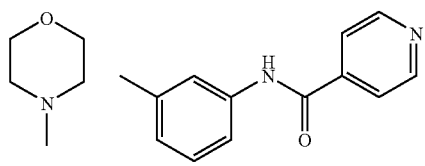 | 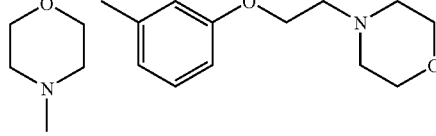 | 2HCl | M: 186-190; N1: 4.15 (4H, t, J = 4.4 Hz), 4.59 (2H, t, J = 4.8 Hz), 7.49 (1H, t, J = 7.8 Hz) |
| 55 | 18 | N | O | 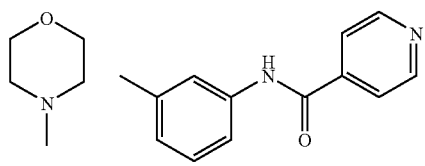 | 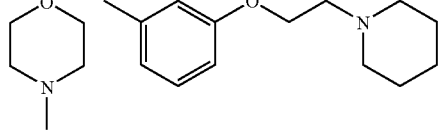 | 2HCl | M: 283-286; N1: 1.35-1.47 (1H, m), 4.56 (2H, t, J ≦ 4.9 Hz), 7.49 (1H, t, J = 7.8 Hz) |
| 56 | 18 | N | O | 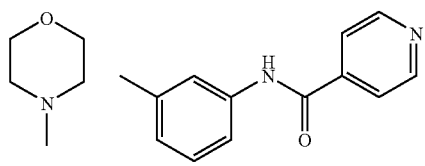 | 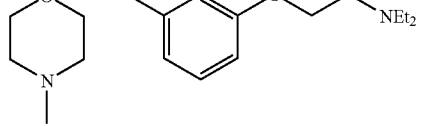 | 2HCl | M: 233-235; N1: 1.30 (6H, t, J = 7.3 Hz), 4.53 (2H, t, J = 4.9 Hz), 7.49 (1H, t, J = 7.8 Hz) |

TABLE 8-continued

| Co | Syn | X | Y | NR²R³ | R⁴ | Sal | DAT |
|---|---|---|---|---|---|---|---|
| 57 | 18 | N | O | 4-methylpiperazinyl | 4-(2-(4-methylphenoxy)ethyl)morpholine | 2HCl | M: 275-277; N1: 3.19-3.28 (2H, m), 7.15 (2H, d, J = 8.8 Hz), 8.46 (2H, d, J = 8.8 Hz) |

TABLE 9

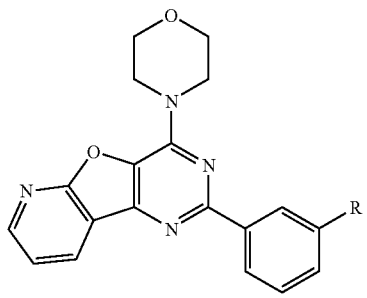

(Ia)

| Co | Syn | R | Sal | DAT |
|---|---|---|---|---|
| 58 | 47 | 4-(3-methoxypropyl)morpholine | HCl | N1: 3.29-3.34 (2H, m), 7.46 (1H, t, J = 7.8 Hz), 8.68-8.71 (2H, m) |
| 59 | 48 | N-methyl-2-morpholinoethylamine | 2HCl | M: 206-210; N1: 4.17 (4H, t, J = 4.9 Hz), 7.73 (1H, d, J = 7.8 Hz), 7.81 (1H, s) |
| 60 | 49 | —NHCOCF₃ | — | N1: 3.86 (4H, t, J = 4.9 Hz), 7.64 (1H, dd, J = 5.0, 7.7 Hz), 11.43 (1H, s) |
| 61 | 18 | N-methyl-N-(2-morpholinoethyl)trifluoroacetamide | — | N1: 7.56-7.67 (3H, m), 8.48-8.53 (2H, m), 8.62-8.65 (1H, m) |
| 62 | 50 | 2-methoxyethyl bromide derivative | — | N1: 3.83-3.88 (6H, m), 7.45 (1H, t, J = 7.9 Hz), 8.67-8.72 (2H, m) |
| 63 | 50 | 4-methoxybutyl bromide derivative | — | N1: 1.85-2.07 (4H, m), 4.10-4.14 (6H, m), 8.65-8.70 (2H, m) |
| 64 | 51 | 1-(2-methoxyethyl)-4-methylpiperazine | 3HCl | N1: 2.85 (3H, br s), 4.16 (4H, t, J = 4.4 Hz), 7.66 (1H, dd, J =4.9, 7.8 Hz) |
| 65 | 18 | 1,2-dimethoxyethane derivative | — | N1: 4.19 (2H, t, J = 4.9 Hz), 7.62 (1H, t, J = 7.8 Hz), 7.96 (1H, s) |
| 66 | 51 | N-methyl-bis(2-methoxyethyl)amine | 2HCl | M: 196-198; N21: 3.33 (6H, s), 7.50 (1H, t, J = 7.8 Hz), 8.07-8.11 (2H, m) |

TABLE 9-continued

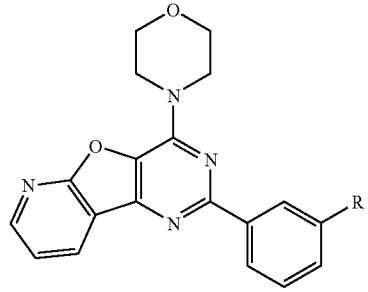

(Ia)

| Co | Syn | R | Sal | DAT |
|----|-----|---|-----|-----|
| 67 | 51 | (2-methoxyethyl-thiomorpholine) | HCl | N1: 4.12 (4H, t, J = 4.3 Hz), 38.09 (1H, d, J = 8.0 Hz), 8,65-8.69 (2H, m) |
| 68 | 51 | (4-methoxybutyl-morpholine) | 2HCl | M: 250-253; N1: 4.56 (2H, t, J = 4.9 Hz), 7.49 (1H, t, J = 7.8 Hz), 8.10 (1H, d, J = 7.8 Hz) |
| 69 | 52 | (2-methoxyethyl-piperazine) | 3HCl | M: 250-253; N1: 4.56 (2H, t, J = 4.9 Hz), 7.49 (1H, t, J = 7.8 Hz), 8.10 (1H, d, J = 7.8 Hz) |
| 70 | 53 | (N-Me-N-(2-morpholinoethyl)amino) | 2HCl | N1: 3.05 (3H, s), 4.19 (4H, t, J = 4.4 Hz), 7.91 (1H, br s) |

TABLE 10

| Co | Syn | R | Sal | DAT |
|----|-----|---|-----|-----|
| 71 | 15 | (N-Ac-N-Me-(2-morpholinoethyl)amino) | 2HCl | M: 244-245; N1: 1.84 (3H, s), 4.11-4.18 (6H, m), 7.64-7.72 (3H, m) |
| 72 | 51 | (2-methoxyethyl-imidazole) | 2HCl | M: 196-201; N1: 4.15 (4H, t, J = 4.4 Hz), 7.74 (1H, s), 9.34 (1H, s) |
| 73 | 15 | (N-Me-acrylamide) | HCl | N1: 5.79 (1H, d, J = 10.8 Hz), 6.30 (1H, d, J = 17.1 Hz), 10.40 (1H, s) |
| 74 | 51 | (2-methoxyethyl-4-hydroxypiperidine) | 2HCl | N1: 4.15 (4H, t, J = 4.9 Hz), 4.53-4.56 (2H, m), 8.05 (1H, s) |
| 75 | 18 | OCH₂CO₂Et | HCl | N1: 1.24 (3H, t, J = 6.8 Hz), 4.22 (2H, q, J = 6.8 Hz), 4.89 (2H, s) |
| 76 | 16 | OCH₂CO₂H | HCl | M: 264-267; N1: 4.79 (2H, s), 7.45 (1H, t, J = 7.8 Hz), 7.64 (1H, dd, J = 4.9, 7.8 Hz) |
| 77 | 54 | OCH₂CH₂OH | HCl | M: 243-244; N1: 3.78 (2H, t, J = 4.9 Hz), 4.14 (4H, t, J = 4.9 Hz), 7.98-7.99 (1H, m) |

TABLE 11
(Ia)
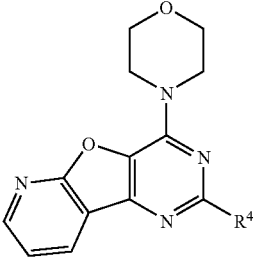
| Co | Syn | R⁴ | Sal | DAT |
|---|---|---|---|---|
| 78 | 47 | 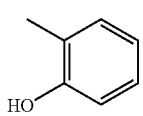 | 2HCl | N1: 3.05-3.14 (2H, m), 3.26-3.31 (2H, m), 7.10 (2H, d, J = 8.8 Hz) |
| 79 | 55 | 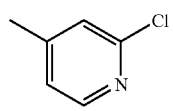 | — | N1: 4.15 (4H, t, J = 4.9 Hz), 7.66 (1H, dd, J = 4.9, 7.8 Hz), 8.15 (1H, dd, J = 1.5, 7.8 Hz) |
| 80 | 12 | 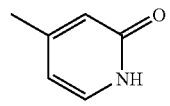 | — | N1: 4.16 (4H, t, J = 4.9 Hz), 7.67 (1H, dd, J = 4.9, 7.3 Hz), 8.34-8.35 (2H, m) |
| 81 | 56 | 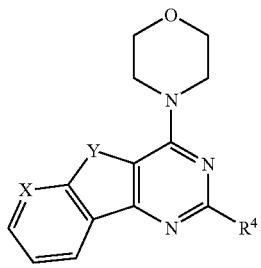 | — | M: 343-347; N1: 7.64 (1H, dd, J = 4.9, 7.3 Hz), 8.66-8.69 (2H, m), 11.72 (1H, br) |
TABLE 12
(Ia)
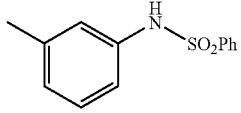
| Co | X | Y | R⁴ |
|---|---|---|---|
| A1 | N | S | 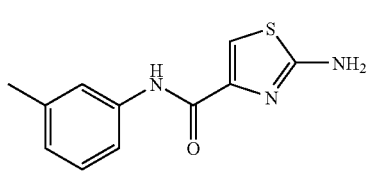 |
| A2 | N | S | 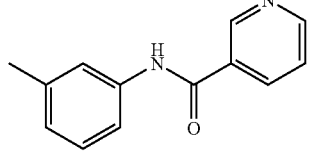 |
| A3 | N | S | 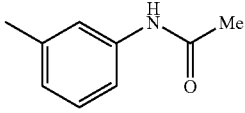 |
| A4 | N | S | (3-methylphenyl)-NH-C(=O)-Me |

TABLE 12-continued (Ia)

| Co | X | Y | R⁴ |
|---|---|---|---|
| A5 | N | S | N-(3-methylphenyl)pyridine-2-carboxamide |
| A6 | N | S | N-(3-methylphenyl)pyridine-4-carboxamide |
| A7 | N | S | 6-amino-N-(3-methylphenyl)nicotinamide |
| A8 | N | O | 2-(2-aminothiazol-4-yl)-N-(3-methylphenyl)acetamide |
| A9 | N | O | 6-amino-N-(3-methylphenyl)pyridine-3-sulfonamide |
| A10 | N | S | 2-(2-aminothiazol-4-yl)-N-(4-methylphenyl)acetamide |
| A11 | N | S | 3-methylphenol |
| A12 | N | S | 5-methylbenzene-1,3-diol |
| A13 | N | O | 5-methylbenzene-1,3-diol |
| A14 | N | S | 4-methylbenzene-1,3-diol |
| A15 | N | O | 3-methylbenzamide |
| A16 | N | S | 3-methylbenzamide |
| A17 | N | O | 4-methylbenzamide |
| A18 | N | S | 4-methylbenzamide |
| A19 | N | O | 4-methyl-2-(2-morpholinoethoxy)phenol |
| A20 | N | S | 4-methyl-2-(2-morpholinoethoxy)phenol |
| A21 | N | O | N-(2-(3-methylphenoxy)ethyl)thiazol-2-amine |

TABLE 12-continued (Ia)

| Co | X | Y | R⁴ |
|---|---|---|---|
| A22 | N | S | 3-methylphenoxy-ethyl-NH-thiazole |
| A23 | N | O | 3-methylphenoxy-ethyl-N(Me)-thiazole |
| A24 | N | S | 3-methylphenoxy-ethyl-N(Me)-thiazole |
| A25 | N | O | 3-methylbenzyl alcohol |
| A26 | N | S | 3-methylbenzyl alcohol |

TABLE 13

| Rco | Rex | Str | DAT |
|---|---|---|---|
| 50 | 10 | EtO-C(=NH)-C₆H₄-CO₂Me · HCl | F: 208 |
| 51 | 10 | EtO-C(=NH)-C₆H₃(NO₂)₂ · HCl | F: 240 |
| 52 | 11 | 6-AcHN-2-(3-nitrophenyl)quinazolin-4(3H)-one | E: 324 |
| 53 | 11 | 6-MeO-2-(3-CF₃-phenyl)quinazolin-4(3H)-one | F: 321 |
| 54 | 11 | 6,7-diMeO-2-phenyl-quinazolin-4(3H)-one | F: 283 |
| 55 | 11 | 6-HO-2-benzyl-quinazolin-4(3H)-one | F: 253 |
| 56 | 11 | 6-F-2-phenyl-quinazolin-4(3H)-one | F: 241 |
| 57 | 11 | 6-HO-2-(4-(PhNHC(O))phenyl)-quinazolin-4(3H)-one | F: 321 |
| 58 | 11 | 6-AcHN-2-phenyl-quinazolin-4(3H)-one | F: 280 |

TABLE 13-continued
| Rco | Rex | Str | DAT |
|---|---|---|---|
| 59 | 11 | 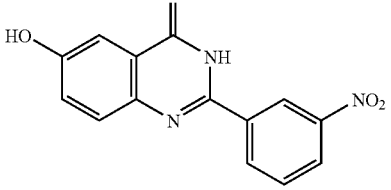 | FN: 282 |
| 60 | 11 | 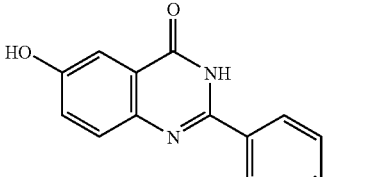 | FN: 282 |
| 61 | 11 | 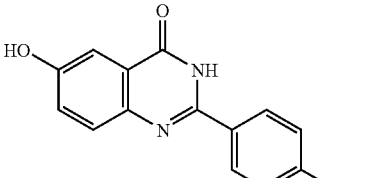 | F: 297 |
| 62 | 11 | 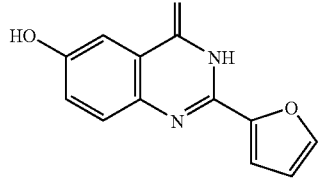 | FN: 227 |
| 63 | 11 | 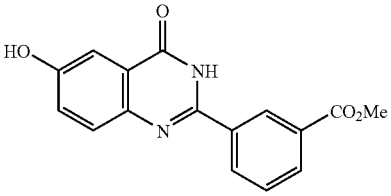 | F: 297 |
| 64 | 11 | 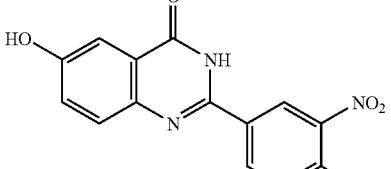 | F: 329 |
| 65 | 11 | 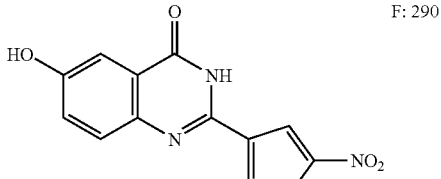 | F: 290 |
TABLE 13-continued
| Rco | Rex | Str | DAT |
|---|---|---|---|
| 66 | 11 | 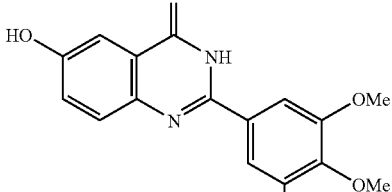 | F: 329 |
| 67 | 12 | 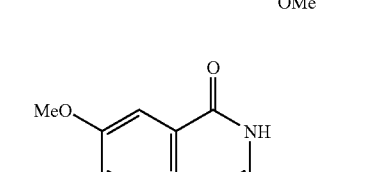 | F: 259 |
| 68 | 12 | 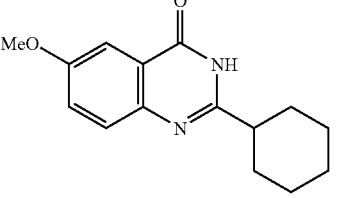 | F: 313 |
| 69 | 12 | 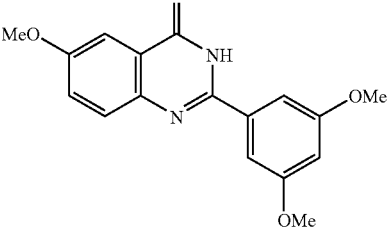 | F: 279 |
TABLE 14
| Rco | Rex | Str | DAT |
|---|---|---|---|
| 70 | 12 | 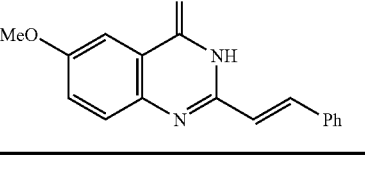 | F: 271 |
| 71 | 12 | 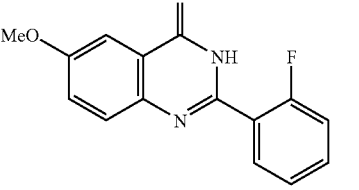 | F: 254 |

TABLE 14-continued
| Rco | Rex | Str | DAT |
|---|---|---|---|
| 72 | 13 | 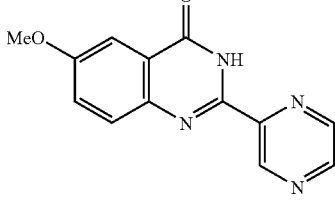 | F: 255 |
| 73 | 13 | 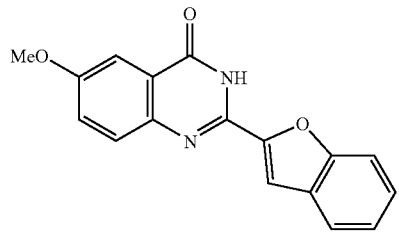 | F: 293 |
| 74 | 14 | 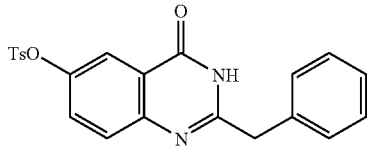 | F: 407 |
| 75 | 14 | 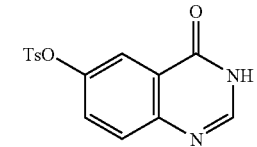 | F: 317 |
| 76 | 14 | 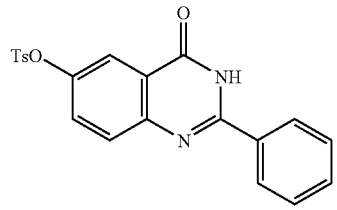 | F: 393 |
| 77 | 15 | 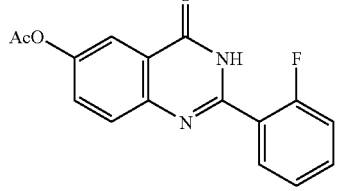 | F: 299 |
| 78 | 15 | 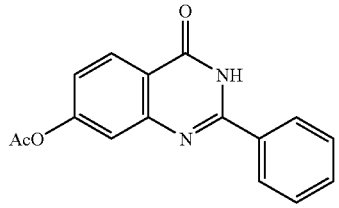 | F: 281 |
| 79 | 15 | 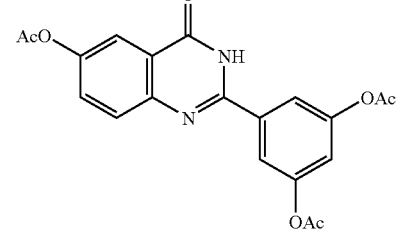 | F: 397 |
| 80 | 15 | 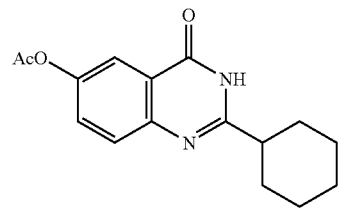 | F: 287 |
| 81 | 15 | 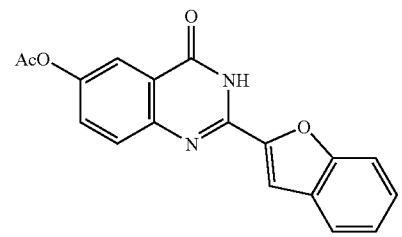 | F: 321 |
| 82 | 15 | 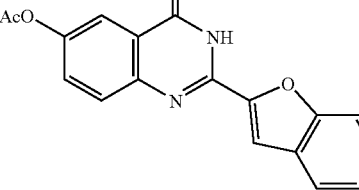 | F: 282 |
| 83 | 16 | 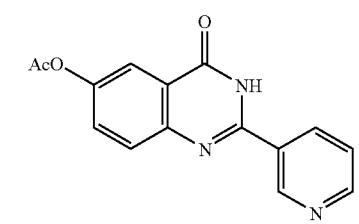 | FN: 324 |
| 84 | 16 | 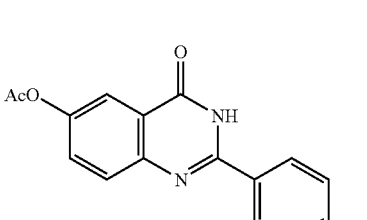 | F: 271 |

TABLE 14-continued

| Rco | Rex | Str | DAT |
|---|---|---|---|
| 85 | 16 | (6-AcO-quinazolin-4(3H)-one, 2-(3,4,5-trimethoxyphenyl)) | F: 371 |
| 86 | 16 | (6-AcO-quinazolin-4(3H)-one, 2-(4-CO2Me-phenyl)) | F: 339 |
| 87 | 16 | (6-AcO-quinazolin-4(3H)-one, 2-(3,4-dinitrophenyl)) | FN: 369 |
| 88 | 16 | (6-AcO-quinazolin-4(3H)-one, 2-(5-nitrothiophen-3-yl)) | F: 332 |
| 89 | 16 | (6-AcO-quinazolin-4(3H)-one, 2-(3-CO2Me-phenyl)) | F: 339 |

TABLE 15

| Rco | Rex | Str | DAT |
|---|---|---|---|
| 90 | 16 | (6-AcO-quinazolin-4(3H)-one, 2-(3-nitrophenyl)) | F: 326 |
| 91 | 16 | (6-AcO-quinazolin-4(3H)-one, 2-(4-(NHPh-carbonyl)phenyl)) | F: 400 |
| 92 | 17 | (6-AcO-quinazolin-4(3H)-one, 2-(3-OAc-phenyl)) | F: 339 |

TABLE 15-continued

| Rco | Rex | Str | DAT |
|---|---|---|---|
| 93 | 17 | AcO-quinazolin-4(3H)-one-2-(3,4-dimethoxyphenyl) | F: 341 |
| 94 | 17 | AcO-quinazolin-4(3H)-one-2-(3-OMe-4-OAc-phenyl) | F: 369 |
| 95 | 18 | MsHN-quinazolin-4(3H)-one-2-(3-nitrophenyl) | FN: 359 |
| 96 | 3 | methyl 4-(3-methoxybenzamido)nicotinate | F: 286 |
| 97 | 3 | methyl 3-(3-methoxybenzamido)isonicotinate | F: 287 |
| 98 | 3 | methyl 3-(3-methoxybenzamido)picolinate | F: 287 |

TABLE 15-continued
| Rco | Rex | Str | DAT |
|---|---|---|---|
| 99 | 3 | 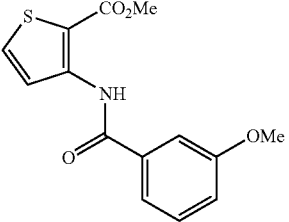 | F: 292 |
| 100 | 3 | 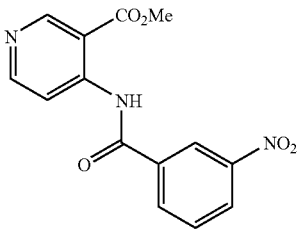 | F: 302 |
| 101 | 3 | 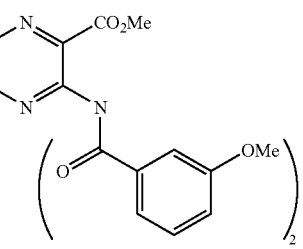 | F: 422 |
| 102 | 8 | 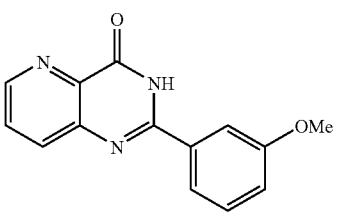 | F: 254 |
| 103 | 8 | 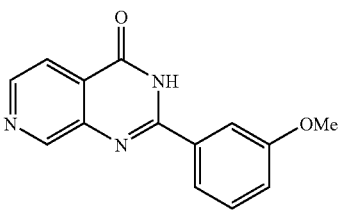 | F: 254 |
| 104 | 8 | 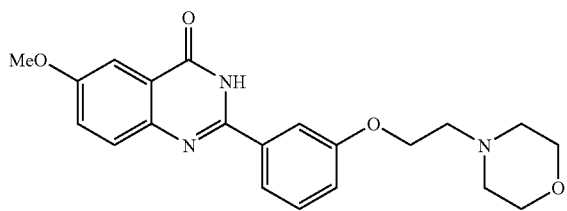 | F: 382 |
| 105 | 8 | 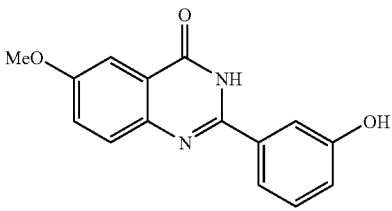 | F: 269 |

TABLE 15-continued
| Rco | Rex | Str | DAT |
|---|---|---|---|
| 106 | 9 | 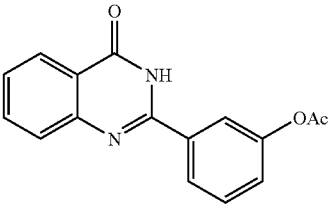 | F: 281 |
| 107 | 9 | 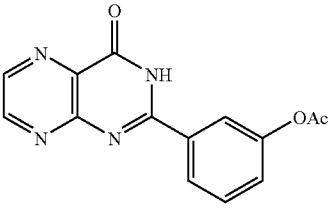 | F: 283 |
| 108 | 9 | 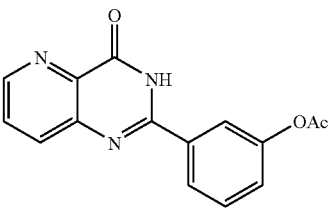 | F: 282 |
| 109 | 9 | 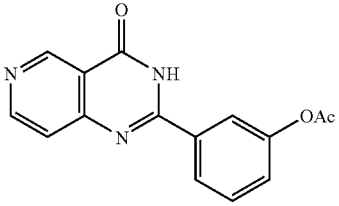 | F: 282 |
TABLE 16
| Rco | Rex | Str | DAT |
|---|---|---|---|
| 110 | 9 | 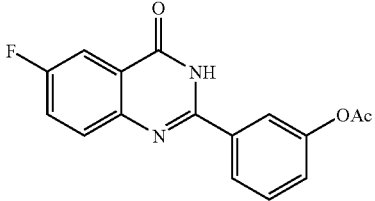 | F: 299 |
| 111 | 9 | 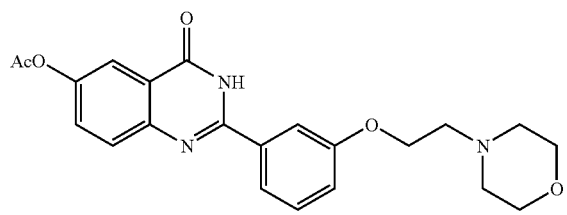 | F: 410 |

TABLE 16-continued
| Rco | Rex | Str | DAT |
|---|---|---|---|
| 112 | 9 | 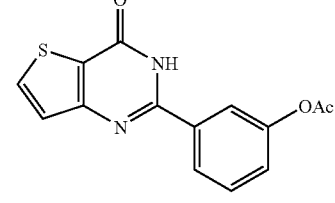 | F: 286 |
| 113 | 9 | 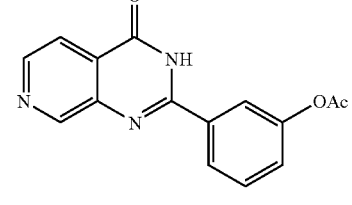 | F: 282 |
| 114 | 9 | 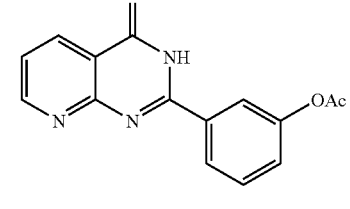 | F: 282 |
| 115 | 11 | 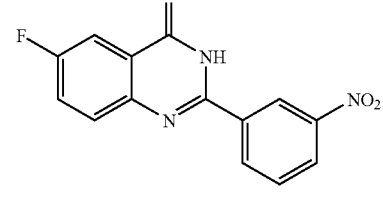 | F: 286 |
| 116 | 20 | 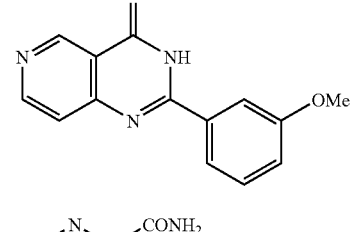 | F: 254 |
| 117 | 21 | 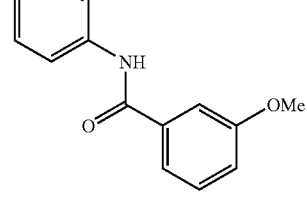 | F: 272 |
| 118 | 21 | 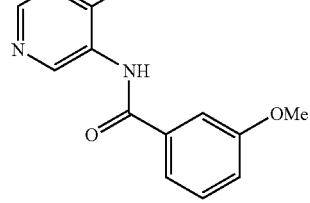 | F: 272 |

TABLE 16-continued

| Rco | Rex | Str | DAT |
|---|---|---|---|
| 119 | 22 | 5-methoxy-2-[(3-methoxybenzoyl)amino]benzamide | F: 329 |
| 120 | 22 | 5-methoxy-2-[[3-[2-(morpholin-4-yl)ethoxy]benzoyl]amino]benzamide | F: 400 |
| 121 | 23 | 2-(3-acetoxyphenyl)-6-methoxy-quinazolin-4(3H)-one | F: 311 |
| 122 | 24 | 2-(3-methoxyphenyl)thieno[3,2-d]pyrimidin-4(3H)-one | F: 259 |
| 123 | 24 | 2-(3-methoxyphenyl)pteridin-4(3H)-one | F: 255 |
| 124 | 24 | 2-(3-nitrophenyl)pyrido[4,3-d]pyrimidin-4(3H)-one | F: 269 |

TABLE 17

(Ib)

Structure: Quinazoline core with R³R²N- at position 4, R¹ at positions 6/7, X at position 3, R⁴ at position 2.

| Co | Syn | X | R¹ | NR²R³ | R⁴ | Sal | DAT |
|---|---|---|---|---|---|---|---|
| 82 | 19 | N | H | morpholin-4-yl | phenyl | — | M: 111-112; N2: 3.86 (4H, m), 3.95 (4H, m), 8.56 (2H, m) |
| 83 | 19 | N | 6-F | morpholin-4-yl | phenyl | — | M: 157-159; N2: 3.80 (4H, t, J = 4.7 Hz), 3.94 (4H, t, J = 4.7 Hz), 8.50-8.54 (2H, m) |
| 84 | 19 | N | 6-MeO-7-MeO | morpholin-4-yl | phenyl | — | M: 182-186 |
| 85 | 19 | N | 6-NO₂ | morpholin-4-yl | phenyl | — | M: 238-240; N1: 3.83 (4H, t, J = 4.9 Hz), 7.99 (1H, d, J = 8.8 Hz), 8.82 (1H, d, J = 2.4 Hz) |
| 86 | 19 | N | 6-AcHN | morpholin-4-yl | phenyl | — | M: 121-124 |
| 87 | 19 | N | 6-MeO | morpholin-4-yl | 3-CF₃-phenyl | — | M: 145-146; N1: 3.79 (4H, m), 3.87 (4H, m), 3.94 (3H, s) |
| 88 | 19 | N | 6-AcHN | morpholin-4-yl | 3-NO₂-phenyl | — | N1: 8.52 (1H, s), 8.86 (1H, m), 10.36 (1H, s) |
| 89 | 19 | N | 6-MeO | pyrrolidin-1-yl | phenyl | — | M: 161-163 |
| 89 | 19 | N | 6-MeO | MeNH-CH₂CH₂-OH | phenyl | — | M: 218-220 |

TABLE 17-continued
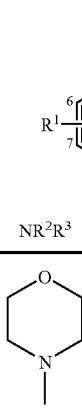
(Ib)
| Co | Syn | X | R¹ | NR²R³ | R⁴ | Sal | DAT |
|---|---|---|---|---|---|---|---|
| 90 | 19 | N | 6-MsHN | 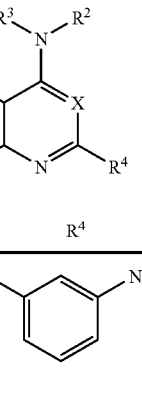 | 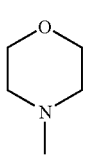 | — | N1: 3.10 (3H, s), 3.80-3.90 (8H, m), 10.18 (1H, br) |
| 91 | 19 | CH | 6-MeO | 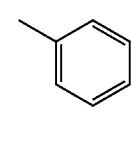 | 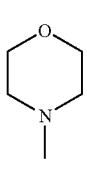 | — | N1: 3.92 (8H, m), 7.96 (1H, d, J = 8.8 Hz), 8.22 (2H, m) |
| 92 | 20 | N | 6-MeO-7-OH | 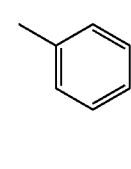 | 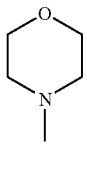 | — | M: 202-204; N1: 3.70 (4H, t, J = 4.4 Hz), 3.98 (3H, s), 7.07 (1H, s) |
| 93 | 20 | N | 6-HO | 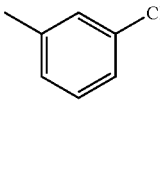 | 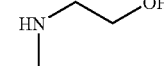 | — | M: 203-205; N1: 3.79 (4H, m), 3.87 (4H, m), 10.22 (1H, s) |
| 94 | 20 | N | 6-HO | 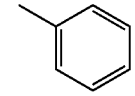 | 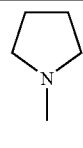 | — | M: 222-225 (dec.); N1: 3.12 (4H, m), 4.82 (1H, brs), 8.01 (1H, brs) |
TABLE 18
| Co | Syn | X | R¹ | NR²R³ | R⁴ | Sal | DAT |
|---|---|---|---|---|---|---|---|
| 96 | 20 | N | 6-HO | 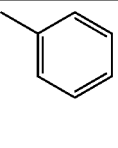 | 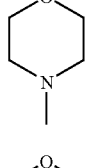 | — | M: 296-305 (dec.) |
| 97 | 21 | N | 6-H₂N | 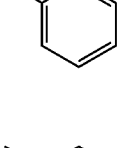 | 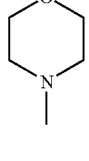 | — | M: 184-186 |
| 98 | 22 | N | 6-OHCHN— | 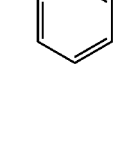 | 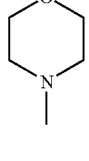 | — | M: 218-222; N1: 3.79 (4H, t, J = 4.2 Hz), 8.41 (1H, d, J = 1.5 Hz), 10.59 (1H, s) |

TABLE 18-continued

| Co | Syn | X | R¹ | NR²R³ | R⁴ | Sal | DAT |
|---|---|---|---|---|---|---|---|
| 99 | 23 | N | 6-HO | morpholine (N-linked) | ethylphenyl | — | M: 243-249; N1: 4.07 (2H, s), 7.67 (1H, d, J = 8.8 Hz), 10.00 (1H, s) |
| 100 | 23 | N | 6-HO | 4-oxopiperidine (N-linked) | phenyl | — | M: 258-262 (dec.) |
| 101 | 23 | N | 6-HO | morpholine (N-linked) | H | — | M: 259-260; N1: 3.57 (4H, t, J = 4.7 Hz), 8.55 (1H, s) 10.12 (1H, s) |
| 102 | 23 | N | 6-HO | 4-hydroxypiperidine (N-linked) | phenyl | — | M: 249-250; N1: 3.62 (1H, m), 7.77 (1H, d, J = 9.6 Hz), 10.08 (1H, s) |
| 103 | 23 | N | 6-HO | 2,6-dimethylmorpholine (N-linked) | phenyl | — | M: 221-225; N1: 1.20 (6H, d, J = 6.4 Hz), 7.80 (1H, d, J = 8.8 Hz), 10.12 (1H, s) |
| 104 | 23 | N | 6-HO | N(CH₂CH₂OMe)₂ | phenyl | — | M: 139-141 |
| 105 | 24 | N | 6-AcMeN— | morpholine (N-linked) | phenyl | — | M: 204-206 |
| 106 | 25 | N | 6-TsHN— | morpholine (N-linked) | phenyl | — | M: 199-290; N1: 2.32 (3H, s) 3.62 (4H, t, J = 4.4 Hz), 10.65 (1H, s) |
| 107 | 26 | N | 6-Me₂N— | morpholine (N-linked) | phenyl | — | M: 124-125 |

TABLE 18-continued

| Co | Syn | X | R¹ | NR²R³ | R⁴ | Sal | DAT |
|---|---|---|---|---|---|---|---|
| 108 | 27 | N | 6-HO | thiomorpholine (N-linked) | phenyl | 0.5 HCl | M: 268-271 |
| 109 | 28 | N | 6-HO | morpholine (N-linked) | Me | — | M: 281-284 |

TABLE 19

| Co | Ex. | X | R¹ | NR²R³ | R⁴ | Sal | DAT |
|---|---|---|---|---|---|---|---|
| 110 | 29 | N | 7-HO | morpholine (N-linked) | phenyl | — | M: 245-246 |
| 111 | 29 | N | 6-HO | morpholine (N-linked) | 4-NO₂-phenyl | — | M: 266-269; N1: 3.74 (4H, t, J = 4.4 Hz), 8.66 (2H, d, J = 9.1 Hz), 10.29 (1H, s) |
| 112 | 29 | N | 6-HO | morpholine (N-linked) | 3-NO₂-phenyl | — | M: 226-227 |
| 113 | 29 | N | 6-HO | morpholine (N-linked) | cyclohexyl | — | N1: 1.94 (2H, m), 2.69 (1H, m), 7.65 (1H, d, J = 8.8 Hz) |
| 114 | 29 | N | 6-HO | morpholine (N-linked) | 3-pyridyl | — | M: 275-277; N1: 7.83 (1H, d, J = 8.8 Hz), 9.58 (1H, d, J = 1.5 Hz), 10.09 (1H, brs) |
| 115 | 29 | N | 6-HO | morpholine (N-linked) | 2-furyl | — | M: 280 (dec.) |
| 116 | 29 | N | 6-HO | morpholine (N-linked) | 4-(CO₂Me)-phenyl | — | M: 239-241 |

TABLE 19-continued
| Co | Ex. | X | R¹ | NR²R³ | R⁴ | Sal | DAT |
|---|---|---|---|---|---|---|---|
| 117 | 29 | N | 6-HO | 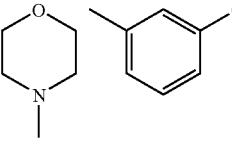 | 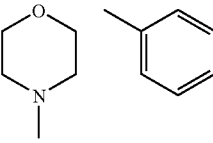 | — | M: 184-186; N1: 3.92 (3H, s), 9.03 (1H, br), 10.19 (1H, s) |
| 118 | 29 | N | 6-HO | 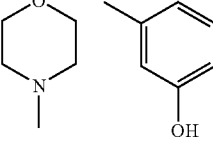 | 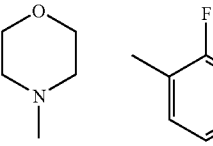 | — | M: 280-284; N1: 3.68 (4H, t, J = 4.5 Hz), 9.49 (1H, s), 10.12 (1H, s) |
| 119 | 29 | N | 6-HO | 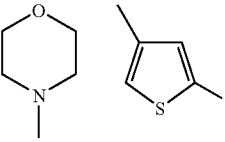 |  | — | M: 306-311 (dec.); N1: 7.75 (1H, d, J = 8.8 Hz), 9.29 (2H, s), 10.10 (1H, s) |
| 120 | 29 | N | 6-HO | 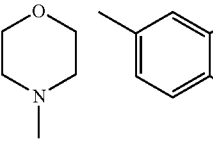 | 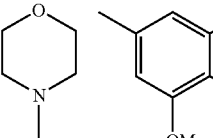 | — | M: 254-255 |
| 121 | 29 | N | 6-HO | | 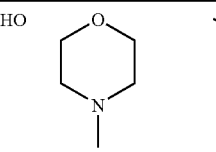 | — | M: 288-290 |
| 122 | 29 | N | 6-HO | | 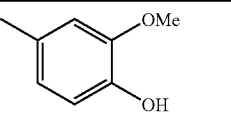 | — | M: 188-190; N1: 3.80 (3H, s), 13.83 (3H, s), 10.06 (1H, s) |
| 123 | 29 | N | 6-HO | | 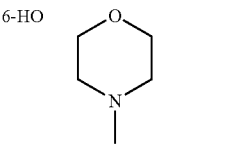 | — | M: 224-227 |
TABLE 20
| Co | Syn | X | R¹ | NR²R³ | R⁴ | Sal | DAT |
|---|---|---|---|---|---|---|---|
| 124 | 29 | N | 6-HO | | 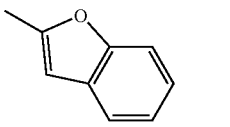 | — | M: 285-288; N1: 3.88 (3H, s), 9.37 (1H, s), 10.03 (1H, s) |
| 125 | 29 | N | 6-HO | | | — | M: 310-313; N1: 3.71 (4H, m), 3.87 (4H, m), 10.23 (1H, s) |

TABLE 20-continued
| Co | Syn | X | R¹ | NR²R³ | R⁴ | Sal | DAT |
|---|---|---|---|---|---|---|---|
| 126 | 29 | N | 6-HO | 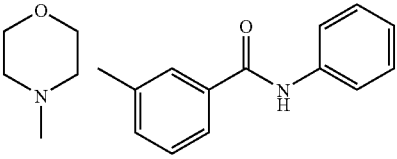 | 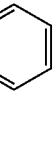 | — | M: 178-180 |
| 127 | 30 | N | 6-HO | 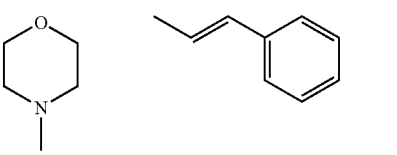 |  | — | M: 260-263; N1: 3.64 (4H, m), 3.86 (4H, m), 1H, 10.12 (1H, s) |
| 128 | 30 | N | 6-HO | 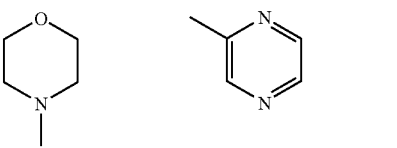 |  | — | M: 280-282 |
| 129 | 31 | N | 6-HO | 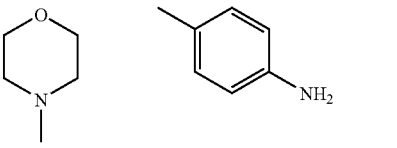 |  | — | M: 285 (dec.); N1: 3.62 (4H, t, J = 4.7 Hz), 5.51 (2H, br), 9.95 (1H, s) |
| 130 | 32 | N | 6-HO | 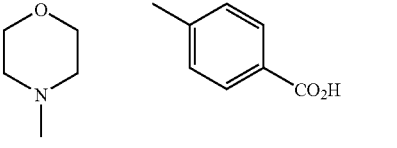 |  | — | M: 305 (dec.) |
| 131 | 32 | N | 6-HO | 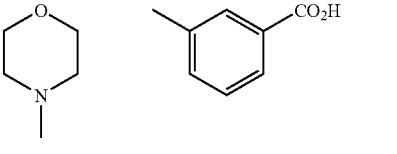 |  | — | M: 306-309; N1: 3.71 (4H, t, J = 4.9 Hz), 10.18 (1H, s), 13.08 (1H, s) |
| 132 | 33 | N | 6-HO | 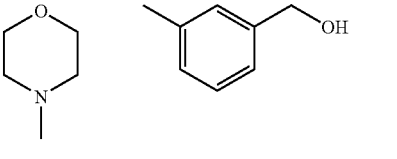 |  | — | M: 204-206; N1: 4.78 (2H, d, J = 5.9 Hz), 5.28 (1H, t, J = 5.9 Hz), 10.13 (1H, s) |
| 133 | 34 | N | 6-HO | 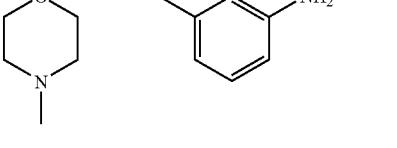 |  | — | M: 274-277; N1: 5.17 (2H, brs), 6.66 (1H, m), 10.08 (1H, s) |
| 134 | 34 | N | 6-MsHN | 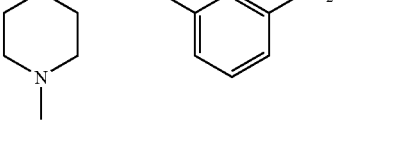 |  | — | N1: 3.07 (3H, s), 3.72-3.77 (4H, m), 10.07 (1H, br s) |
| 135 | 35 | N | 6-HO | 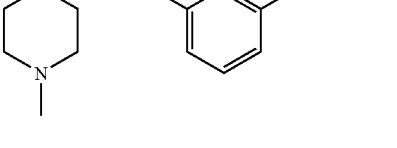 |  | — | M: 266-267 |

TABLE 20-continued
| Co | Syn | X | R¹ | NR²R³ | R⁴ | Sal | DAT |
|---|---|---|---|---|---|---|---|
| 136 | 36 | N | 6-HO | 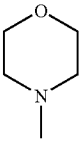 | 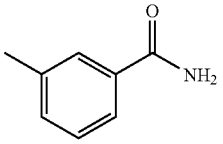 | — | M: 261-264; N1: 8.10 (1H, br), 8.91 (1H, t, J = 1.4), 10.17 (1H, s) |
| 137 | 36 | N | 6-HO | 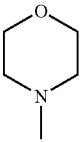 | 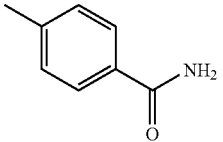 | — | M: 306-309 |
| 138 | 37 | N | 6-HO | 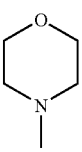 | 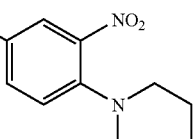 | — | M: 245-248 |
TABLE 21
| Co | Syn | X | R¹ | NR²R³ | R⁴ | Sal | DAT |
|---|---|---|---|---|---|---|---|
| 139 | 38 | N | 6-HO | 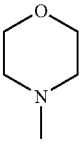 | 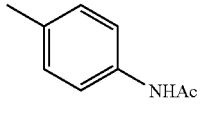 | — | M: 296-299; N1: 2.08 (3H, s), 10.08 (1H, s), 10.11 (1H, s) |
| 140 | 39 | N | 6-HO | 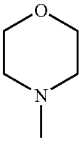 | 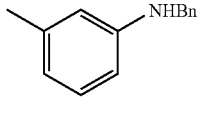 | — | M: 152-157 |
| 141 | 40 | N | 6-HO | 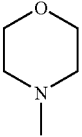 | 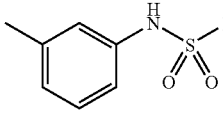 | — | M: 225-228; N1: 8.21 (1H, m), 10.16 (1H, brs), 10.44 (1H, brs) |
| 142 | 40 | N | 6-HO | 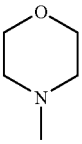 | 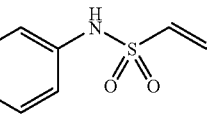 | — | M: 206-207; N1: 8.33 (1H, s), 10.12 (1H, s), 10.18 (1H, s) |
| 143 | 40 | N | 6-HO | 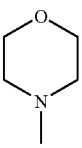 | 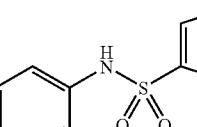 | — | M: 172-174 |
| 144 | 40 | N | 6-AcHN | 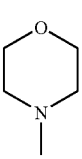 | 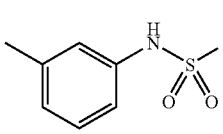 | — | M: 145-150; N1: 8.48 (1H, d, J = 2.0 Hz), 10.33 (1H, brs), 10.44 (1H, brs) |

TABLE 21-continued

| Co | Syn | X | R¹ | NR²R³ | R⁴ | Sal | DAT |
|---|---|---|---|---|---|---|---|
| 145 | 40 | N | 6-MsHN | 4-methylmorpholine | N-(3-methylphenyl)benzenesulfonamide | — | M: 234-236; N1: 3.08 (3H, s), 3.74-3.79 (4H, m), 10.30 (2H, br) |
| 146 | 40 | N | 6-AcHN | 4-methylmorpholine | N-(3-methylphenyl)thiophene-2-sulfonamide | — | M: 145-148; N1: 2.12 (3H, s), 10.34 (1H, s), 10.56 (1H, s) |
| 147 | 40 | N | 6-AcHN | 4-methylmorpholine | N-(3-methylphenyl)naphthalene-1-sulfonamide | — | M: 290 (d); N1: 2.12 (3H, s), 10.32 (1H, s), 10.83 (1H, s) |
| 148 | 41 | N | 6-HO | 4-methylmorpholine | 1-(3-methylphenyl)-3-phenylurea | — | M: 167-169 |
| 149 | 42 | N | 6-HO | 4-methylmorpholine | phenyl (3-methylphenyl)carbamate | — | M: 144-147 |
| 150 | 43 | N | 6-HO | 4-methylmorpholine | N-(3-methylphenyl)isonicotinamide | — | M: 175-178; N1: 3.71-3.73 (4H, m), 10.17 (1H, s), 10.68 (1H, s) |
| 151 | 43 | N | 6-HO | 4-methylmorpholine | N-(3-methylphenyl)cyclohexanecarboxamide | — | M: 239-243; N1: 2.33-2.42 (1H, m), 3.66-3.69 (4H, m), 9.96 (1H, s) |

TABLE 22

| Co | Ex. | X | R¹ | NR²R³ | R⁴ | Sal | DAT |
|---|---|---|---|---|---|---|---|
| 152 | 43 | N | 6-HO | 4-methylmorpholine | N-(3-methylphenyl)-2-phenylacetamide | — | M: 214-216; N1: 3.68-3.70 (6H, m), 10.14 (1H, s), 10.34 (1H, s) |
| 153 | 43 | N | 6-HO | 4-methylmorpholine | N-(3-methylphenyl)furan-2-carboxamide | — | M: 246-247 |

TABLE 22-continued
| Co | Ex. | X | R¹ | NR²R³ | R⁴ | Sal | DAT |
|---|---|---|---|---|---|---|---|
| 154 | 43 | N | 6-HO | 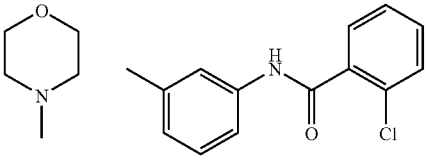 |  | — | M: 251-252 |
| 155 | 43 | N | 6-HO | 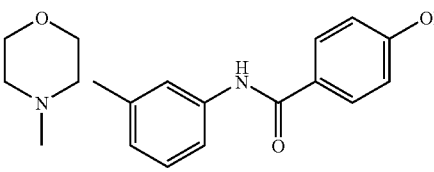 |  | — | N1: 3.86 (3H, s), 10.14 (1H, s), 10.26 (1H, s) |
| 156 | 43 | N | 6-HO | 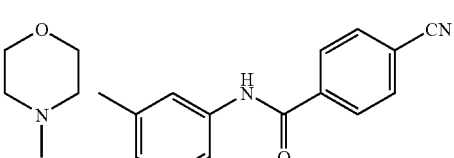 |  | — | M: 182-183 |
| 157 | 43 | N | 6-HO | 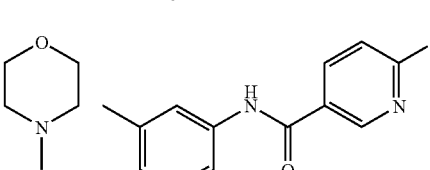 | 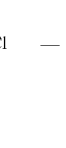 | — | N1: 3.72-3.74 (4H, m), 9.70-9.99 (1H, br), 10.45 (1H, br s) |
| 158 | 43 | N | 6-HO | 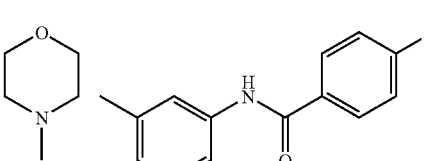 |  | — | M: 232-233 |
| 159 | 44 | N | 6-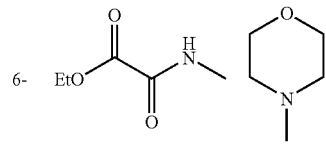 | 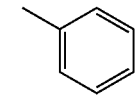 | 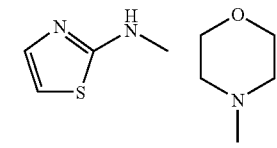 | — | M: 182-183 |
| 160 | 45 | N | 6-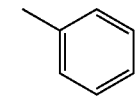 | 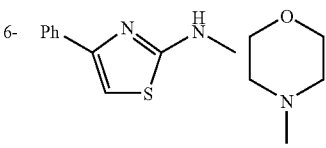 | | — | M: 224-227 |
| 161 | 45 | N | 6-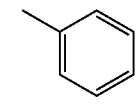 | | | — | M: 199-202; N1: 8.76 (1H, d, J = 2.4 Hz), 8.49 (2H, m), 10.74 (1H, brs) |
| 162 | 46 | CH | 6-HO | 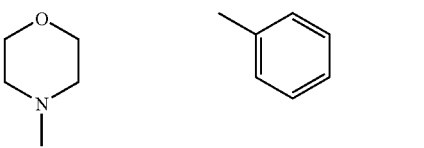 | 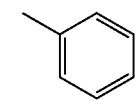 | — | M: 250-253 |

TABLE 23

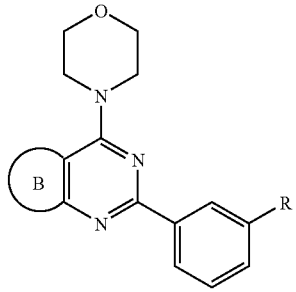

| Co | Syn | B | R | Sal | DAT |
|---|---|---|---|---|---|
| 163 | 17 | 3,4-pyridyl | OMe | 2HCl | N1: 3.84 (4H, t, J = 4.9 Hz), 3.89 (3H, s), 9.55 (1H, s) |
| 164 | 17 | 3,4-pyridyl | OH | HCl | M: 261-266; N1: 3.84 (4H, t, J = 4.9 Hz), 7.91 (1H, s), 9.53 (1H, s) |
| 165 | 18 | 3,4-pyridyl | -OCH₂CH₂-morpholine | 3HCl | M: 167-170; N1: 3.61 (2H, br s), 4.61 (2H, t, J = 4.9 Hz), 9.54 (1H, s) |
| 166 | 47 | 3,4-pyridyl | -OCH₂CH₂CH₂-morpholine | 3HCl | N1: 3.26-3.31 (2H, m), 7.54 (1H, t, J = 7.8 Hz), 9.53 (1H, s) |
| 167 | 17 | 3,4-pyridyl | NO₂ | HCl | M: 272-273; N1: 4.20 (4H, t, J = 4.9 Hz), 7.97 (1H, d, J = 6.4 Hz), 9.62 (1H, s) |
| 168 | 34 | 3,4-pyridyl | NH₂ | 2HCl | M: 195-200; N1: 4.25 (4H, t, J = 4.9 Hz), 7.64 (1H, t, J = 7.8 Hz), 9.55 (1H, s) |
| 169 | 57 | 3,4-pyridyl | NHAc | HCl | N1: 2.10 (3H, s), 9.52 (1H, s), 10.32 (1H, s) |
| 170 | 3 | 3,4-pyridyl | NHSO₂Ph | HCl | N1: 8.75 (1H, d, J = 6.4 Hz), 9.49 (1H, s), 10.62 (1H, s) |
| 171 | 2 | 3,4-pyridyl | -NHC(O)-(6-amino-pyridin-3-yl) | 2HCl | M: 200-203; N1: 8.89-8.90 (1H, m), 9.53 (1H, s), 10.84 (1H, s) |
| 172 | 17 | 2,3-pyridyl | OH | HCl | M: 233-238; N1: 4.73 (4H, br), 7.43 (1H, t, J = 7.8 Hz), 10.02 (1H, br) |
| 173 | 18 | 2,3-pyridyl | -OCH₂CH₂-morpholine | 2HCl | M: 201-206; N1: 3.19-3.29 (2H, m), 7.55 (1H, t, J = 7.8 Hz), 8.50 (1H, br) |

TABLE 23-continued

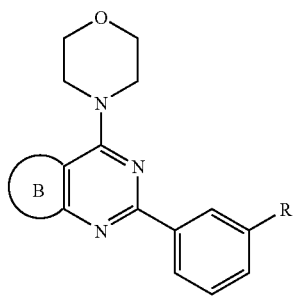

(Ib)

| Co | Syn | B | R | Sal | DAT |
|---|---|---|---|---|---|
| 174 | 17 | 3,4-dimethylpyridyl | OH | HCl | M: 269-274; N1: 7.39 (1H, t, J = 7.8 Hz), 8.06 (1H, d, J = 5.9 Hz), 9.44 (1H, s) |
| 175 | 18 | 3,4-dimethylpyridyl | -OCH₂CH₂-morpholine | 2HCl | N1: 3.20-3.29 (2H, m), 4.60 (2H, t, J = 4.9 Hz), 9.50 (1H, s) |

TABLE 24

| Co | Syn | B | R | Sal | DAT |
|---|---|---|---|---|---|
| 176 | 17 | 2,3-dimethylpyridyl | OMe | HCl | M: 159-162; N1: 3.89 (3H, s), 7.55 (1H, t, J = 7.8 Hz), 8.02 (1H, d, J = 7.8 Hz) |
| 177 | 17 | 2,3-dimethylpyridyl | OH | HCl | M: 274-279; N1: 4.22 (4H, t, J = 4.9 Hz), 7.41 (1H, t, J = 7.8 Hz), 10.05 (1H, br) |
| 178 | 18 | 2,3-dimethylpyridyl | -OCH₂CH₂-morpholine | 2HCl | N1: 4.59 (2H, t, J = 4.9 Hz), 7.57 (1H, t, J = 7.8 Hz), 7.68 (1H, dd, J = 4.9, 8.3 Hz) |
| 179 | 17 | 4-F-1,2-dimethylphenyl | OH | HCl | M: 235-237; N1: 4.19 (4H, br s), 7.43 (1H, t, J = 7.8 Hz), 8.27-8.34 (1H, m) |
| 180 | 18 | 4-F-1,2-dimethylphenyl | -OCH₂CH₂-morpholine | 2HCl | N1: 4.19 (4H, br s), 8.28 (1H, br s), 8.57 (1H, br) |
| 181 | 17 | 4-F-1,2-dimethylphenyl | NO₂ | HCl | N1: 3.78-3.79 (4H, m), 7.83-7.89 (3H, m), 8.88 (1H, d, J = 7.8 Hz) |
| 182 | 34 | 4-F-1,2-dimethylphenyl | NH₂ | 2HCl | N1: 4.11 (4H, br s), 7.47 (1H, d, J = 7.8 Hz), 7.62 (1H, t, J = 7.8 Hz) |

TABLE 24-continued
| Co | Syn | B | R | Sal | DAT |
|---|---|---|---|---|---|
| 183 | 57 | 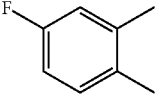 | NHAc | HCl | N1: 2.10 (3H, s), 7.52 (1H, t, J = 7.8 Hz), 10.25 (1H, s) |
| 184 | 3 | 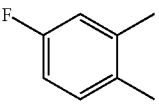 | NHSO₂Ph | HCl | N1: 4.10 (4H, br s), 8.17-8.28 (3H, m), 10.83 (1H, s) |
| 185 | 2 | 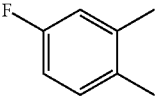 | 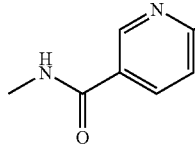 | 2HCl | M: 196-201; N1: 4.15 (4H, br s), 8.85-8.87 (2H, m), 10.97 (1H, s) |
| 186 | 17 | 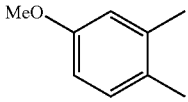 | OH | HCl | M: 252-258; N1: 3.95 (3H, s), 4.23 (4H, br s), 10.04 (1H, br) |
| 187 | 18 | 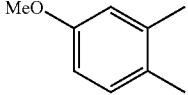 | 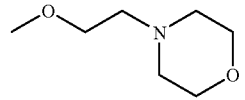 | 2HCl | N1: 4.67 (2H, t, J = 4.9 Hz), 8.12 (1H, d, J = 7.8 Hz), 8.49 (1H, br) |
| 188 | 17 | 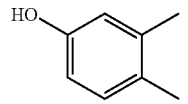 | 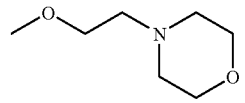 | 2HCl | M: 266-267; N1: 4.60-4.63 (2H, m), 8.16 (1H, s), 10.68 (1H, br) |
| 189 | 17 | 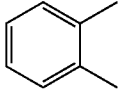 | OH | HCl | M: 214-220; N1: 4.26 (4H, br), 7.45 (1H, t, J = 7.8 Hz), 7.82 (1H, s) |
| 190 | 17 | 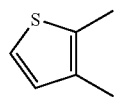 | OH | HCl | M: 207-210; N1: 7.40 (1H, t, J = 7.8 Hz), 7.86 (1H, d, J = 7.8 Hz), 8.51 (1H, d, J = 5.3 Hz) |
| 191 | 17 | 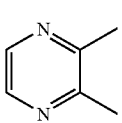 | OH | HCl | M: 262-268 (d); N1: 4.58 (4H, br), 8.87 (1H, d, J = 2.0 Hz), 9.09 (1H, d, J = 2.0 Hz) |
| 192 | 58 | 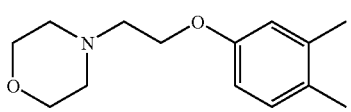 | OH | 2HCl | M: 270-273; N1: 4.66-4.68 (2H, m), 7.55 (1H, br s), 10.05 (1H, br) |

TABLE 25
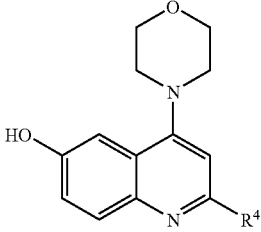
(Ib)
| Co | R⁴ |
|---|---|
| B1 | 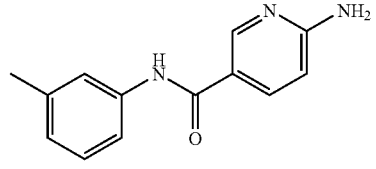 |
| B2 | 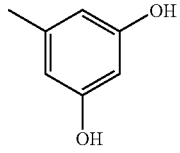 |
| B3 | 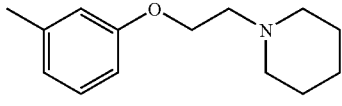 |
| B4 | 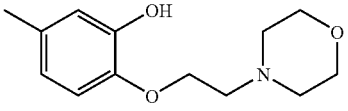 |
| B5 | 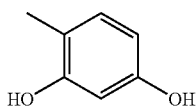 |
| B6 | 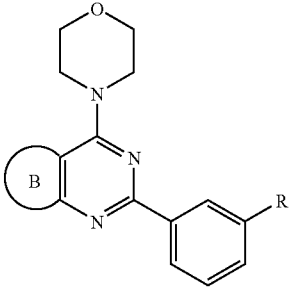 |
TABLE 26
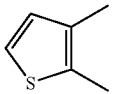
(Ib)
| Co | B | R |
|---|---|---|
| B7 | 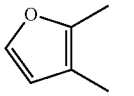 | CO₂NHMe |
| B8 | 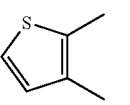 | OH |
| B9 | 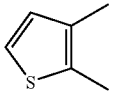 | OH |
| B10 | 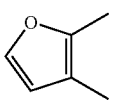 | CH₂OH |
| B11 | 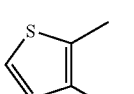 | CH₂OH |
| B12 | 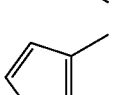 | CH₂OH |
| B13 | 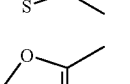 | CONH₂ |
| B14 | | CONH₂ |
| B15 | | CONH₂ |
| B16 | 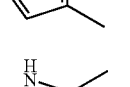 | OH |
| B17 | 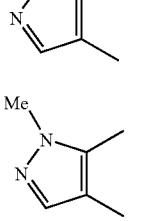 | OH |

TABLE 26-continued (Ib)

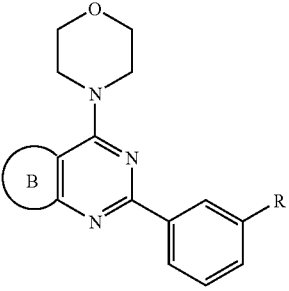

| Co | B | R |
|---|---|---|
| B18 | 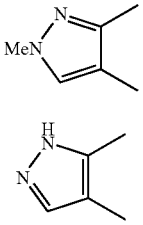 | OH |
| B19 | 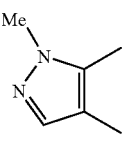 | CH₂OH |
| B20 | 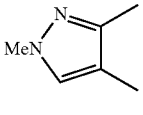 | CH₂OH |
| B21 | 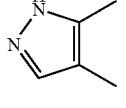 | CH₂OH |
| B22 | 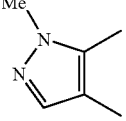 | CONH₂ |
| B23 | 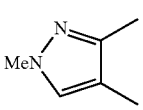 | CONH₂ |
| B24 | 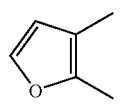 | CONH₂ |
| B25 | 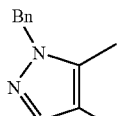 | OH |
| B26 | 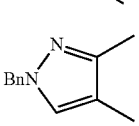 | OH |
| B27 | 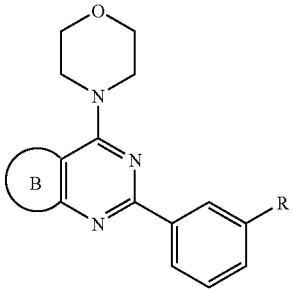 | OH |

TABLE 26-continued (Ib)

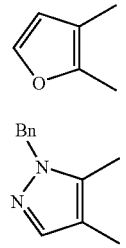

| Co | B | R |
|---|---|---|
| B28 | 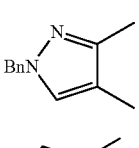 | CH₂OH |
| B29 | 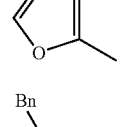 | CH₂OH |
| B30 | 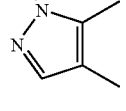 | CH₂OH |
| B31 | 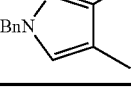 | CONH₂ |
| B32 | | CONH₂ |
| B33 | | CONH₂ |

Production methods of the starting compounds shown in the foregoing tables are explained in the following Reference Examples.

Reference Example 1

A suspension of 2-chloro-3-cyanopyridine, ethyl glycolate and sodium carbonate in 3-methyl-1-butanol was refluxed for 3 days. The solvent was evaporated and water was added to the residue to crystallize to give Reference Example Compound (hereinbelow, abbreviated as Rco) 1.

Reference Example 2

A suspension of 2-chloro-3-cyanopyridine, glycine ethyl ester hydrochloride and sodium carbonate in 3-methyl-1-butanol was refluxed for 6 days. The solvent was evaporated. After the obtained residue was diluted with ethyl acetate and water, insoluble solids were filtered off. The separated organic layer was concentrated under reduced pressure. The residue was dissolved in ethanol, sodium ethoxide was added, and the mixture was stirred at room temperature for 15 minutes. The reaction solution was concentrated, and ethyl acetate saturated aqueous sodium hydrogencarbonate were added. The separated organic layer was concentrated under reduced pressure and the residue was purified with silica gel column chromatography to give Rco 3.

Reference Example 3

Dimethylaminopyridine and benzoyl chloride were added to a solution of 3-aminothieno[2,3-b]pyridine-2-carboxylic acid ethyl ester in pyridine. The reaction mixture was stirred at room temperature for 18 hours, and concentrated. 1M Hydrochloric acid was added, and the mixture was extracted with chloroform. The organic layer was concentrated under reduced pressure. The obtained residue was purified with silica gel column chromatography to give Rco 4.

Reference Example 4

Phosphorous oxychloride was added to a solution of Rco 49 and 4-nitrobenzoic acid and the reaction mixture was stirred at −15 C. for 15 minutes. Ice and water was added to this reaction mixture. The precipitated crystals were collected to give Rco 11.

Reference Example 5

1M Sodium hydroxide was added to a solution of Rco 4 in methanol. The reaction mixture was stirred at room temperature for 2 hours, and 1M hydrochloric acid was added. The precipitated crystals were collected to give Rco 13.

Reference Example 6

Thionyl chloride was added to Rco 13. The mixture was refluxed for 2 hours, cooled to room temperature and then concentrated. DMF and aqueous ammonia were added to the obtained residue and the reaction mixture was stirred at room temperature for 2 hours. Water was added to the resulting mixture and extracted with chloroform. The organic layer was concentrated under reduced pressure to give Rco 21.

Reference Example 7

Formamide was added to Rco 1 and the mixture was stirred at 200 C. for 2 hours. After the mixture was cooled to room temperature, the precipitated crystals were collected to give Rco 29.

Reference Example 8

2M potassium hydroxide was added to a solution of Rco 21 in methanol and the mixture was stirred at 100 C. for 1 hour. After being cooled to room temperature, hydrochloric acid was added. The precipitated crystals were collected to give Rco 30.

Reference Example 9

Acetic acid and 48% hydrobromic acid were added to Rco 36 and the mixture was refluxed for 17 hours. After the reaction solution was concentrated under reduced pressure, diethyl ether was added and the reaction mixture was concentrated under reduced pressure. Sodium acetate and acetic anhydride were added to the obtained residue, and the mixture was stirred at 110 C. for 2 hours. Ice and then water were added to this reaction mixture under ice cooling. The precipitated crystals were collected to give Rco 38.

Reference Example 10

Ethanol was added to a solution of 3-cyanobenzoic acid methyl ester in chloroform and gaseous hydrogen chloride was passed into the mixture at 0 C. for 15 minutes. Further, the solution was sealed and the solution was stirred at 0 C. for 17 hours. The reaction mixture was concentrated, ether was added, and the precipitated crystals were collected to give Rco 50.

Reference Example 11

2-Propanol was added to a mixture of 5-acetoamidoanthranilic acid, 3-nitrobenzimidic acid ethyl ester hydrochloride and sodium methoxide, and the mixture was refluxed for 3 days. The reaction solution was allowed to cool to room temperature. The obtained solid was collected to give Rco 52.

Reference Example 12

A solution of cyclohexanecarbonyl chloride in benzene was added in dropwise to a solution of 2-amino-5-methoxybenzamide and dimethylaminopyridine in pyridine at room temperature, and the mixture was stirred for 2 hours. The reaction mixture was concentrated, and the residue was dissolved with ethyl acetate. After the organic layer was washed with 1M hydrochloric acid and saturated aqueous sodium hydrogencarbonate, it was concentrated and the obtained residue was dissolved with methanol. 2M Sodium hydroxide was added. After the reaction solution was refluxed for 2 hours, it was neutralized with 12M hydrochloric acid. The solvent was evaporated and the crystals were filtered to give Rco 67.

Reference Example 13

THF and DMF were added to a mixture of 2-amino-5-methoxybenzamide, EDCI hydrochloride, HOBt and pyrazinecarboxylic acid, and the mixture was stirred at room temperature for 3 days. The solvents were evaporated, and the crystals were collected and dissolved in methanol and 2M sodium hydroxide. The reaction solution was refluxed for 3 hours and neutralized with 12M hydrochloric acid. The obtained crystals were collected to give Rco 72.

Reference Example 14

Dimethylaminopyridine, TEA, ethanol and tosyl chloride were added to a suspension of Rco 55 in chloroform, and the reaction mixture was stirred at room temperature for 12 hours. DMSO was added to it to give a solution. Then, the reaction solution was stirred for 12 hours. Again, dimethylaminopyridine, TEA and tosyl chloride were added and the reaction solution was stirred for 18 hours. The reaction solution was concentrated, and the residue was diluted with ethyl acetate and purified according to a conventional method to give Rco 74.

Reference Example 15

48% Hydrobromic acid was added to a solution of Rco 70 in acetic acid, and the mixture was refluxed for 2 days. After the reaction solution was allowed to cool, it was concentrated, and sodium acetate and acetic anhydride were added to the obtained residue. The reaction solution was refluxed for 3 hours. After the reaction solution was allowed to cool, it was concentrated and ether was added to the solution, followed by collection of crystals to give Rco 77.

Reference Example 16

Sodium acetate and acetic anhydride were added to Rco 60, and the mixture was refluxed for 40 minutes. After the reaction mixture was allowed to cool, the precipitated crystals were collected to give Rco 83.

Reference Example 17

Sodium methoxide was added to a solution of 3-hydroxybenzimidate ethyl ester hydrochloride and 5-hydroxyanthranilic acid in methanol, and the mixture was refluxed for 30 minutes. After the reaction solution was cooled to room temperature, the precipitate was collected. Sodium acetate and acetate anhydride were added to the obtained precipitate and the mixture was refluxed for 30 minutes. After the reaction solution was allowed to cool, the precipitated crystals were collected to give Rco 92.

Reference Example 18

Concentrated hydrochloric acid was added to Rco 52, and the mixture was stirred at 80 C. The reaction mixture was allowed to cool, filtered, and concentrated under reduced pressure to give 6-amino-2-(3-nitrophenyl)-3H-quinazoline-4-one hydrochloride. After the obtained compound was neutralized, pyridine, dimethylaminopyridine and methanesulfonyl chloride were added. The reaction solution was stirred at room temperature for 20 hours, the solvent was evaporated and the crystals were collected to give Rco 95.

Reference Example 19

1,8-diazabicyclo[5,4,0]-7-undecene (DBU) was added to a solution of 2-chloro-3-cyanopyridine and ethyl glycolate in ethanol and the reaction mixture was refluxed for 21 hours. The resulting mixture was evaporated under reduced pressure, diluted with ethyl acetate and then, washed with water and brine. The organic layer was concentrated under reduced pressure and crystallized to give Rco 49.

Reference Example 20

Aqueous ammonia was added to a solution of Rco 96 in methanol, and the reaction solution was stirred at room temperature for 3 hours. Methanol in the reaction mixture was evaporated under reduced pressure and the crystals were collected to give Rco 116.

Reference Example 21

Aqueous ammonia was added to a solution of Rco 98 in methanol, and the reaction solution was stirred at room temperature overnight. Methanol in the reaction mixture was evaporated under reduced pressure and the crystals were collected to give Rco 117.

Reference Example 22

EDCI hydrochloride and HOBt were added to a solution of 3-acetoxybenzoic acid in DMF, and the reaction mixture was stirred at room temperature for 10 minutes. Then, 2-amino-5-methoxybenzamide was added, and the reaction mixture was stirred at room temperature for 1 hour. The solvent was evaporated under reduced pressure, and waster and THF were added. After the extraction with ethyl acetate, the organic layer was washed with brine, evaporated under reduced pressure, and crystallized to give Rco 119.

Reference Example 23

Acetic anhydride was added to Rco 105 and sodium acetate, and the reaction mixture was stirred at 110 C. for 1 hour and 15 minutes. Under cooling, the precipitated crystals were collected to give Rco 121.

Reference Example 24

Aqueous ammonia was added to a solution of Rco 99 in dioxane, and the reaction mixture was stirred at room temperature for 13 days. The solvent was evaporated under reduced pressure and the crystals were collected to give a mixture of amido 3-(3-methoxybenzoylamino)thiophene-2-carboxylate and Rco 122. 2M aqueous sodium hydroxide was added to a solution of this mixture in 2-propanol and the reaction solution was refluxed for 21 hours. After being cooled, it was neutralized and the precipitated crystals were collected to give Rco 122.

Example 1

Phosphorous oxychloride was added to Rco 33 and the mixture was refluxed for 20 minutes. The reaction mixture was concentrated under reduced pressure, and was azeotropically concentrated with toluene. Morpholine was added to the obtained residue and the mixture was refluxed for 10 minutes. The reaction solution was concentrated under reduced pressure and the obtained crystals were washed with chloroform and water to give Compound (hereinafter, abbreviated as Co) 1.

Example 2

1-Benzyl piperidine-1,2-dicarboxylate, HOBt and EDCI hydrochloride were added to a solution of a free form of Co 31 in DMF, and the mixture was stirred at room temperature for 7 hour. The solvent was evaporated under reduced pressure. After being diluted with ethyl acetate, the organic layer was washed with saturated aqueous sodium hydrogencarbonate and brine. After the solution was dried over anhydrous sodium sulfate, the solvent was evaporated under reduced pressure. The obtained residue was purified with silica gel column chromatography and crystallized to give Co 3.

Example 3

Benzenesulfonyl chloride (6.02 ml) was added to a solution of a free form of C 31 (13.6 g) in pyridine (480 ml) at 0 C. and the mixture was stirred at room temperature for 1.5 hours. The solvent was evaporated under reduced pressure. The obtained residue was dissolved in ethyl acetate and the solution was washed with saturated aqueous sodium hydrogencarbonate and brine. After the solution was dried over anhydrous sodium sulfate, the solvent was evaporated under reduced pressure. The obtained residue was purified with silica gel column chromatography (eluent; chloroform: methanol=96:4) and recrystallized (ethanol) to give Co 8 (15.6 g).

Example 4

Picolinoyl chloride hydrochloride (9.40 g) and TEA (14.7 ml) were added to a solution of a free form of Co 31 (15.3 g) in THF (1 L) at 0 C. and the mixture was stirred at room temperature for 1.5 hours. Then, additional picolinoyl chloride hydrochloride (4.00 g) was added and the mixture was stirred at room temperature for 30 minutes. The reaction mixture was concentrated under reduced pressure. After dissolving in ethyl acetate, the solution was washed with saturated aqueous sodium hydrogencarbonate and brine. After being dried over anhydrous sodium sulfate, the solvent was evaporated under reduced pressure and the obtained residue was purified with silica gel column chromatography (chloroform:methanol=96:4) and recrystallized (ethanol) to give Co 10 (15.4 g).

Example 5

3-Hydroxypicolinic acid (140 mg), EDCI hydrochloride (190 mg) and HOBt (135 mg) were added to a solution of a free form of Co 31 (300 mg) in DMF (20 ml) and the mixture was stirred at room temperature for 2 hours. The solvent was evaporated under reduced pressure. The obtained residue was dissolved with ethyl acetate and THF. The solution was washed with water and saturated aqueous sodium hydrogencarbonate. After the organic layer was dried over anhydrous magnesium sulfate, the solvent was evaporated under reduced pressure. The obtained residue was purified with silica gel column chromatography (chloroform:methanol=100:1). 4M Hydrogen chloride/ethyl acetate was added to a solution of the obtained residue in chloroform and methanol. The solvent was evaporated under reduced pressure, and the obtained solid was crystallized from methanol to give Co 12 (207 mg).

Example 6

A suspension of a free form of Co 31 (300 mg), succinic anhydride (519 mg) and acetic acid (1 ml) was stirred at 100 C. for 30 minutes. The solvent was evaporated under reduced pressure. The obtained residue was purified with silica gel column chromatography (chloroform:methanol=98:2) and recrystallized (methanol) to give Co 24 (106 mg).

Example 7

To a solution of Co 18 (300 mg) in THF (12 ml) and ethanol (12 ml), 10% Pd—C (35 mg) was added, and the mixture was stirred at room temperature under hydrogen atmosphere (1 atm) for 4 hours. The reaction solution was filtered by Celite. After the filtrate was concentrated under reduced pressure, the obtained residue was purified with silica gel column chromatography (chloroform:methanol=98:2-80:20) to give a free form of Co 25 (178 mg). 1M Hydrochloric acid (1.00 ml) was added to a solution of the obtained free form (153 mg) in THF (35 ml) and methanol (20 ml). The reaction solution was stirred at room temperature, then concentrated under reduced pressure, and recrystallized (methanol) to give dihydrochloride of Co 25 (119 mg).

Example 8

A suspension of a free form of Co 31 (300 mg), succinic anhydride (519 mg) and acetic acid (1 ml) was stirred at 100 C. for 30 minutes. The solvent was evaporated under reduced pressure. The obtained residue was purified with silica gel column chromatography (chloroform:methanol=98:2) and recrystallized (methanol) to give Co 29 (57 mg).

Example 9

N-Carboethoxyphthalimide (262 mg) and TEA (0.166 ml) were added to a solution of a free form of Co 31 (346 mg) in THF (60 ml) and the mixture was stirred at 80 C. for 1 day. After the reaction mixture was allowed to cool, water was added, and collected to give a free form of Co 30 (374 mg). 1M Hydrochloric acid (1.55 ml) was added to a solution of the obtained free form (371 mg) in THF (200 ml) and the solution was stirred at room temperature. The precipitated crystals were collected to give hydrochloride of Co 30 (287 mg).

Example 10

Co 1 (22.4 g) and ammonium chloride (1.59 g) were suspended in a mixture of ethanol (717 ml) and water (269 ml). Then, iron (33.2 g) was added and the solution was refluxed for 9 hours. While the reaction solution was still hot, hot THF was added, and the mixture was filtered with Celite. After most of the solvent was evaporated under reduced pressure, the precipitate was collected, and washed with diethyl ether to give a free form of Co 31 (18.9 g). 1M Hydrochoric acid (0.870 ml) was added to a solution of the obtained free form (101 mg) in THF (25 ml) and the solution was stirred at room-temperature. The precipitated crystals were collected, and washed with methanol to give dihydrochloride of Co 31 (75 mg).

Example 11

A solution of Rco 1 (1.03 g) in formamide (12 ml) was refluxed for 2 hours. After the reaction mixture was cooled to room temperature, the obtained solids were collected to give Rco 29 (648 mg). Phosphorous oxychloride (7 ml) was added to a solution of obtained Rco 29 (630 mg) in pyridine (3.5 ml). The reaction mixture was refluxed for 2.5 hours. After being cooled to room temperature, the solvent was evaporated. Toluene (7 ml) was added to the obtained residue. After morpholine (7 ml) was slowly added in dropwise under ice cooling, the reaction mixture was refluxed for 3.5 hours. Further, THF (3 ml) and morpholine (20 ml) were added, and the reaction mixture was refluxed for 5 days, and then concentrated under reduced pressure. After the residue was diluted with ethyl acetate, the crystals were collected, washed with ethyl acetate, saturated aqueous sodium hydrogencarbonate and water, and recrystallized (ethanol) to give Co 34 (372 mg).

Example 12

Phosphorous oxychloride (5 ml) was added to Rco 32 (396 mg) and the mixture was refluxed for 50 minutes. The solvent was evaporated under reduced pressure. After morpholine (10 ml) was slowly added in dropwise into the obtained residue under ice cooling, the reaction mixture was refluxed for 30 minutes. ° The reaction mixture was concentrated under reduced pressure. The obtained crystals were washed with ethyl acetate and water, and recrystallized (ethanol) to give Co 35 (411 mg).

Example 13

Ethylenediamine (1.85 ml) was added to Co 11 (303 mg) and the mixture was stirred at 90 C. for 2 hours. The solvent was evaporated under reduced pressure. The obtained residue was purified with silica gel column chromatography (chloroform:methanol=80:20) and crystallized (methanol) to give a free form of Co 40 (269 mg). The obtained free form (266 mg) was subjected to salt formation as described in EXAMPLE 7, and the obtained residue was recrystallized (methanol) to give dihydrochloride of Co 40 (153 mg).

Example 14

DMF (10 ml) was added to Co 11 (285 mg) and the solution was stirred at 110 C. for 2 hours and at 80 C. for 27 hours. The solvent was evaporated under reduced pressure. The obtained residue was dissolved in ethyl acetate and THF. The reaction solution was washed with aqueous sodium hydrogencarbonate and brine, dried over anhydrous sodium sulfate, and the solvent was evaporated under reduced pressure. The obtained residue was purified with silica gel column chromatography (chloroform:methanol=98:2) to give a free form of Co 44 (167 mg). 1M Hydrochloric acid (0.283 ml) was added to a solution of the obtained free form (70 mg) in THF (5 ml) and methanol (10 ml), and the solution was stirred at room temperature. The precipitated crystals were collected to give dihydrochloride of Co 44 (72 mg).

Example 15

Benzoyl chloride (0.118 ml) was added to a solution of a free form of Co 31 (297 mg) in pyridine (20 ml) under ice cooling and the mixture was stirred at room temperature for 20 minutes. The solvent was evaporated under reduced pressure. The obtained residue was dissolved in ethyl acetate and THF. The reaction solution was washed with aqueous sodium hydrogencarbonate and brine. After being dried over anhydrous sodium sulfate, the solvent was evaporated under reduced pressure. The obtained residue was recrystallized (methanol) to give a free form of Co 45 (301 mg). The obtained free form (287 mg) was subjected to salt formation as described in EXAMPLE 7 to give hydrochloride crystals of Co 45 (249 mg).

Example 16

1M Sodium hydroxide (11 ml) was added in two portions to a solution of a free form of Co 48 (171 mg) in methanol (60 ml) and THF (30 ml), and the mixture was stirred at room temperature for 2.5 hours. The reaction mixture was acidified with 1M hydrochloric acid, and the organic solvent was evaporated under reduced pressure. The precipitate was collected, and washed with water and diethyl ether. The obtained crystals were recrystallized (methanol/diethyl ether) to give Co 49 (116 mg).

Example 17

Phosphorous oxychloride (5 ml) was added to Rco 38 (452 mg), and the mixture was refluxed for 30 minutes. After the reaction solution was cooled to room temperature, it was concentrated under reduced pressure. After adding THF (5 ml) and then slowly adding morpholine (4 ml) in dropwise to the obtained residue under ice cooling, the ice bath was removed and the solution was refluxed for 1 hour. After the reaction mixture was cooled to room temperature. the solvent was evaporated under reduced pressure. The obtained solid was washed with water and diethyl ether and purified, with silica gel column chromatography (chloroform:methanol=98:2) to give a free form of Co 50 (411 mg). The obtained free form (183 mg) was subjected to salt formation as described in EXAMPLE 7 and recrystallized (methanol) to give hydrochloride of Co 50 (129 mg).

Example 18

4-(2-Chloroethyl)morpholine hydrochloride (1.53 g) and potassium carbonate (1.90 g) were added to a solution of a free form of Co 50 (956 mg) in DMF (35 ml), and the mixture was stirred at 70 C. for 2.5 days. After the reaction solution was cooled to room temperature, the solvent was evaporated under reduced pressure. The obtained solid was washed with water and diethyl ether and purified with silica gel column chromatography (chloroform:methanol=98:2) and crystallized (methanol) to give a free form of Co 54 (1.16 g). 4M Hydrochloric acid/ethyl acetate (1.14 ml) was added to a solution of the obtained free form (1.05 g) in THF (140 ml) and methanol (70 ml), and the solution was stirred at room temperature. The solvents were evaporated under reduced pressure, and the material was recrystallized (methanol) to give dihydrochloride crystals of Co 54 (1.18 g).

Example 19

Phosphorous oxychloride (5 ml) was added to 2-phenyl-3H-quinazoline-4-one (450 mg), and the mixture was refluxed for 3 hours. The reaction mixture was concentrated. Saturated aqueous sodium hydrogencarbonate was added and extracted with ethyl acetate. After the organic layer was dried over anhydrous magnesium sulfate, the solvent was evaporated under reduced pressure. The obtained colorless crystals were dissolved in benzene (10 ml) and morpholine (325 mg) was added. The reaction mixture was refluxed overnight. Insoluble materials were filtered off and the filtrate was diluted with ethyl acetate. The organic layer was washed with saturated aqueous sodium hydrogencarbonate, dried over anhydrous magnesium sulfate, and then concentrated under reduced pressure. The obtained residue was purified with column chromatography (hexane:ethyl acetate 5:1) and recrystallized (hexane-benzene) to give Co 82 (136 mg).

Example 20

Sodium cyanide (132 mg) was added to a solution of Co 84 (190 mg) in DMSO (5 ml), and the mixture was stirred at 180 C. for 2 hours. After the reaction mixture was allowed to cool, water was added to it and the mixture was extracted with ethyl acetate. After the organic layer was washed with brine and dried over anhydrous sodium sulfate, the solvent was evaporated under reduced pressure. The obtained residue was recrystallized (hexane/ethyl acetate) to give Co 92 (40 mg).

Example 21

Iron (415 mg) was added to a solution of Co 85 (500 mg) in acetic acid (12 ml), and the mixture was stirred at 105 C. for 1 hour. After the reaction solution was allowed to cool, chloroform and 1M sodium hydroxide were added. The solution was filtered with Celite and the filtrate was extracted with chloroform. The organic layer was washed with brine, dried over anhydrous sodium sulfate, filtered and concentrated under reduced pressure. 1M Hydrochloric acid (10 ml) was added to the obtained residue and the mixture was stirred at 85 C. for 90 minutes. After the mixture was allowed to cool, 1M sodium hydroxide was added and extracted with chloroform, and the organic layer was washed with brine. After the solution was dried over anhydrous sodium sulfate, the solvent was evaporated under reduced pressure. The obtained residue was purified with silica gel column chromatography (eluent; chloroform:methanol=50:1), and recrystallized (chloroform/hexane) to give Co 97 (374 mg).

Example 22

Acetic anhydride (3 ml) was added to a solution of Co 97 (149 mg) in formic acid (3 ml), and the mixture was stirred at room temperature for 2 hours. Water was added and the mixture was extracted with ethyl acetate. The organic layer was washed with saturated aqueous sodium hydrogencarbonate and brine, dried over anhydrous sodium sulfate, and concentrated under reduced pressure. The residue was purified with silica gel column chromatography (eluent; chloroform: methanol=50:1), and recrystallized (chloroform/hexane) to give Co 98 (46 mg).

Example 23

Phosphorous oxychloride (3 ml) was added to Rco 74 (270 mg), and the mixture was refluxed for 0.5 hours. The reaction mixture was concentrated under reduced pressure, and morpholine (10 ml) was added. After the reaction mixture was refluxed for 1 hour, the reaction mixture was concentrated under reduced pressure and diluted with ethyl acetate. The organic layer was washed with saturated aqueous sodium hydrogencarbonate, dried over anhydrous magnesium sulfate, and concentrated under reduced pressure. After purifying by silica gel column chromatography (eluent; hexane:ethyl acetate=5:1), ethanol (2 ml) and 20% potassium hydroxide (100 mg) were added, and the mixture was stirred at room temperature for 40 minutes. The reaction mixture was extracted with ethyl acetate, and the organic layer was washed with saturated aqueous sodium hydrogencarbonate, dried over anhydrous magnesium sulfate, and concentrated under reduced pressure. The obtained crystals were washed with a mixture of ethyl acetate and hexane, and recrystallized (ethyl acetate/hexane) to give Co 99 (30 mg).

Example 24

Sodium hydroxide (43 mg), potassium carbonate (37 mg) and tetra-n-butylammonium hydrogensulfate (2 mg) were added to a solution of Co 86 (95 mg) in toluene (15 ml), and the mixture was stirred at 35 C. for 0.5 hour, followed by addition of dimethylsulfate (34 mg) and stirring at 35 C. for 2 hours. The reaction solution was filtered and the filtrated was concentrated under reduced pressure. The residue was purified with silica gel column chromatography (eluent; chloroform:methanol=20:1), and recrystallized (chloroform/hexane) to give Co 105 (62 mg).

Example 25 p-Toluenesulfonyl chloride (124 mg) and pyridine (1 ml) were added to a solution of Co 97 (200 mg) in chloroform (6 ml), and the mixture was stirred at room temperature for 45 minutes. 1M Hydrochloric acid was added and extracted with ethyl acetate. The organic layer was washed with saturated aqueous sodium hydrogencarbonate and brine, dried over anhydrous sodium sulfate, and concentrated under reduced pressure. The residue was recrystallized (chloroform/hexane) to give Co 106 (165 mg).

Example 26

35% Formalin (5 ml) and formic acid (5 ml) were added to Co 97 (250 mg), and the mixture was stirred at 10° C. for 90 minutes. After the mixture was allowed to cool, 1M sodium hydroxide was added and the reaction mixture was extracted with ethyl acetate. The organic layer was washed with brine, dried over anhydrous sodium sulfate, and concentrated under reduced pressure. The residue was purified with silica gel column chromatography (eluent; hexane:ethyl acetate=4:1), and recrystallized (chloroform/hexane) to give Co 107 (133 mg).

Example 27

Phosphorous oxychloride (50 ml) was added to Rco 76 (6.2 g), and the mixture was refluxed for 1 hour. The reaction solution was concentrated under reduced pressure and the residue was dissolved in chloroform. The chloroform layer was washed twice with saturated aqueous sodium hydrogencarbonate, dried over anhydrous magnesium sulfate, and concentrated under reduced pressure to give 6.0 g of crystals. To 802 mg of the crystals, thiomorpholine (500 mg) and benzene (10 ml) were added. The reaction mixture was heated with stirring at 70 C. for 1 hour, and then diluted with ethyl acetate. The organic layer was washed with saturated aqueous sodium hydrogencarbonate and brine, dried over anhydrous magnesium sulfate, concentrated under reduced pressure, and purified with silica gel column chromatography (hexane:ethyl acetate=5:1) to give p-toluenesulfonic acid 4-thiomorpholino 2-phenylquinazoline-6-yl (828 mg). 802 mg of this compound was dissolved in methanol (10 ml) and THF (10 ml). 20% Potassium hydroxide (1.0 g) was added to the solution and the mixture was stirred at 70 C. for 1 hour. Water and 1M hydrochloric acid was added to neutralize the solution. Then, the solution was extracted with ethyl acetate, and the organic layer was washed with brine. After the solution was dried over anhydrous magnesium sulfate, the solution was concentrated under reduced pressure and recrystallized (ethyl acetate-hexane) to give Co 108 (151 mg).

Example 28

Ammonium acetate (1.2 g) was added to acetic acid 2-methyl-4-oxo-4H-benzo[d][1,3]oxazine-6-yl ester (3 g), and the mixture was stirred at 150 C. for 30 minutes. After cooling to 80 C., methanol was added to the mixture and the mixture was stirred at 80 C. for 1 hour. After the mixture was allowed to cool, the precipitated crystals were, collected and washed with methanol to give crystals (930 mg). To a solution of the obtained crystals (918 mg) in DMSO (10 ml)/chloroform (5 ml), toluenesulfonyl chloride (1 ml), TEA (1 ml) and a catalytic amount of dimethylaminopyridine were added. The mixture was stirred at room temperature for 8 hours, and then extracted with ethyl acetate. The organic layer was washed with saturated aqueous sodium hydrogencarbonate and brine, dried over anhydrous sodium sulfate, and the solvent was evaporated under reduced pressure. Phosphorous oxychloride (15 ml) was added to the obtained residue and the mixture was refluxed for 15 hours. After the reaction solution was allowed to cool, phosphorous oxychloride was evaporated under reduced pressure. The residue was extracted with chloroform and washed with saturated aqueous sodium hydrogencarbonate. The organic layer was dried over anhydrous sodium sulfate, and concentrated under reduced pressure. The residue was purified with silica gel column chromatography (eluent; chloroform:methanol=50:1) to give a liquid material (577 mg). To a solution of the obtained material (577 mg) in toluene (20 ml), morpholine (2 g) was added, and the mixture was refluxed for 16 hours. The reaction solution was allowed to cool, and concentrated under reduced pressure. To a solution of the obtained residue in ethanol (15 ml), 20% potassium hydroxide (1 ml) was added, and the mixture was stirred at room temperature for 1 hour. The solvent was evaporated under reduced pressure. The residue was purified with silica gel column chromatography (eluent; chloroform: methanol=20:1), and recrystallized (chloroform/methanol/hexane) to give Co 109 (207 mg).

Example 29

Phosphorous oxychloride (10 mg) was added to Rco 78 (590 mg), and the mixture was refluxed for 0.5 hours. The reaction mixture was concentrated, diluted with chloroform, and washed with saturated aqueous sodium hydrogencarbonate. The organic layer was dried over anhydrous magnesium sulfate, and concentrated under reduced pressure. To the obtained colorless crystals, morpholine (10 ml) was added, and the mixture was refluxed for 12 hours. The reaction mixture was diluted with chloroform, washed with water and saturated aqueous sodium hydrogencarbonate, and dried over anhydrous magnesium sulfate. The obtained organic layer was concentrated under reduce pressure. The residue was crystallized from chloroform-methanol, and further recrystallized to give Co 110 (126 mg).

Example 30

Acetic acid (20 ml) and 48% hydrogen bromide (20 ml) were added to Rco 67 (957 mg), and the mixture was stirred at an oil bath temperature of 135 C. for 13 hours. After the mixture was allowed to cool to room temperature, precipitate was collected as a mixture of a starting material and a desired compound. To the obtained solid, acetic anhydride (30 ml) and sodium acetate (112 mg) were added and the reaction mixture was refluxed for 30 minutes. The reaction solution was allowed to cool, precipitate was collected. To the obtained solids, phosphorous oxychloride (10 ml) was added, and the mixture was refluxed for 30 minutes and concentrated under reduced pressure. The obtained residue was dissolved in chloroform and the solution was washed with saturated aqueous sodium hydrogencarbonate. The organic layer was dried over anhydrous magnesium sulfate, and concentrated under reduced pressure. To the obtained residue, morpholine (20 ml) was added and the mixture was refluxed for 15 hours. The reaction mixture was concentrated under reduced pressure and purified with silica gel column chromatography (eluent; chloroform:methanol=50:1). The obtained crystals were washed with a mixture of chloroform and ether to give Co 127 (193 mg).

Example 31

Iron (396 mg) was added to a solution of Co 111 (500 mg) in acetic acid (12 ml), and the mixture was stirred at 105 C. for 45 minutes. The reaction solution was allowed to cool. Chloroform and 1M sodium hydroxide were added to it. The mixture was filtered and extracted with chloroform. The organic layer was washed with brine, dried over anhydrous sodium sulfate, and concentrated under reduced pressure. The obtained residue was purified with silica gel column chromatography (eluent; chloroform:methanol 10:1) and recrystallized (chloroform/methanol/hexane) to give Co 129 (120 mg).

Example 32

1M Sodium hydroxide (8 ml) was added to a solution of Co 116 (564 mg) in ethanol (8 ml) and THF (8 ml), and the reaction mixture was stirred at room temperature for 15 hours. 1M Hydrochloric acid (8 ml) was added and the solution was extracted with ether. The organic layer was washed with brine, dried over anhydrous sodium sulfate, and concentrated under reduced pressure. The residue was recrystallized (methanol/ether/hexane) to give Co 130 (163 mg).

Example 33

Lithium aluminum hydride (67 mg) was added to a solution of Co 117 (325 mg) in THF (40 ml), and the reaction mixture was stirred at 0 C. for 2 hours. Water (0.1 ml), 1M sodium hydroxide (0.1 ml), and then water (0.3 ml) were added and the mixture was stirred at room temperature for 30 minutes. The mixture was dried over anhydrous sodium sulfate, filtered through silica gel, and concentrated under reduced pressure. The residue was recrystallized (THF/hexane) to give Co 131 (158 mg).

Example 34

Co 112 (860 mg) was dissolved in a mixture of THF (30 ml), methanol (30 ml) and ethanol (30 ml). 10% Pd—C (130 mg) was added and the reaction mixture was stirred under hydrogen atmosphere (1 atm) at room temperature for 2 hours. Insoluble materials were removed by filtration and the filtrate was concentrated to give 780 mg of solid. Of the solid, 202 mg was recrystallized (ethanol/methanol) to give Co 133 (148 mg).

Example 35

Co 133 (202 mg) was dissolved in pyridine (10 ml). Methanesulfonyl chloride (96 mg) was added to the reaction solution. The reaction mixture was stirred for 15 hours, and concentrated under reduced pressure. The obtained residue was dissolved in ethyl acetate. The organic layer was washed with water, dried over anhydrous magnesium sulfate, and concentrated under reduced pressure. The obtained crystals were purified with column chromatography (chloroform-methanol=100:1) and recrystallized (ethanol-ethyl acetate-hexane) to give Co 135.

Example 36

HOBt (75 mg) and EDCI hydrochloride (106 mg) were added to a solution of Co 131 (177 mg) in DMF (12 ml), and the reaction solution was stirred at 0 C. for 30 minutes and then at room temperature for 30 minutes. Aqueous ammonia (2 ml) was added and the mixture was stirred at room temperature for 3 hours. The reaction mixture was extracted with chloroform, and the organic layer was washed with water, dried over anhydrous sodium sulfate, and concentrated under reduced pressure. The residue was purified with silica gel column chromatography (eluent; chloroform:methanol=10:1) and recrystallized (chloroform/methanol/hexane) to give Co 136 (39 mg).

Example 37

Phosphorous oxychloride (15 ml) was added to Rco 87 (1.1 g), and the mixture was refluxed for 1 hour. The reaction mixture was allowed to cool, and concentrated under reduced pressure. The mixture was diluted with chloroform and the organic layer was washed with saturated aqueous sodium hydrogencarbonate, dried over anhydrous sodium sulfate, and concentrated under reduced pressure. To a solution of the obtained residue in toluene (40 ml), morpholine (5 g) was added and the reaction solution was refluxed for 17 hours, allowed to cool, and concentrated under reduced pressure. The residue was purified with silica gel column chromatography (eluent; chloroform:methanol=30:1), and recrystallized (chloroform/ether/hexane) to give Co 138 (869 mg).

Example 38

Acetic anhydride (0.75 ml) and pyridine (1 ml) were added to a solution of Co 129 (457 mg) in DMF (10 ml), and the reaction mixture was stirred at room temperature for 1 hour. 1M Sodium hydroxide (15 ml) and water were added and the reaction mixture was extracted with chloroform. The organic layer was dried over anhydrous sodium sulfate, and concentrated under reduced pressure. The residue was purified with silica gel column chromatography (eluent; chloroform:methanol=10:1), recrystallized (chloroform/methanol/hexane), and washed with ether to give Co 139 (358 mg).

Example 39

Benzene (10 ml), benzaldehyde (249 mg) and THF (10 ml) were added to Co 133 (476 mg). The reaction mixture was azeotropically refluxed for 2 hours and concentrated under reduced pressure, and the obtained residue was dissolved in methanol (20 ml). Under ice cooling, sodium borohydride (50 mg) was added. The reaction mixture was stirred at room temperature for 1 hour, and concentrated under reduced pressure. The residue was dissolved in ethyl acetate, and the organic layer was washed with water and brine, dried over anhydrous magnesium sulfate, and concentrated under reduced pressure. The residue was purified with silica gel column chromatography (chloroform:methanol=100:1), and recrystallized (ethyl acetate/hexane) to give Co 140 (259 mg).

Example 40

Co 133 (3.0 g) was dissolved in pyridine (50 ml). Benzenesulfonyl chloride (1.9 g) was added to the mixture at room temperature. After stirring the mixture for 2 hours, the solvent was evaporated under reduced pressure. Ethyl acetate and water were added to the obtained residue and then the organic layer was washed with brine three times. The obtained organic layer was dried over anhydrous magnesium sulfate, and concentrated under reduced pressure. The obtained solid was purified with silica gel column chromatography (chloroform:methanol=100:1) and recrystallized (ethanol) to give Co 141 (3.0 g).

Example 41

THF (15 ml) and phenyl isocyanate (207 mg) were added to Co 133 (540 mg). After the mixture was refluxed for 3 hours, phenyl isocyanate (500 mg) was again added. The mixture was then refluxed for 4 hours, 1M Sodium hydroxide (5 ml) was added. After the mixture was stirred for 15 minutes, 1M hydrochloric acid (5 ml) was added to neutralize it. The reaction mixture was extracted with chloroform, dried over anhydrous magnesium sulfate, and concentrated under reduced pressure. The obtained residue was purified with silica gel column chromatography (chloroform:methanol=50:1) and recrystallized (2-propanol/diethyl ether/hexane) to give Co 148 (180 mg).

Example 42

THF (15 ml) and TEA (520 mg) were added to Co 133 (440 mg). Phenyl chloroformate (498 mg) was added in dropwise to the reaction solution at room temperature, and stirred at room temperature for 2 hours. After adding methanol, 1M sodium hydroxide (5 ml) was added under ice cooling and the reaction mixture was stirred for 20 minutes. 1M Hydrochloric acid (5 ml) was added to neutralize it. The reaction mixture was extracted with chloroform, dried over anhydrous magnesium sulfate, and concentrated under reduced pressure. The obtained residue was purified with silica gel column chromatography (chloroform:methanol=50:1) and recrystallized (ethyl acetate) to give Co 149 (189 mg).

Example 43

Isonicotinoyl chloride hydrochloride (280 mg) and pyridine (0.127 ml) were added to a solution of Co 133 (253 mg) in THF (10 ml), and the reaction mixture was stirred at room temperature for 5.5 hours. Further, TEA (0.1 ml) was added and the mixture was stirred at room temperature for 2.5 hours. Then, 1M sodium hydroxide (0.786 ml) and methanol (4 ml) were added, and the reaction mixture was stirred at room temperature for 30 minutes to cleave the ester. After neutralization, most of the solvent was evaporated, the resulting precipitate was collected, washed with ethyl acetate and water, and recrystallized (ethanol) to give Co 150 (71 mg).

Example 44

Chlorooxoacetic acid ethyl ester (190 mg) and TEA (1 ml) were added to a solution of Co 97 (285 mg) in chloroform (12 ml), and the mixture was stirred at room temperature for 16 hours. The reaction mixture was extracted with chloroform, washed with water, dried over anhydrous sodium sulfate, and concentrated under reduced pressure. The residue was purified with silica gel column chromatography (eluent; chloroform:methanol=50:1), and recrystallized (chloroform/methanol/hexane) to give Co 159 (103 mg).

Example 45

Benzoyl isothiocyanate (1.2 ml) was added to a solution of Co 97 (1.2 g) in chloroform (30 ml) under ice cooling, and the mixture was stirred at room temperature for 3 hours. The precipitated crystals were collected. To the obtained crystals, 40% methylamine/methanol was added and the reaction mixture was stirred at room temperature for 1 hour, concentrated under reduced pressure, and purified with silica gel column chromatography to give 1-(4-morpholino-2-phenylquinazoline-6-yl)thiourea (1.1 g). To 266 mg of this compound, ethanol (5 ml), methanol (3 ml) and 40% chloroacetaldehyde (300 mg) were added. The reaction mixture was stirred for 4 days, diluted with ethyl acetate, washed with saturated aqueous sodium hydrogencarbonate, and dried over anhydrous magnesium sulfate. The residue was purified with silica gel column chromatography (hexane:ethyl acetate=2:1), and recrystallized (ethanol/hexane) to give Co 160 (49 mg).

Example 46

Acetic acid (5 ml) and 48% hydrobromic acid (5 ml) were added to Co 91 (500 mg), and the reaction solution was refluxed for 13 hours, and then concentrated. The reaction mixture was neutralized with 1M sodium hydroxide and saturated aqueous sodium hydrogencarbonate, and extracted with ethyl acetate. The organic layer was dried over anhydrous magnesium sulfate, and concentrated under reduced pressure. The obtained solid was purified with silica gel column chromatography (hexane:ethyl acetate=1:1), and recrystallized (ethanol) to give Co 162 (112 mg).

Example 47

3-Morpholinopropanol (93 mg) and a free form of Co 50 (203 mg) were added to a solution of diethyl azodicarboxylate (0.101 ml) and triphenylphosphine (168 mg) in THF (20 ml) and the mixture solution was stirred at 60 C. for 13 hours. Additional diethyl azodicarboxylate (0.1 ml), triphenylphosphine (170 mg) and 3-morpholinopropanol (93 mg) were added and the mixture was stirred at 60 C. This addition of the reagents was repeated again. After the reaction mixture was allowed to cool, water and ethyl acetate were added, and the reaction mixture was basified with saturated aqueous sodium hydrogencarbonate. After extraction with ethyl acetate, the solution was washed with brine. After the solution was dried over anhydrous sodium sulfate, the solvent was evaporated under reduced pressure. The obtained residue was purified with silica gel column chromatography (chloroform:methanol=98:2), and recrystallized (methanol) to give a free form of Co 58 (174 mg). The obtained free form (71 mg) was subjected to salt formation as described in EXAMPLE 18, and recrystallized (methanol) to give hydrochloride of Co 58 (68 mg).

Example 48

Potassium carbonate (1.10 g) was added to a solution of Co 61 (1.48 g) in methanol (15 ml) and water (15 ml). After the mixture was stirred at 80 C., additional methanol (8 ml) and water (8 ml) were added and the mixture was stirred at 80 C. for 12 hours. After the reaction mixture was allowed to cool, crystals were collected, purified with silica gel column chromatography (chloroform:methanol=98:2), and crystallized (methanol) to give a free form of Co 59 (1.13 g). The obtained free form (160 mg) was subjected to salt formation as described in EXAMPLE 18, and recrystallized (methanol) to give dihydrochloride of Co 59 (146 mg).

Example 49

Anhydrous trifluoroacetic acid (1.07 ml) and dimethylaminopyridine (78 mg) were added to a solution of a free form of Co 31 (2.21 g) in pyridine (70 ml) under ice cooling. After the mixture solution was stirred for 1 hour, more anhydrous trifluoroacetic acid (0.5 ml) and dimethylaminopyridine (30 mg) were added, and the mixture was stirred under ice cooling for 1 hour. The solvent was evaporated under reduced pressure, water and ethyl acetate were added, and the precipitated crystals were filtered and washed with ethyl acetate to give Co 60 (2.66 g).

Example 50

Water (0.645 ml), dibromoethane (1.11 ml), tetrabutylammonium hydrogensulfate (22 mg) and 2M aqueous sodium hydroxide (2.58 ml) were added to a free form of Co 50 (1.29 g), and the mixture was stirred 60 C. for 6 hours. Chloroform was added to the mixture, unsoluble materials were filtered, and the filtrate was extracted with chloroform and then washed with brine. After the solution was dried over anhydrous sodium sulfate, the solvent was evaporated under reduced pressure, and the obtained residue was purified with silica gel column chromatography (chloroform:methanol=98:2) to give Co 62 (376 mg).

Example 51

1-Methylpiperazine (139 mg) and potassium carbonate (256 mg) were added to a solution of Co 62 (211 mg) in DMF (5 ml) and the mixture solution was stirred at 60 C. for 4 hours. The solvent was evaporated under reduced pressure, water and THF were added to the obtained residue, the mixture was extracted with ethyl acetate, and then the solvent was evaporated under reduced pressure. The obtained residue was purified with silica gel column chromatography (chloroform:methanol=97:3~95:5) to give a free form of Co 64 (198 mg). The obtained free form (198 mg) was subjected to salt formation as described in EXAMPLE 18, and recrystallized (methanol) to give trihydrochloride of Co 64 (160 mg).

Example 52 tert-Butyl piperazine-1-carboxylate (285 mg) and potassium carbonate (282 mg) were added to a solution of Co 62 (232 mg) in DMF (5 ml) and the mixture solution was stirred at 60 C. for 17 hours. The solvent was evaporated under reduced pressure, water was added to the obtained residue, and the resulting mixture was extracted with ethyl acetate and then washed with brine. After the solution was dried over anhydrous sodium sulfate, the solvent was evaporated under reduced pressure and the obtained residue was purified with silica gel column chromatography (chloroform:methanol=99:1) to give solid (227 mg). 4M Hydrogen chloride/ethyl acetate (1 ml) were added to a solution of the obtained solid (212 mg) in dioxane (3 ml) and methanol (3 ml), and the mixture was stirred at room temperature for 4 hours. The resulting mixture was concentrated and the residue was recrystallized (methanol) to give Co 69 (144 mg).

Example 53

Paraformaldehyde (15 mg) and acetic acid (81 ml) were added to a solution of a free form of Co 59 (216 mg) in THF (3 ml). After the mixture was stirred at room temperature for 10 minutes, sodium triacetoxyborohydride (199 mg) was added and the mixture was stirred at room temperature for 21 hours. Then, liquid formaldehyde (0.44 ml), acetic acid (5.5 ml) and sodium triacetoxyborohydride (704 mg) were added in 3 divided portions, and the reaction solution was stirred at room temperature for 4 days. The reaction mixture was neutralized with 2M aqueous sodium hydroxide, and THF was added. After the reaction solution was extracted with ethyl acetate, it was washed with brine. After it was dried over anhydrous sodium sulfate, the solvent was evaporated under reduced pressure, and the obtained residue was purified with silica gel column chromatography (chloroform methanol=98:2) to give a free form of Co 70 (162 mg). The obtained free form (48 mg) was subjected to salt formation as described in EXAMPLE 18, and recrystallized (methanol) to give dihydrochloride of Co 70 (53 mg).

Example 54

After a free form of Co 50 (322 mg), 1,3-dioxolane-2-one (814 mg) and potassium carbonate (192 mg) were stirred at 100 C. for 2 hours, more 1,3-dioxolane-2-one (680 mg) was added and the mixture was stirred at 100 C. for 17 hours. Then, DMF (3 ml) was added and the mixture was stirred at 100 C. for 2 hours, and further 1,3-dioxolane-2-one (670 mg) was added and the mixture was stirred at 100 C. for 20 hours. After the reaction mixture was allowed to cool, the solvent was evaporated under reduced pressure, and water was added.

Then, 1M aqueous hydrochloric acid was added until bubbles no longer appeared. The precipitated crystals were collected and recrystallized (methanol) to give Co 77 (164 mg).

Example 55

Phosphorus oxychloride (10 ml) was added to Rco 48 (1.07 g), and the mixture was refluxed for 2.5 hours. The solvent was evaporated, and the reaction mixture was azeotropically concentrated with toluene. THF (15 ml) was added to the obtained residue. After morpholine (10 ml) was slowly added in dropwise under ice cooling, the ice bath was removed and the reaction mixture was refluxed for 30 minutes. Ethyl acetate and THF were added to the reaction mixture and the mixture was washed with water and brine. After it was dried over anhydrous sodium sulfate, the solvent was evaporated under reduced pressure and the obtained residue was purified with silica gel column chromatography (chloroform methanol=98:2) to give bis(morpholinoamido) 2-(4-morpholinopyrido[3'2':4,5]furo[3,2-d]pyrimidine-2-yl)phenylphosphonate (594 mg). Formic acid (4 ml) was added to this compound (360 mg) and the mixture was stirred at 100 C. for 3 days. The solvent was evaporated under reduced pressure, ethyl acetate and water were added, and the mixture was neutralized with saturated aqueous sodium hydrogencarbonate under ice cooling. The precipitated crystals were filtered to give crystals (162 mg). The obtained crystals (123 mg) were recrystallized (methanol-THF) to give Co 79 (122 mg).

Example 56

Dioxane (3.9 ml) and 6M hydrochloric acid (5.5 ml) were added to Co 80 (220 mg), and the mixture was refluxed for 3 days. After the reaction mixture was allowed to cool, it was neutralized, extracted with a mixture solution of ethyl acetate and THF, and washed with brine. After it was dried over anhydrous sodium sulfate, the solvent was evaporated under reduced pressure, and the obtained residue was purified with silica gel column chromatography (chloroform:methanol=96:4) to give crystals (83 mg). The obtained crystals (81 mg) were recrystallized (THF-methanol) to give Co 81 (53 mg).

Example 57

After a solution of a free form of Co 168 (151 mg) in pyridine (9 ml) was cooled in an ice bath, acetic anhydride (4.5 ml) was added, and the mixture was stirred under ice cooling. After the reaction completed, the reaction mixture was poured into water with ice, extracted with ethyl acetate, and washed with brine. After it was dried over anhydrous sodium sulfate, the solvent was evaporated under reduced pressure to give a free form of Co 183 (158 mg). The obtained free form (156 mg) was subjected to salt formation as described in EXAMPLE 18, and the obtained crystals were recrystallized (methanol) to give hydrochloride of Co 169 (93 mg).

Example 58

2-Morpholinoethanol (806 mg) was added in dropwise to a solution of 60% sodium hydroxide (63 mg) in DMF (5 ml), and the mixture solution was stirred at room temperature for 15 minutes. Then, a free form of Co 179 (285 mg) was added and the mixture was stirred at 60 C. for 23 hours. Then, a mixture, which was prepared by adding 2-morpholinoethanol (806 mg) in dropwise to 60% sodium hydroxide (63 mg) in DMF (1 ml) and stirring at room temperature for 15 minutes, was added in dropwise to the reaction mixture and the resulting mixture was stirred at 60 C. This addition of sodium 2-morpholinoethoxide was conducted 3 times. The solvent was evaporated under reduced pressure, water and THF were added to the obtained residue, and the mixture was extracted with ethyl acetate and then washed with brine. After it was dried over anhydrous sodium sulfate, the solvent was evaporated under reduced pressure, and the obtained residue was purified with silica gel column chromatography (chloroform:methanol=95:5) to give a free form of Co 192 (529 mg). The obtained free form (404 mg) was subjected to salt formation as described in EXAMPLE 18, and the obtained crystals were recrystallized (methanol) to give dihydrochloride of Co 192 (320 mg).

What is claimed is:

1. A fused heteroaryl compound of the formula:

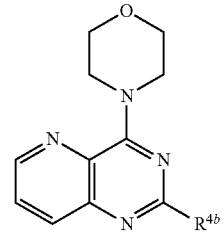

wherein:
R$^{4b}$ is phenyl, pyridyl, pyrimidinyl, indolyl, or indazolyl, wherein phenyl, pyridyl, pyrimidinyl, indolyl, or indazolyl is optionally and independently substituted with one or more substituents selected from Cl, Br, F, methyl, ethyl, CN, CO$_2$H, OH, OCH$_3$, OCH$_2$CH$_2$NH$_2$, NH$_2$, NHCH$_3$, NHSO$_2$CH$_3$, SCH$_3$, SO$_2$CH$_3$, SO$_2$NH$_2$, SO$_2$NHCH$_3$, and SO$_2$N(CH$_3$)$_2$.

2. The fused heteroaryl compound of claim 1, wherein R4b is phenyl, wherein phenyl is optionally and independently substituted with one or more substituents selected from Cl, Br, F, methyl, ethyl, CN, CO$_2$H, OH, OCH$_3$, OCH$_2$CH$_2$NH$_2$, NH$_2$, NHCH$_3$, NHSO$_2$CH$_3$, SCH$_3$, SO$_2$CH$_3$, SO$_2$NH$_2$, SO$_2$NHCH$_3$, and SO$_2$N(CH$_3$)$_2$.

3. The fused heteroaryl compound of claim 1, wherein R4b is pyridyl, wherein pyridyl is optionally and independently substituted with one or more substituents selected from Cl, Br, F, methyl, ethyl, CN, CO$_2$H, OH, OCH$_3$, OCH$_2$CH$_2$NH$_2$, NH$_2$, NHCH$_3$, NHSO$_2$CH$_3$, SCH$_3$, SO$_2$CH$_3$, SO$_2$NH$_2$, SO$_2$NHCH$_3$, and SO$_2$N(CH$_3$)$_2$.

4. The fused heteroaryl compound of claim 1, wherein R4b is pyrimidinyl, wherein pyrimidinyl is optionally and independently substituted with one or more substituents selected from Cl, Br, F, methyl, ethyl, CN, CO$_2$H, OH, OCH$_3$, OCH$_2$CH$_2$NH$_2$, NH$_2$, NHCH$_3$, NHSO$_2$CH$_3$, SCH$_3$, SO$_2$CH$_3$, SO$_2$NH$_2$, SO$_2$NHCH$_3$, and SO$_2$N(CH$_3$)$_2$.

5. The fused heteroaryl compound of claim 1, wherein R4b is indolyl, wherein indolyl is optionally and independently substituted with one or more substituents selected from Cl, Br, F, methyl, ethyl, CN, CO$_2$H, OH, OCH$_3$, OCH$_2$CH$_2$NH$_2$, NH$_2$, NHCH$_3$, NHSO$_2$CH$_3$, SCH$_3$, SO$_2$CH$_3$, SO$_2$NH$_2$, SO$_2$NHCH$_3$, and SO$_2$N(CH$_3$)$_2$.

6. The fused heteroaryl compound of claim 1, wherein R4b is indazolyl, wherein indazolyl is optionally and independently substituted with one or more substituents selected from Cl, Br, F, methyl, ethyl, CN, CO$_2$H, OH, OCH$_3$, OCH$_2$CH$_2$NH$_2$, NH$_2$, NHCH$_3$, NHSO$_2$CH$_3$, SCH$_3$, SO$_2$CH$_3$, SO$_2$NH$_2$, SO$_2$NHCH$_3$, and SO$_2$N(CH$_3$)$_2$.

* * * * *